(12) United States Patent
Sims et al.

(10) Patent No.: US 11,788,120 B2
(45) Date of Patent: Oct. 17, 2023

(54) RNA PRINTING AND SEQUENCING DEVICES, METHODS, AND SYSTEMS

(71) Applicant: The Trustees of Columbia University in the City of New York, New York, NY (US)

(72) Inventors: Peter A. Sims, Ardsley, NY (US); Sayantan Bose, Collegeville, PA (US); Jinzhou Yuan, Edgewater, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 419 days.

(21) Appl. No.: 16/766,928

(22) PCT Filed: Nov. 27, 2018

(86) PCT No.: PCT/US2018/062650
§ 371 (c)(1),
(2) Date: May 26, 2020

(87) PCT Pub. No.: WO2019/104337
PCT Pub. Date: May 31, 2019

(65) Prior Publication Data
US 2021/0254143 A1    Aug. 19, 2021

Related U.S. Application Data

(60) Provisional application No. 62/590,889, filed on Nov. 27, 2017.

(51) Int. Cl.
*C12Q 1/6834* (2018.01)
*C12Q 1/686* (2018.01)
*C12Q 1/6869* (2018.01)
*B01L 3/00* (2006.01)

(52) U.S. Cl.
CPC .......... *C12Q 1/6834* (2013.01); *B01L 3/5027* (2013.01); *B01L 2300/0829* (2013.01); *C12Q 1/686* (2013.01); *C12Q 1/6869* (2013.01)

(58) Field of Classification Search
CPC .... C12Q 1/6834; C12Q 1/686; C12Q 1/6869; B01L 3/5027; B01L 2300/0829
See application file for complete search history.

(56) References Cited

U.S. PATENT DOCUMENTS

| | | | |
|---|---|---|---|
| 8,835,358 B2 | 9/2014 | Fodor et al. | |
| 9,174,216 B2 | 11/2015 | Handique et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,708,659 B2 | 7/2017 | Fodor et al. | |
| 9,816,137 B2 | 11/2017 | Fodor et al. | |
| 9,845,502 B2 | 12/2017 | Fodor et al. | |
| 10,155,981 B2 | 12/2018 | Brenner et al. | |
| 10,227,648 B2 | 3/2019 | Hindson et al. | |
| 10,240,197 B1 | 3/2019 | Brenner et al. | |
| 10,273,541 B2 | 4/2019 | Hindson et al. | |
| 10,280,459 B1 | 5/2019 | Brenner et al. | |
| 2003/0108867 A1 | 6/2003 | Chee et al. | |
| 2006/0177833 A1 | 8/2006 | Brenner | |
| 2012/0088691 A1 | 4/2012 | Chen et al. | |
| 2012/0142014 A1 | 6/2012 | Cai | |
| 2014/0031243 A1 | 1/2014 | Cai et al. | |
| 2014/0073520 A1 | 3/2014 | Cai et al. | |
| 2014/0170645 A1 | 6/2014 | Jovanovich et al. | |
| 2014/0206554 A1 | 7/2014 | Hindson et al. | |
| 2015/0329891 A1 | 11/2015 | Tan et al. | |
| 2016/0244825 A1 | 8/2016 | Vigneault et al. | |
| 2017/0081705 A1 | 3/2017 | Davies et al. | |
| 2017/0337459 A1 | 11/2017 | Fodor et al. | |
| 2018/0216160 A1 | 8/2018 | Abate et al. | |
| 2019/0064168 A1 | 2/2019 | Handique et al. | |
| 2019/0085324 A1 | 3/2019 | Regev et al. | |
| 2019/0085412 A1 | 3/2019 | Fan et al. | |
| 2019/0127782 A1 | 5/2019 | Regev et al. | |
| 2019/0345488 A1 | 11/2019 | Soumillon et al. | |

FOREIGN PATENT DOCUMENTS

| WO | 0065094 A2 | 11/2000 |
| WO | 2010138960 A2 | 12/2010 |
| WO | 2011021102 A2 | 2/2011 |
| WO | 2013188872 A1 | 12/2013 |
| WO | 2014089700 A1 | 6/2014 |
| WO | 2014089700 A9 | 9/2014 |
| WO | 2014201273 A1 | 12/2014 |

(Continued)

OTHER PUBLICATIONS

Bose et al., "Scalable microfluidics for single-cell RNA printing and sequencing," Genome Biology, Jun. 6, 2015, vol. 16(120), pp. 1-16.
Cai, "Turning single cells into microarrays by super-resolution barcoding", Briefings In Functional Genomics, Nov. 22, 2012, vol. 12(2), pp. 75-80.
Chen et al., "Spatially resolved, highly multiplexed RNA profiling in single cells," Science, Apr. 24, 2015, vol. 348(6233): aaa6090, pp. 1-36.
Chu et al., "RNA Sequencing: Platform Selection, Experimental Design, and Data Interpretation", Nucleic Acid Therapeutics, Aug. 2012, vol. 22(4), pp. 271-274.
Dey et al., "Integrated genome and transcriptome sequencing of the same cell", Nature Biotechnology, Jan. 19, 2015, vol. 33(3), pp. 285-289.

(Continued)

*Primary Examiner* — Cynthia B Wilder
(74) *Attorney, Agent, or Firm* — CASIMIR JONES, S.C.; Jason R. Bond

(57) ABSTRACT

Described herein are devices, systems, and methods for trapping single-cell lysates in sealed, microwells capable of printing RNA on glass or capturing RNA on beads. These provide efficient, inexpensive manipulation of RNA from individual cells suitable for single-cell transcriptomics on a large scale. Also described are dual barcode capture beads and merged barcode capture beads.

12 Claims, 30 Drawing Sheets

Specification includes a Sequence Listing.

(56) References Cited

FOREIGN PATENT DOCUMENTS

| WO | 2015031691 A1 | 3/2015 |
|---|---|---|
| WO | WO 2015/031691 A1 | 3/2015 |
| WO | 2015044428 A1 | 4/2015 |
| WO | 2015164212 A1 | 10/2015 |
| WO | 2016040476 A1 | 3/2016 |
| WO | WO 2016/040476 A1 | 3/2016 |
| WO | 2016145409 A1 | 9/2016 |
| WO | 2016191533 A1 | 12/2016 |
| WO | 2016207441 A1 | 12/2016 |
| WO | WO 2016/191533 A1 | 12/2016 |
| WO | 2017059094 A2 | 4/2017 |
| WO | 2017087873 A1 | 5/2017 |
| WO | 2017112957 A1 | 6/2017 |
| WO | WO 2017124101 * | 7/2017 |
| WO | 2017164936 A1 | 9/2017 |
| WO | 2019046307 A1 | 3/2019 |
| WO | 2019079399 A1 | 4/2019 |

OTHER PUBLICATIONS

Fan et al., "Combinatorial labeling of single cell for gene expression cytometry," Science, Feb. 6, 2015, vol. 347(6222), pp. 628, 1258367-1-8.

Farmer, "Systems Biology Faculty Nab Chan Zuckerberg Initiative Grants to Advance Human Cell Atlas", Oct. 16, 2017, Columbia University, Department of Systems Biology, Columbia Systems Biology, https://systemsbiology.columbia.edu/news/systems-biology-faculty-nab-chan-zuckerberg-initiative-grants-to-advance-human-cell-atlas.

Fu et al., "Single Cell Total RNA Sequencing through Isothermal Amplification in Picoliter-Droplet Emulsion", Analytical Chemistry, Oct. 26, 2016, vol. 88(22), pp. 10795-10799.

Gierahn et al., "Seq-Well: A Portable, Low-Cost Platform for High-Throughput Single-Cell RNA-Seq of Low-Input Samples", Nature Methods, Apr. 2017, vol. 14(4), pp. 395-398.

Goodarzi et al., "Revealing Global Regulatory Perturbations across Human Cancers", Molecular Cell, Dec. 11, 2009, vol. 36(5), pp. 900-911.

Habib et al., "Div-Seq: Single-nucleus RNA-Seq reveals dynamics of rare adult newborn neurons", Science, Jul. 28, 2016, vol. 353(6302), pp. 1-8.

Hashimshony et al., "CEL-Seq: single-cell RNA-Seq by multiplexed linear amplification", Cell Reports, Sep. 27, 2012, vol. 2(3) pp. 666-673.

Hiroaki, "Systems Biology: A Brief Overview," Science, vol. 295, No. 5560, pp. 1662-1664, Mar. 2002 (Abstract).

International Preliminary Report on Patentability for International Application No. PCT/US2016/034270 dated Dec. 7, 2017.

International Search Report and Written Opinion for International Application No. PCT/US2016/034270 dated Oct. 7, 2016.

International Search Report and Written Opinion for International Application No. PCT/US2018/062650 dated Feb. 13, 2019.

Kimmerling et al., "A microfluidic platform enabling single-cell RNA-seq of multigenerational lineages", Nature Communications, Jan. 6, 2016, vol. 7, pp. 1-7.

Kitano, "Systems Biology: A Brief Overview," Science, Mar. 1, 2002, vol. 295(5560), pp. 1662-1664.

Klein et al., "Droplet Barcoding for Single-Cell Transcriptomics Applied to Embryonic Stem Cells", Cell, May 21, 2015, vol. 161(5), pp. 1187-1201.

Kolodziejczyk et al.,"The technology and biology of single-cell RNA sequencing," Molecular Cell, May 21, 2015, vol. 58(4), pp. 610-620.

Lan et al., "Single-cell genome sequencing at ultra-high-throughput with microfluidic droplet barcoding", Nature Biotechnology, Jul. 2017, vol. 35(7), pp. 640-646 (Abstract).

Liu et al., "Emerging imaging and genomic tools for developmental systems biology," Developmental Cell, Mar. 21, 2016, vol. 36(6), pp. 597-610.

McDonald et al., "Poly(dimethylsiloxane) as a Material for Fabricating Microfluidic Devices", Accounts of Chemical Research, Jul. 2002, vol. 35(7), pp. 491-499.

Meade-Kelly, "Divide and conquer: New single cell approach broadens range of cell types that can be studied in the brain", Jul. 29, 2016, Broad Institute, Broadminded Blog, https://www.broadinstitute.org/blog/divide-and-conquer-new-single-cell-approach-broadens-range-cell-types-can-be-studied-brain.

Men et al., "Digital Polymerase Chain Reaction in an Array of Femtoliter Polydimethylsiloxane Microreactors", Analytical Chemistry, Apr. 7, 2012, vol. 84(10), pp. 4262-4266.

Office Action (Communication Pursuant to Article 94(3) EPC) dated Dec. 9, 2019 for European Application No. 16733232.9.

Shiroguchi et al., "Digital RNA sequencing minimizes sequence-dependent bias and amplification noise with optimized single-molecule barcodes", Proceedings of the National Academy of Sciences, Jan. 24, 2012, vol. 109(4), pp. 1347-1352.

Streets et al., "Microfluidic single-cell whole-transcriptome sequencing," Proceedings of the National Academy of Sciences, May 13, 2014, vol. 111(19), pp. 7048-7053.

Sweedler et al., "Single cell analysis", Analytical and Bioanalytical Chemistry, Jan. 2007, vol. 387(1), pp. 1-2.

Van Der Maaten et al., "Visualizing Data using t-SNE", Journal of Machine Learning Research, Nov. 2008, vol. 9, pp. 2579-2605.

White et al., "High-throughput microfluidic single-cell RT-qPCR", Proceedings of the National Academy of Sciences ol the United States of America, Jun. 17, 2011, vol. 108(34), pp. 13999-14004.

Wu et al., "Quantitative assessment of single-cell RNA-sequencing methods", Nature Methods, Oct. 20, 2013, vol. 11(1), pp. 41-46.

Yuan et al., "An Automated Microwell Platform for Large-Scale Single Cell RNA-Seq", Scientific Reports, Sep. 27, 2016, vol. 6, pp. 1-10.

Zilionis et al., "Single-cell barcoding and sequencing using droplet microfluidics", Nature Protocols, Dec. 8, 2016, vol. 12(1), pp. 44-73.

Gole et al.. Massively parallel polymerase cloning and genome sequencing of single cells using nanoliter microwells. Nature Biotechnology. 2013. vol 31(12), 1126-1132.

Koshkin et al., LNA (locked nucleic acid): an RNA mimic forming exceedingly stable LNA:LNA dkuplexes. Journal of the American Chemical Society, 1998, 120(50):13252-13253.

Mair et al., A Targeted Multi-omic Analysis Approach Measures Protein Expression and Low-Abundance Transcripts on the Single-Cell Level. Cell Reports. 2020. 31, 107499. 20 pages.

Marcus et al., Microfluidic Single-Cell mRNA Isolation and Analysis. Anal. Chem. 2006, 78, 9, 3084-3089.

Marcus et al., Parallel Picoliter RT-PCR Assays Using Microfluidics. Anal. Chem. 2006, 78, 3, 956-958.

Marcus. Single Cell Gene Expression Analysis Using Microfluidics. Thesis, Clifornia Institute of Technology. 2006. 179 pages.

Wang et al., RNA-Seq: a revolutionary tool for transcriptomics. Nat Rev Genet. 2009; 10(1):57-63.

Li et al., "Injection Molded Microfludics for Establishing High-Density Single Cell Arrays in an Open Hydrogel Format," Analytical Chemistry, vol. 92, No. 3, pp. 2794-2801, Jan. 2020.

* cited by examiner

Bright Field Fluorescence After Fluorescence After
 Reverse Transcription RNase Digestion

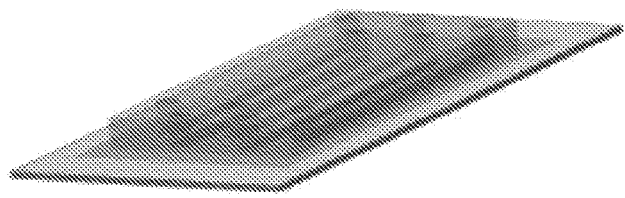
Fig. 5A
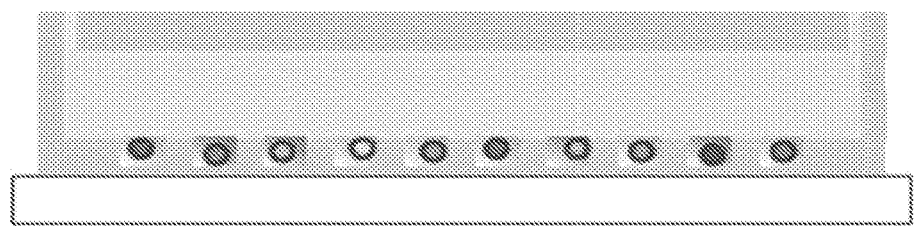
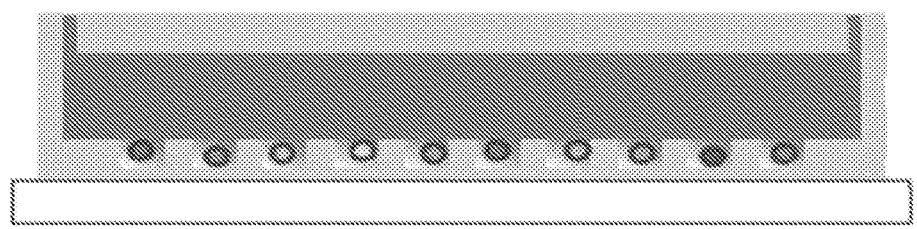
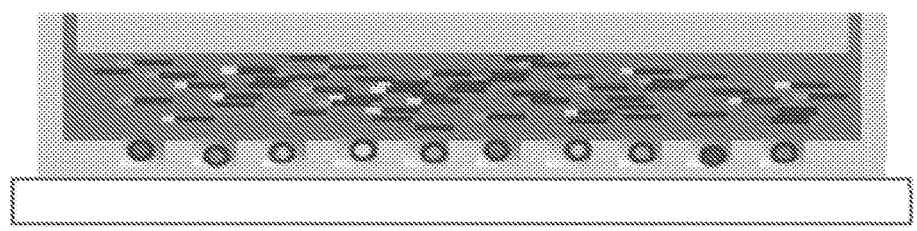
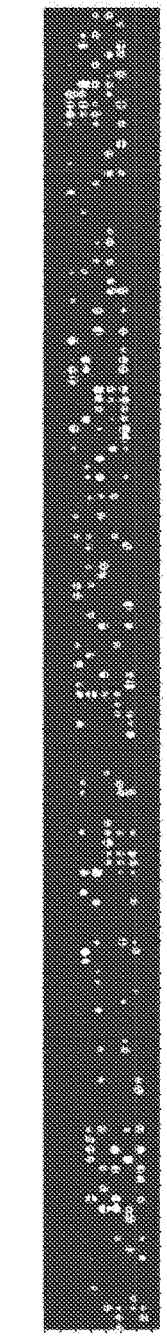
Fig. 5B
Fig. 5C

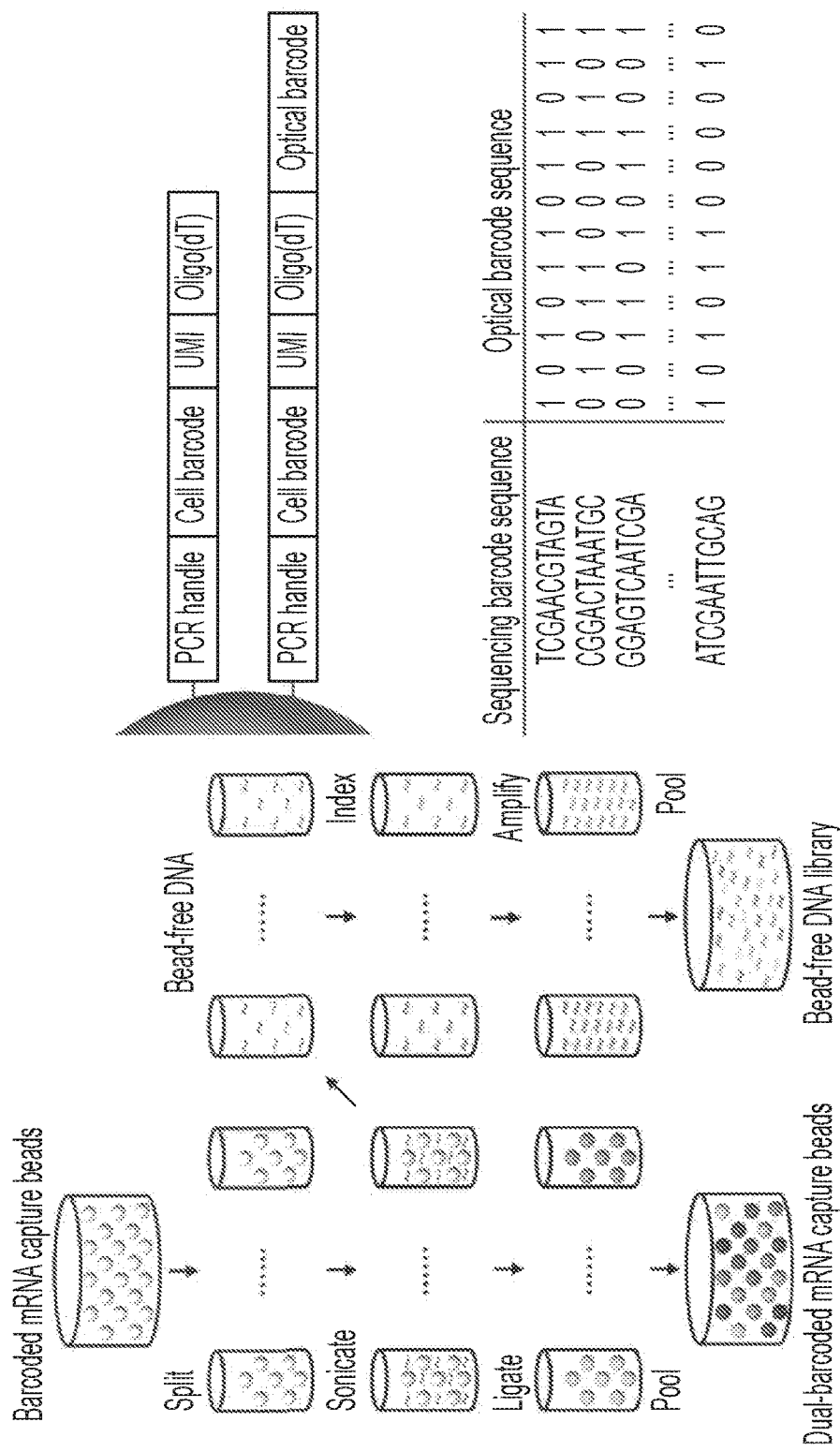
FIG. 15A (left)
FIG. 15B (upper right)
FIG. 15C (lower right)

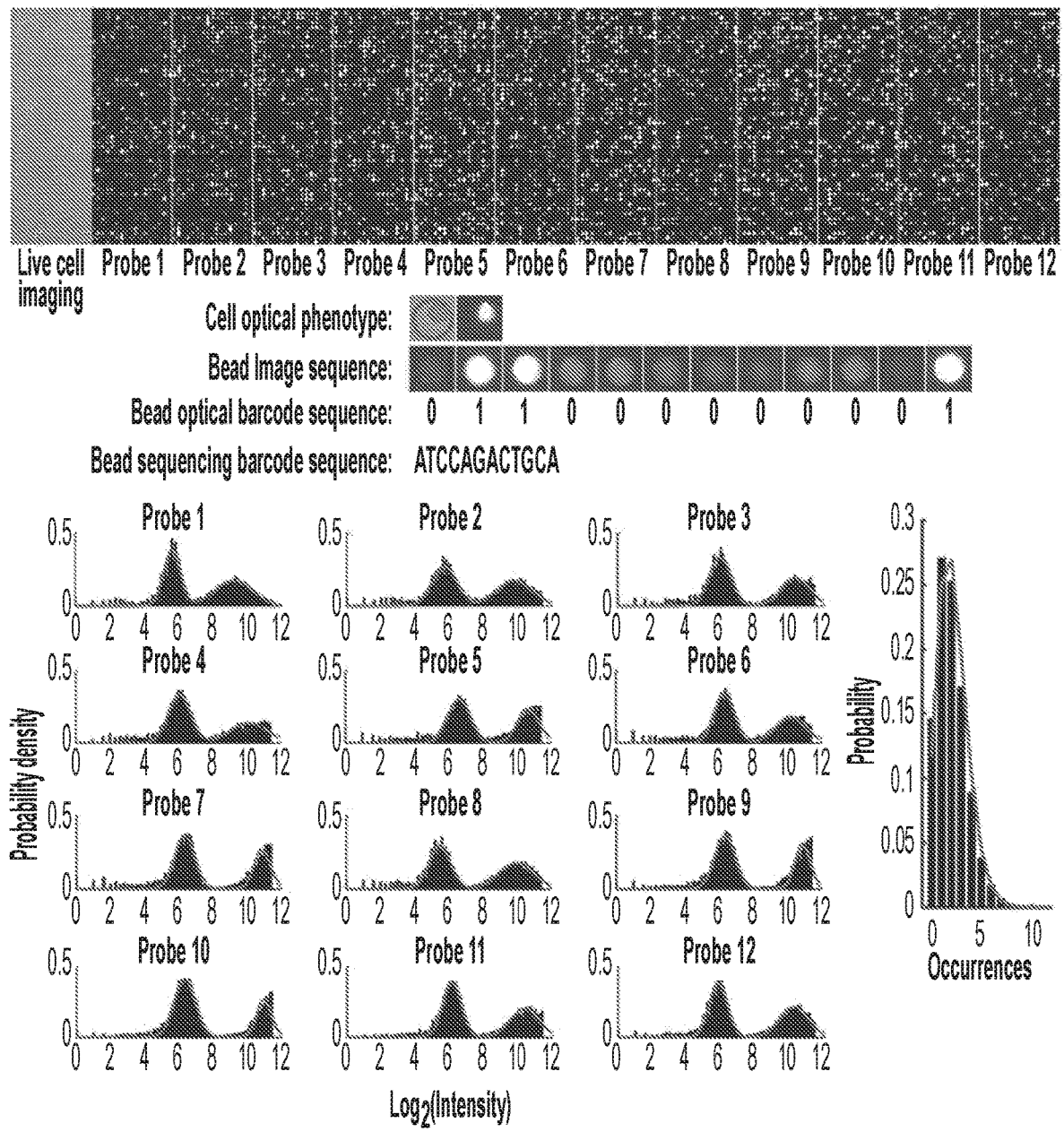
FIG. 16A (top)
FIG. 16B (bottom left)
FIG. 16C (bottom right)

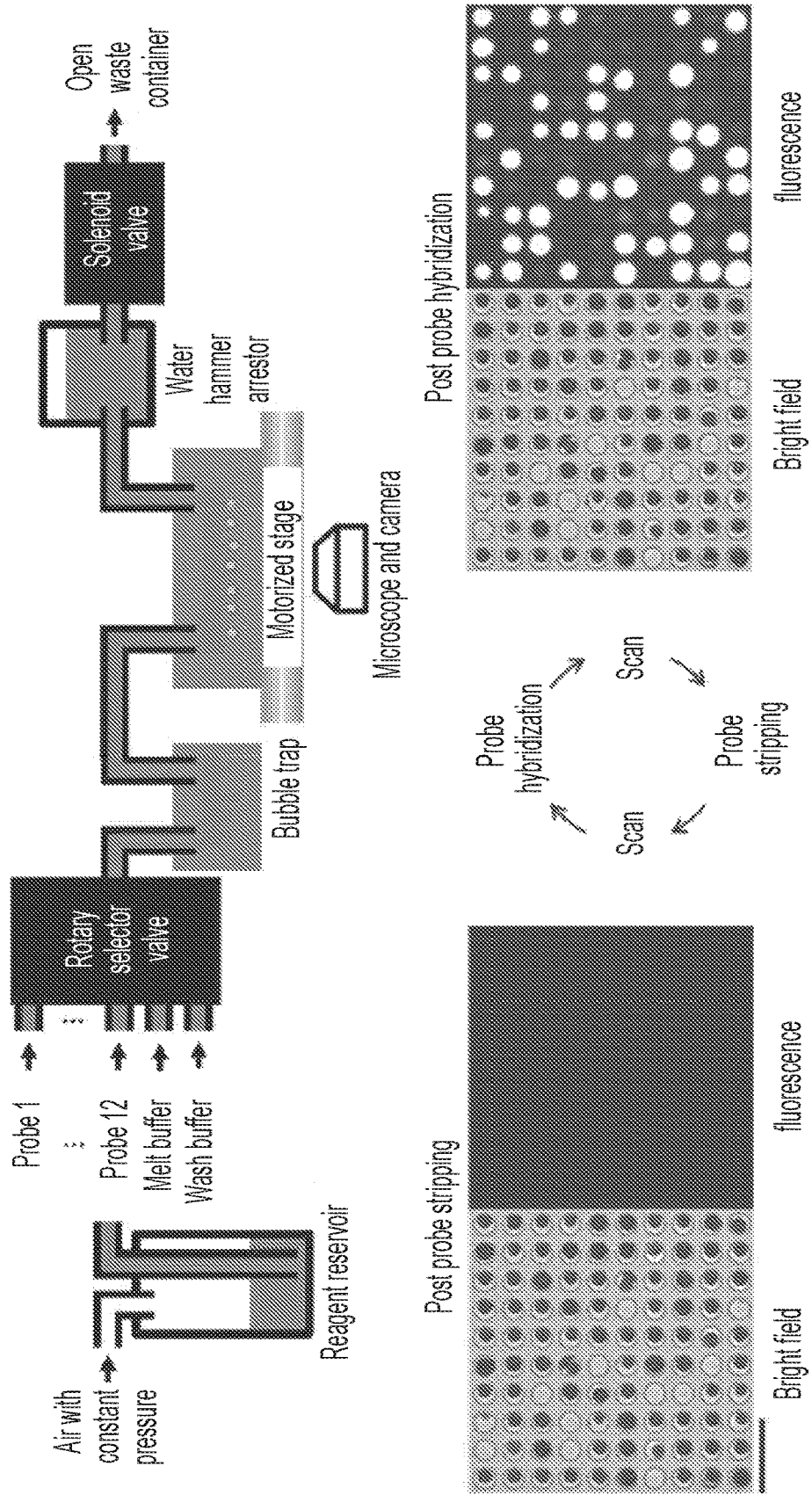
FIG. 17A (top)
FIG. 17B (bottom)

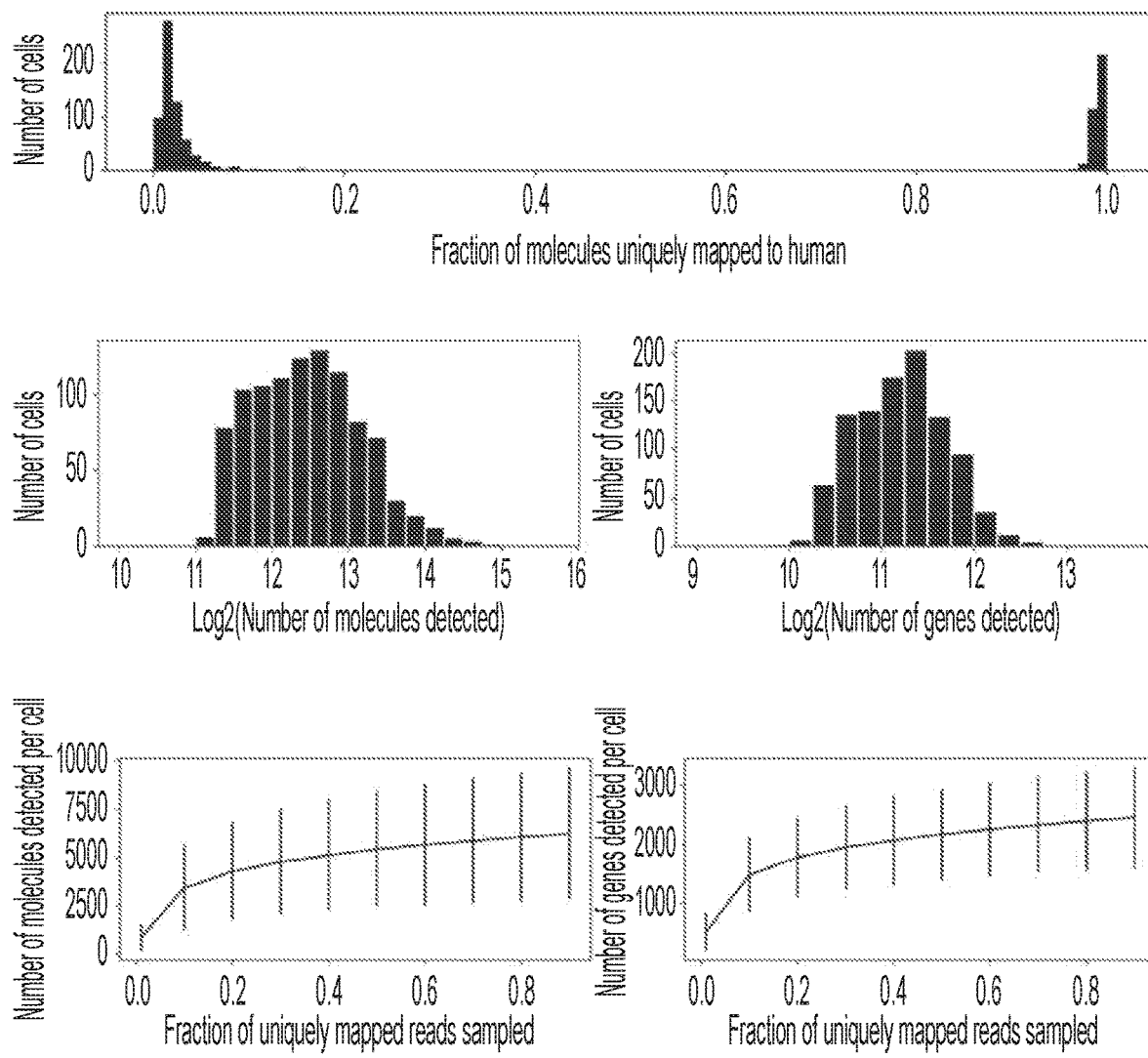
FIG. 18A (top)
FIG. 18B (center left)
FIG. 18C (center right)
FIG. 18D (bottom left)
FIG. 18E (bottom right)

FIG. 20A (top)

FIG. 20B (bottom)

FIG. 21A (top)

FIG. 21B (bottom)

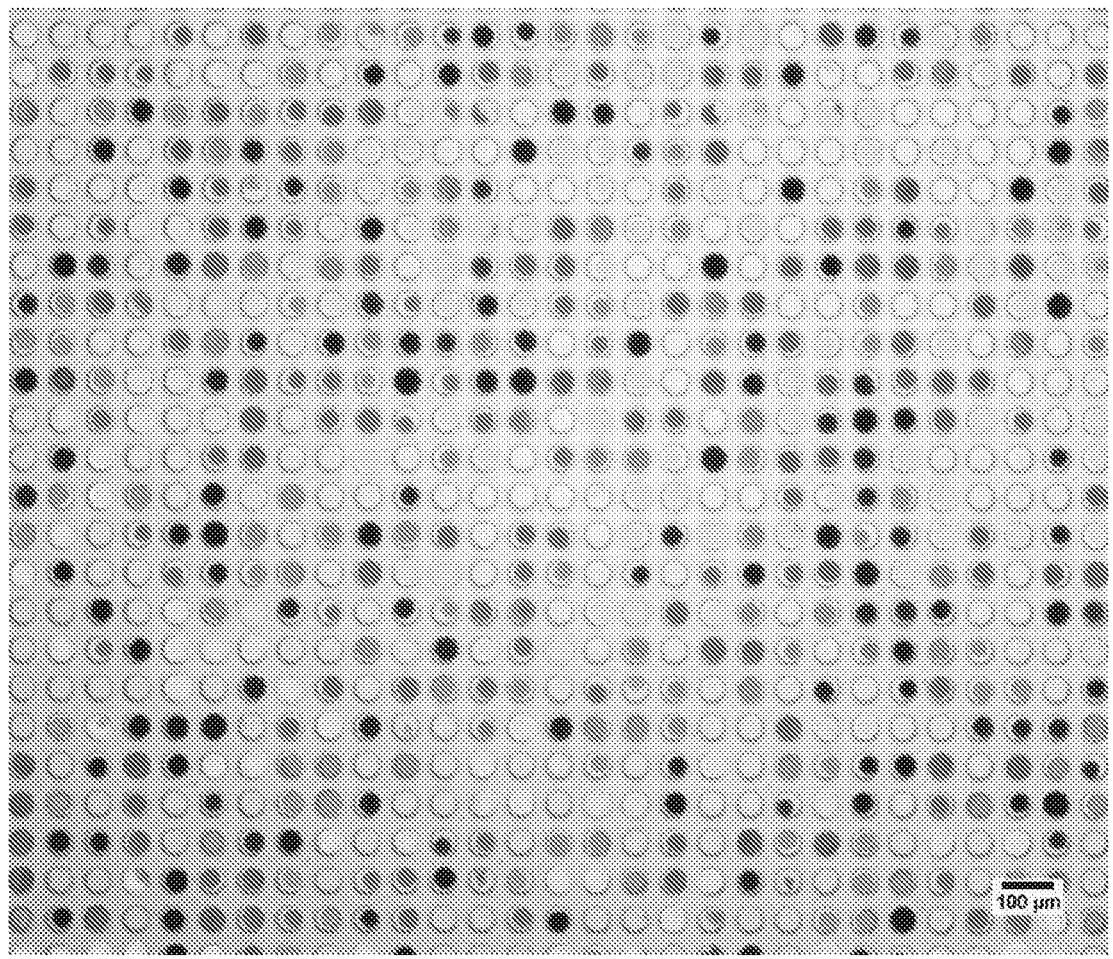
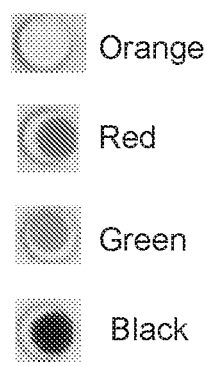
Fig. 26

RNA PRINTING AND SEQUENCING DEVICES, METHODS, AND SYSTEMS

STATEMENT OF GOVERNMENTAL INTEREST

This invention was made with government support under Contract Nos. EB016071 and CA202827 awarded by the National Institutes of Health. The government has certain rights in the invention.

SEQUENCE LISTING

The text of the computer readable sequence listing filed herewith, titled "39989-252_SEQUENCE_LISTING", created Mar. 15, 2023, having a file size of 4,643,474 bytes, is hereby incorporated by reference in its entirety.

BACKGROUND

Single cell analysis is important for understanding how cells respond to drugs and other perturbations because phenotypic responses are asynchronous and cells are often both genetically and epigenetically heterogeneous. In the absence of artificial or external perturbations, the natural processes of cellular differentiation during development and malignant transformation in cancer also occur asynchronously and give rise to phenotypic heterogeneity. While single cell RNA-Seq is emerging as a high-dimensional and increasingly scalable tool for assessing phenotypic heterogeneity, many aspects of cellular phenotype cannot be inferred from the transcriptome alone. However, high-content imaging by microscopy could greatly expand the space of observables in a single cell analysis, particularly if it can be integrated with single cell RNA-Seq. High-content imaging assays using optical microscopy provide access to numerous phenotypic observables for cellular metabolism, protein localization, protein synthesis, cell cycle states, and cell signaling all with single cell resolution. However, existing tools for merging single cell imaging and sequencing are expensive, low-throughput, and incompatible with short-term cell culture and stimulation. The instant disclosure addresses this issue by combining a highly scalable microfluidic platform for single cell RNA-Seq and imaging with associated methodologies that allow for the association of sequence barcodes for inexpensive pooled library preparation with optical barcodes in devices described herein.

SUMMARY

The disclosure allows for devices, systems, and methods relating to genome-wide profiling of RNA from hundreds to thousands of individual cells in parallel for only a few cents per cell. The devices, systems, and methods described herein address the scalability problem of parallel preparation of low-input single cell libraries for RNA sequencing. Devices, systems, and methods described herein allow for parallel RNA profiling of individual cells in a device that is compatible with short term cell culture, drug stimulation experiments, and high-content fluorescence imaging. In an aspect, this is because the cells are physically segregated into microwells but still in sufficiently close proximity to communicate via diffusible factors.

In an aspect, the disclosure provides for a device or system comprising
 (a) one or more mRNA capture beads;
 (b) one or more cell-identifying optical barcodes;
 (c) a plurality of chambers, microchambers, or microwells comprising one or more mRNA capture beads and/or one or more cell-identifying optical barcodes; and
 (d) wherein the plurality of chambers, microchambers, or microwells comprising one or more mRNA capture beads and/or one or more cell-identifying optical barcodes are configured for reversible sealing.

In an aspect, the disclosure provides for a method of drug discovery, drug profiling, and/or drug testing comprising
 (a) combining one or more mRNA capture beads with one or more cell-identifying optical barcodes;
 (b) adding one or more mRNA capture beads with one or more cell-identifying optical barcodes to a plurality of chambers, microchambers, or microwells;
 (c) wherein the plurality of chambers, microchambers, or microwells including one or more mRNA capture beads and one or more cell-identifying barcodes are configured for reversible sealing; and
 (d) adding one or more drugs to the plurality of chambers, microchambers, or microwells configured for reversible sealing; and
 (e) adding one or more cells to the plurality of chambers, microchambers, or microwells that are configured for reversible sealing.

In an aspect, the one or more optical barcodes include one or more optical barcode sequences. In another aspect, the one or more optical barcodes include one or more fluorescent dyes including different colors and/or intensities.

The disclosure further provides for method of drug discovery, drug profiling, and/or drug testing described herein comprising (f) adding a buffer to the plurality of chambers, microchambers, or microwells configured for reversible sealing. In an aspect, the buffer includes a lysis buffer.

The disclosure further provides for a method of drug discovery, drug profiling, and/or drug testing comprising analyzing said cell-identifying optical barcode sequences by fluorescence.

In another aspect, the device or system of described herein comprise a plurality of chambers, microchambers, or microwells attached to a polysiloxane substrate. In yet another aspect, said polysiloxane substrate comprises polydimethylsiloxane.

In another aspect, the device or system described herein comprise cell-identifying optical barcode sequences are adapted for fluorescence detection.

In yet another aspect, the device, system, or methods comprise cells and said cells are not arranged in a droplet configuration.

In another aspect, the disclosure provides for a method for single cell RNA capture and sequencing, wherein said method comprises
 (a) introducing at least one cell into a microwell, wherein the microwell is attached to a first substrate that faces a second substrate and wherein oligo primers are attached to the surface of said second substrate;
 (b) hybridizing mRNA molecules to the surface of said second substrate;
 (c) adding at least one buffer to the microwell; and
 (d) contacting said first substrate with said second substrate, thereby creating a seal between said first substrate and said second substrate.

In yet another aspect, the disclosure provides for a device for single cell RNA capture and sequencing, wherein said device comprises a plurality of microwells; wherein said plurality of microwells are attached to a first polysiloxane substrate; a second substrate comprising glass that faces said first substrate, wherein oligo primers are grafted onto to the glass surface of said second substrate.

The disclosure further provides for a microwell comprising a composition comprising one or more mRNA capture beads; one or more cell-identifying optical barcode sequences; one or more cells, one of more buffers.

In another aspect, the disclosure provides for a plurality of dual barcode oligonucleotide capture beads, each capture bead comprising a first and a second plurality of oligonucleotide sequences separately attached to an outer surface of the capture bead, wherein the first plurality is an oligonucleotide sequence comprising:

(a) a PCR handle attached to each capture bead, wherein the PCR handle is identical in each oligonucleotide sequence on each capture bead;
(b) a first barcode attached to the PCR handle, wherein the first barcode is identical for all oligonucleotide sequences attached to the same capture bead, and wherein the first barcode differs for each capture bead;
(c) a unique molecular identifier (UMI) of length 6 to 16 nucleotides (nt) attached to the barcode, wherein the UMI may differ between oligonucleotide sequences on the capture bead, wherein the UMI may differ between different capture beads; and
(d) an oligo(dT) attached to the UMI;

wherein the second plurality is an oligonucleotide sequence comprising (a), (b), (c), (d) and a second barcode attached to the oligo(dT), wherein the second plurality of oligonucleotide sequences represents 0.1% to 10% of attached oligonucleotide sequences.

In an embodiment, the second barcode is configured to identify a cell associated with the capture bead, and to identify the first barcode. Preferably, the second barcode is configured to be read by fluorescence hybridization.

In an embodiment of the dual barcode bead, the UMI is of length 6 nucleotides (nt) to 10 nt, or the UMI length may be 6 nt. In an embodiment the second barcode is of length 8 nt to 30 nt, or of length 8 nt to 15 nt, or of length 8 nt. Preferably, the dual barcode capture bead is in the form of a plurality of capture beads.

In another embodiment, the disclosure provides for a plurality of merged barcode oligonucleotide capture beads, each capture bead comprising a plurality of oligonucleotide sequences separately attached to an outer surface of the capture bead, wherein each oligonucleotide sequence comprises:

(a) a PCR handle attached to each capture bead, wherein the PCR handle is identical in each oligonucleotide sequence on each capture bead;
(b) a barcode attached to the PCR handle, wherein the barcode is configured for identification of the attached capture bead and associated cell, wherein the barcode comprises N blocks, wherein each block is an oligonucleotide sequence of length 8 nt to 30 nt chosen from one of N sets of M oligonucleotides, wherein N is at least 2 and M is at least 30;
(c) a unique molecular identifier (UMI) of length 6 to 16 nucleotides (nt), wherein the UMI is either (i) attached to the barcode or (ii) segments of the UMI appear before or between or after the blocks of oligonucleotides, wherein the UMI may differ between oligonucleotide sequences on the capture bead, and wherein the UMI may differ between different capture beads; and
(d) an oligo(dT) attached to the UMI.

The variable N represents the number of blocks and an equivalent number of oligonucleotide sets containing M oligonucleotides. The number N of blocks/sets may be up to 4, 6, 8, 10, or more. A set of M oligonucleotides may have up to 200, 300, 400, or more oligonucleotides. In an embodiment of the merged barcode capture bead, N is 2 and M is 96. In another embodiment, the UMI is of length 6 nt to 10 nt, or the UMI is of length 6 nt. In another embodiment, the identification of the attached capture bead is by on-bead sequential fluorescence hybridization or on-bead sequencing.

In another embodiment, the disclosure provides for a method for single cell RNA capture and sequencing, wherein the method comprises (a) introducing into a microwell a cell and an oligonucleotide capture bead, wherein the microwell is formed from a first substrate that faces a second substrate; and (b) adding at least one buffer to the microwell. The first substrate and second substrate may be unitary in structure. In an embodiment, the capture beads are dual barcode or merged barcode capture beads. In another embodiment of this method, the first and/or second substrate is a polysiloxane substrate. In another embodiment the first and/or second substrate is polydimethylsiloxane (PDMS). The method may also include another step (e) analyzing the sealed first substrate and second substrate by microscopy or fluorescence, preferably on-bead microscopy or on-bead fluorescence. Preferably, the buffer comprises a lysis buffer.

In another embodiment, the disclosure provides a device for single cell RNA capture and sequencing, wherein said device comprises (a) a plurality of capture beads, (b) a first substrate comprising a plurality of microwells, and (c) a second substrate that faces said first substrate. In an embodiment of the device, the first and/or second substrates are polysiloxane substrates. In another embodiment, the first and/or second substrates are PDMS substrates. In another embodiment, the capture beads are dual barcode or merged barcode capture beads. In another embodiment of the device, individual capture beads are distributed in individual microwells.

BRIEF DESCRIPTION OF THE FIGURES

(FIG. 2A) For mRNA capture on polymer beads, the microwell array is fabricated in a thin PDMS layer on top of a glass slide or coverslip with a microfluidic flow channel above. Cells are first deposited in the microwell array by gravity followed by beads (while circles) covalently functionalized with oligo(dT) primers (orange circular outlines). A lysis buffer is introduced followed by rapid displacement of fluid in the channel with oil, which conformally seals the array. Single cell lysates (green) become trapped in individual microwells and mRNA hybridizes to the oligo(dT) on the beads (red circular outlines).

As illustrated in FIG. 3A, beads are first attached to a set of barcoded oligonucleotides in a multi-well plate, pooled into a single tube, and then re-distributed into a second multi-well plate for combinatorial addition of a second barcode sequence and capture site (oligo(dT)). FIG. 3B provides for detailed molecular biology for solid-phase, combinatorial barcode synthesis. A first barcode sequence is copied onto a dual-biotinylated oligonucleotide containing the T7 promoter sequence and a partial Illumina adapter using DNA polymerase. The resulting double-stranded DNA is conjugated to streptavidin-coated beads, and the non-biotinylated strand is removed. After pooling and expanding the beads, a second reaction is used to add a second barcode sequence and oligo(dT) by priming off of a universal anchor sequence that follows the first barcode.

As shown in FIG. 4A, cells are first deposited in the microwell array by gravity. The glass surface opposite the microwell array is covalently functionalized with oligo(dT) primers for mRNA capture (orange line). The device is then rapidly and conformally sealed against a glass surface in the presence of lysis buffer, flipped over, and held in a sealed position using negative pressure. Single cell lysates (green) become trapped in the sealed microwells, and mRNA hybridizes to the oligo(dT) primers on the glass surface, resulting in single cell mRNA "prints" (red lines). As shown by FIG. 4B an array of single cell mRNA prints on a glass coverslip generated using the device in FIG. 4A and imaged after on-chip reverse transcription. The double-stranded RNA/DNA hybrids are stained with SYTOX Orange, an intercalator dye and imaged on the glass surface. >96% of the prints result from individual cells. Note that the bright spots in the image that are not registered with the array originate from genomic DNA aggregates that were not fully removed by DNase digestion. FIG. 4C shows close-up images of single cell RNA printing. The left-most panel is a bright field image of three cells in individual microwells of the array, the middle panel is a fluorescence image of the corresponding RNA prints on the glass surface after reverse transcription and staining with SYTOX Orange, and the right-most panel is a fluorescence image of the glass surface after RNase digestion, demonstrating that the fluorescent prints originate from captured RNA.

FIGS. 5A-5C provide for an example flow cell device for single cell RNA-Seq. (A) Graphical representation of our five-lane microwell array flow cell device for single cell RNA-Seq. FIG. 5B shows a schematic of on-chip steps for single cell RNA-Seq. After depositing cells, barcoded capture beads (barcode sequences represented as different colors), and sealing as in FIG. 2A, single cell lysates (green) are trapped in individual microwells and mRNA hybridizes to the barcoded capture beads. The device is unsealed and rapidly washed by flow before on-chip, solid-phase reverse transcription and second-strand synthesis followed by elution and pre-amplification of the pooled library by in vitro transcription. FIG. 5C shows a montage of fluorescence images from part of one lane of the device in FIG. 5A showing beads (red) and cells (blue) loaded in the array. Note that this image was acquired following cell lysis while the device is sealed, and so the blue live stain fills the entire volume of the corresponding microwell and is confined to the microwell by sealing.

FIG. 6A shows a gene body distribution for uniquely mapped reads showing that we are primarily sequencing the 3'-end of transcripts, as expected. FIG. 6B shows a histogram of the number of genes detected per cell for the 396 single cell profiles used in all subsequent analysis of Experiment 1 and 247 single cell profiles used in all subsequent analysis of Experiment 2.

FIG. 7B provides for the same as FIG. 7A, but for single cell profiles in the MCF10a-exlusive lane. As shown in FIG. 7C, differential expression analysis was conducted to obtain cell type-specific gene sets for the U87 and MCF10a cells based on single cell profiles from the pure-cell lanes. Here, we show a histogram of log-ratio of the coefficients of variation (CVs) for the cell type-specific gene sets between the mixed lane profiles and the profiles from the respective pure lanes. As expected, the heterogeneity given by CV is greater for cells in the mixed lanes than in the cell type-exclusive lanes for the cell type-specific genes.

FIG. 8A: iPAGE gene ontology/pathway analysis based on rank-ordering of differentially expressed genes using $+/-(1-p)$ where p is the p-value for differential expression between the U87- and MCF10a-exclusive lanes given by the Wilcoxin rank-sum test. Values are positive for genes more highly expressed in U87 and negative for genes more highly expressed in MCF10a. FIG. 8B: t-SNE clustering of 396 single cell profiles based on the differentially expressed genes color-coated by the lane-of-origin of each profile. Two clear spatial clusters form and each is predominantly associated with a specific cell type-exclusive lane. FIG. 8C shows the same t-SNE clustering shown in (FIG. 8B) but color-coated with a score indicating expression of the U87-specific genes vs. the MCF10a-specific genes. The score is based on the relative rank ordering of U87- and MCF10a-specific genes in each cell.

FIG. 14B shows the intensity distribution for the beads in one of the three fluorescence channels demonstrating our ability to separate the optical barcodes based on fluorescence intensity (in this case with five different intensity levels).

FIG. 15A shows work flow of the synthesis of dual-barcoded mRNA capture beads. FIG. 15B is a schematic illustration of oligo sequence composition on dual-barcoded mRNA capture beads (upper-right). FIG. 15C is a look-up table linking sequencing barcode sequence with optical barcode sequence.

FIG. 16A shows representative images from optical phenotyping of cells and from optical demultiplexing of beads. FIG. 16B is a histogram of bead intensity after each of the 12 rounds of probe hybridization. FIG. 16C is histogram of optical barcode sequence occurrences.

FIG. 17A is an illustration of the design of the automated reagent delivery and imaging system for optical demultiplexing. FIG. 17B illustrates optical demultiplexing work flow. Scale bar: 200 μm.

FIG. 18A is a histogram of the fraction of molecules uniquely aligned to the human transcriptome for a mixed species analysis including human U87 and mouse 3T3 cells. FIG. 18B is a histogram of the number of uniquely aligned molecules per cell. FIG. 18C is a histogram of the genes detected per cell. FIG. 18D is a chart of the number of molecules detected (bottom-left) per cell as a function of the fraction of uniquely aligned reads sampled. FIG. 18E is a chart of the number of genes detected (bottom-right) per cell as a function of the fraction of uniquely aligned reads sampled.

FIG. 26 is a color image produced by merging the monochrome images of the same field of view in bright field, Cy3, and Cy5 channels.

DETAILED DESCRIPTION

Figure 1A:
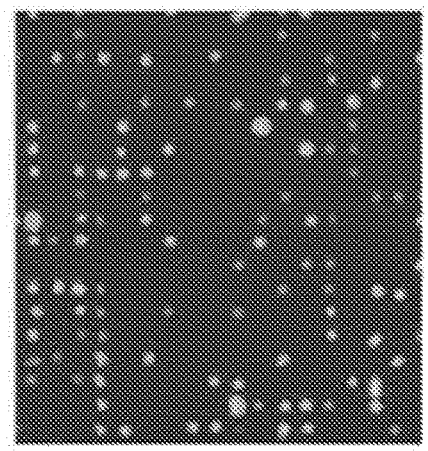
FIG. 1A provides for fluorescence imaging of a microwell array loaded with optically barcoded beads after introduction and hybridization of a single optical barcode probe. The brighter beads contain optical barcode oligonucleotides that are complimentary to the probe.

In an aspect, the disclosure provides for a microwell array system, devices, and methods for pairing individual cells with mRNA capture beads. In another aspect, the disclosure provides for a microwell array system, device, and methods for pairing individual cells with mRNA capture beads that introduce, cell-identifying barcode sequences into cDNA generated after mRNA capture. In an aspect, the system is compatible with high-content cellular imaging and drug stimulation experiments.

The disclosure further provides for capture beads, for example mRNA capture beads, or probes comprising one or more optical barcodes described herein. In an aspect, the capture beads, for example mRNA capture beads, or probes are used to identify drug and/or to be used in drug simulation experiments.

In an aspect, the disclosure provides for devices, systems, and/or methods wherein cells are arranged in a grid and/or a chamber. In yet another aspect, the disclosure provides for devices, systems, and/or methods wherein cells are arranged in a grid and/or chamber as compared to devices, systems, and/or methods wherein cells are arranged in droplets or a configuration where cells are physically segregated from one another. In an aspect, a microfluidic device, system, or method described herein comprises a flow cell with an array of microwells embedded in either the top or bottom of the device. In another aspect, the device described herein is a solid state device that allows for single cell isolation, imaging, and/or uniform parallel introduction of reagents to a plurality of cells.

The disclosure provides for devices, systems, and/or methods wherein cells are arranged in a reversible chamber or microchamber wherein the chamber and/or microchamber can be open and/or closed. The disclosure also provides for devices, systems, and/or methods wherein cells are arranged in reversible chamber or microchamber where the chamber and/or microchamber can be opened or closed as compared to devices, systems, and/or methods wherein cells are arranged in non-reversible droplets or a non-reversible configuration wherein cells are physically segregated from one another. In such a non-reversible configuration, the droplets and/or non-reversible configuration wherein cells are physically segregated cannot be readily toggled back and forth, that is, may not be opened or closed. As a result, in a non-reversible configuration, fluidics cannot be uniformly distributed to the cells and then uniformly removed and replaced by a second fluid.

The disclosure further provides for devices or system comprising
(a) one or more capture beads, for example mRNA capture beads;
(b) one or more cell-identifying barcode sequences, for example, optical barcode sequences;
(c) a plurality of chambers or microchambers including one or more mRNA capture beads and/or one or more cell-identifying barcode sequences;
(d) wherein the plurality of chambers or microchambers including one or more mRNA capture beads and/or one or more cell-identifying barcode sequences are reversible and are capable of being opened or closed more than a single time.

In an aspect, the disclosure provides for devices or system comprising
(a) one or more mRNA capture beads;
(b) one or more cell-identifying barcode sequences;
(c) a plurality of chambers or microchambers including one or more mRNA capture beads and/or one or more cell-identifying barcode sequences;
(d) wherein the plurality of chambers or microchambers including one or more mRNA capture beads and/or one or more cell-identifying barcode sequences are reversible and are capable of being opened or closed more than a single time; and
(e) wherein the device or system does not comprise a droplet microfluidics device or does not include droplet microfluidic technology, nonoliter droplet technology, and/or droplet sequence, "Drop-seq," "Drop-seq single cell analysis" technology, and/or technology wherein cells are captured in "droplets."

The disclosure further provides for probes comprising one or more mRNA capture beads and one or more cell-identifying barcode sequences associated or coupled with the one or more mRNA capture beads.

The disclosure further provides for compositions comprising one or more mRNA capture beads and one or more cell-identifying barcode sequences associated or coupled with the one or more mRNA capture beads and one or more cells.

The disclosure further provides for methods of drug discovery, drug profiling, and/or drug testing comprising
(a) combining one or more mRNA capture beads with one or more cell-identifying barcode sequences;
(b) adding one or more mRNA capture beads with one or more cell-identifying barcode sequences to a plurality of chambers or microchambers;
(c) wherein the plurality of chambers or microchambers including one or more mRNA capture beads and one or more cell-identifying barcode sequences are reversible; and
(d) adding one or more drugs to the reversible chambers or reversible microchambers.

The disclosure further provides for a probe comprising
(a) one or more mRNA capture beads;
(b) one or more cell-identifying barcode sequences, for example, optical barcode sequences;
(c) a plurality of chambers or microchambers including one or more mRNA capture beads and/or one or more cell-identifying barcode sequences;
(d) wherein the plurality of chambers or microchambers including one or more mRNA capture beads and/or one or more cell-identifying barcode sequences are reversible and are capable of being opened or closed more than a single time The disclosure further provides for methods for single cell RNA capture and sequencing, wherein said method comprises
(a) introducing at least one cell into a microwell, wherein the microwell is attached to a first substrate that faces a second substrate and wherein oligo primers are attached to the surface of said second substrate;
(b) hybridizing mRNA molecules to the surface of said second substrate;
(c) adding at least one buffer to the microwell;
(d) contacting said first substrate with said second substrate, thereby creating a seal between said first substrate and said second substrate.

In an aspect, the device, system, and/or microarray is imaged using fluorescence.

In another aspect, the disclosure provides for a device for single cell RNA capture and sequencing, wherein said device comprises a plurality of microwells; wherein said plurality of microwells are attached to a first polysiloxane substrate; a second substrate comprising glass that faces said first substrate, wherein oligo primers are grafted onto to the glass surface of said second substrate.

In an aspect, the substrate or surface comprises a polysiloxane substrate. In an aspect, the polysiloxane substrate comprises PDMS. In another aspect, the substrate comprises polymethylmethyacrylate (PMMA). In another aspect, the substrate comprises a thermoplastic for fabrication by, for example, hot embossing. In another aspect, the substrate comprises glass for fabrication by, for example laser machining. In another aspect, the substrate comprises silicon or silicon-on-glass or photoresist-on-silicon.

In another aspect, a system or device described herein further comprises one or more drugs, buffers, active agents, and/or a plurality of cells.

In an aspect, the disclosure provides for devices, systems, methods, and/or probes capable of profiling hundreds or thousands of cells from an organ or tumor. In an aspect, the cells analyzed are healthy human cells, abnormal cells, cancer cells, neural cells, immune cells, epithelial cells, mesenchymal cells, or stem cells. Cells could also originate from microorganisms including parasites, fungi, or bacteria. Other units containing nucleic acids such as viruses both in isolation or inside of an infected host cell could be analyzed.

In yet another aspect, different drugs or chemical constituents or compositions, for example, lysis buffer, may be introduced to a device or system described herein, for example, in a chamber or microchamber, at any time given the reversible nature of the chambers or microchambers. This provides for additional flexibility and advantages over other devices or systems, such as those employing, for example, droplet microfluidic technology, nanoliter droplet technology, and/or droplet sequence, "Drop-seq," "Drop-seq single cell analysis" technology, and/or technology where cells are captured in "droplets."

In an aspect, the device or system described herein, for example, the microfluidic device does not involve any on-chip valves and/or moving parts, which can result in a high feature density. In another aspect, the device or system described herein is not a droplet microfluidics device or does not include droplet microfluidic technology, nonoliter droplet technology, and/or droplet sequence, "Drop-seq," "Drop-seq single cell analysis" technology, and/or technology where cells are captured in "droplets." In an aspect, the device or system described herein is more compatible with cell culture and cell perturbation assays than a droplet microfluidic device because fluids can be readily exchanged in a uniform fashion and cells can communicate with each other via diffusible factors. Hence, cell viability will be higher and cells will exhibit normal physiology in comparison to cells that are sequestered in droplets. In another aspect, in the device or system described herein, cell are arranged in regular array and are in contact with a flat, optically transparent surface as opposed to a droplet microfluidic device in which cells are isolated inside of a spherical enclosure. Therefore, in yet another aspect, the device or system described herein is intrinsically more compatible with imaging, for example optical imaging or microscopy, than droplet devices.

In an aspect, devices, systems, and methods described herein have a higher throughput than devices, systems, or methods employing droplet microfluidic technology, nonoliter droplet technology, and/or droplet sequence, "Drop-seq," "Drop-seq single cell analysis" technology, and/or technology where cells are captured in "droplets." In yet another aspect, analysis of cells, probes, and beads using devices, systems, and methods described herein have a throughput that is 5, 10, 15, 20, 25, or 100 or more times less expensive than devices, systems, or methods employing droplet microfluidic technology, nonoliter droplet technology, and/or droplet sequence, "Drop-seq," "Drop-seq single cell analysis" technology, and/or technology were cells are captured in "droplets."

In another aspect, the device described herein is compatible with automation, for example, a computer-controlled system that is capable of facilitating automated introduction of any of various fluids to the device, temperature control, and reversible sealing of the microwells. Accordingly, in a preferred aspect the device described herein can capture mRNA from thousands of individual cells in parallel and produce pooled, single cell RNA-Seq libraries for ~$0.10/cell.

In an aspect, barcoded capture beads are introduced to the microwell array in either a random process or ordered process. In yet another aspect, barcoded capture beads are introduced into the microwell array in a random process with little or no control over which barcoded capture bead enter each microwell. Under such a scenario, in an aspect, imaging information acquired from the cells in the device is not directly associated with the single cell transcriptomes that ultimately are quantified by deep sequencing. In an aspect, this issue is addressed by introducing barcodes, for example, optical barcodes, to the mRNA capture beads that indicate the sequence barcode attached to each bead. In another aspect, the optical barcodes can be read out using the same or different fluorescence microscope used for live cell imaging on the device. In yet another aspect, the disclosure provides for a reagent that allows for the capture RNA from individual cells, allows for association of a unique sequence barcode with each single cell cDNA library, and/or reveals the identity of the attached sequence barcode by optical methods.

In an aspect, the disclosure provides for an optical barcode and associated methods described herein. In an aspect, the optical barcode is a sequence. In another aspect, the optical barcode is not a sequence. In another aspect, optical barcodes described herein are not DNA sequences.

In an aspect, an optical barcode described herein comprises a combination of fluorescent dyes comprising at least one different color and optionally more than one different intensity that make the bead uniquely identifiable on an optical microscope. In another aspect, an optical barcode described herein comprises a combination of fluorescent dyes comprising two, three, four, five or more different colors and optionally more than one different intensity that make a respective bead uniquely identifiable on an optical microscope.

The disclosure further provides for proteomic methods and systems utilizing a device, probe, or bead described herein. In an aspect, an oligonucleotide-based optical barcode is loaded onto beads that also harbor reactive groups for capturing protein (e.g. amine-, carboxyl-, or thiol-reactive groups). In yet another aspect, optical barcodes are loaded onto beads along with one or more antibodies capable of capturing specific proteins. Proteins can be quantified by fluorescence methods (e.g. fluorescently labeled antibodies) or mass spectrometry. In a further aspect, the disclosure provides for the use of DNA-labeled antibodies that are amplified, identified, and quantified by deep sequencing.

The devices, systems, and methods described herein provide for key distinctions and advantages over other devices, systems, and methods. For example, the microwell array device is constructed in such a way that it can be reversibly sealed during cell lysis and RNA capture. Significant loss of RNA occurs in our arrays when cells are lysed in unsealed or even imperfectly sealed arrays due to rapid diffusion of RNA molecules. In the context of the bead capture and RNA-Seq experiments, this could result not only in reduced RNA capture, but also significant cross-talk. Herein, advantage is taken of the physical properties of PDMS, namely its flexibility and hydrophobicity, for high-fidelity, reversible sealing which is difficult to achieve using the agarose hydrogel device reported previously. In addition, the devices, systems, and methods described herein demonstrate genome-wide single cell RNA-Seq. Additionally, the single cell capture and pooled library preparation scheme described herein costs $0.10-$0.20/cell even at a relatively modest scale of several hundred cells per run (see, for example, Table 7), compared to the <$1/cell estimated at the 10,000-cell scale for alternative approach, for example, one described in Fan H C, Fu G K, Fodor SPA: Combinatorial labeling of single cells for gene expression cytometry. Science 2015, 347:628-636, which is herein incorporated by reference in its entirety.

In an aspect, the disclosure provides for optical demultiplexing or optical barcoding of sequence-barcoded capture beads by, for example, attaching a unique combination of short oligonucleotides to each bead. In an aspect, while the sequence barcode associated with the RNA capture primer can be read out by DNA sequencing, the optical barcode can be read out on a standard fluorescence microscope. In another aspect, the oligonucleotide combination is unique to each sequence barcode and can be identified by hybridizing fluorescently labeled complementary oligonucleotides to beads. The presence or absence of a series of fluorescently labeled oligonucleotides on each bead after hybridization indicates the unique combination of short oligonucleotides attached to each bead and therefore the sequence barcode attached to each bead. Once the sequence barcode attached to each bead is identified, single cell transcriptome captured on each bead can be identified and read out using a sequencer with phenotypic information obtained from imaging the cells associated with each bead in each microwell of our device.

In an aspect, optical barcoding technology described herein is combined with applications beyond single cell RNA-Seq. In an aspect, an extension of the invention is bulk RNA-Seq or RNA-Seq of small numbers of cells. These can be seeded in the microwells or propagated from a single cell seeded in each microwell. The disclosure further provides for single cell DNA-Seq. The disclosure further provides for barcoded capture oligonucleotides that contain oligo(dT) for capturing mRNA from individual eukaryotic cells. Alternatively, the beads are functionalized with primers that are specific to targeted DNA loci or RNA transcripts. In yet another aspect, the beads are functionalized with primers that have a random sequence and can therefore capture any DNA or RNA sequence from an individual cell. In an aspect, in each case, a corresponding optical barcode is used to link imaging data acquired for a target cell or group of cells and sequencing data acquired from whatever nucleic acids are captured on the bead.

The disclosure further provides for proteomic methods and systems utilizing a device described herein. In an aspect, an oligonucleotide-based optical barcode is loaded onto beads that also harbor reactive groups for capturing protein (e.g. amine-, carboxyl-, or thiol-reactive groups). In yet another aspect, optical barcodes are loaded onto beads along with one or more antibodies capable of capturing specific proteins. Proteins can be quantified by fluorescence methods (e.g. fluorescently labeled antibodies) or mass spectrometry. In a further aspect, the disclosure provides for the use of DNA-labeled antibodies that are amplified, identified, and quantified by deep sequencing.

Single cell analysis is important for understanding how cells respond to drugs and other perturbations because phenotypic responses are inherently asynchronous.

PDMS Microwell Flow Cell for Single Cell Transcriptome Capture

In an aspect, the microfluidic platform described herein comprises a flow cell with an array of microwells embedded in either the top or bottom of the device. In an aspect, the device or system described herein comprises a high-throughput DNA sequencing and digital PCR device, as described in, for example, White A K, Vanlnsberghe M, Petriv Hamidi M, Sikorski D, Marra M A, Piret J, Aparicio S, Hansen C L: High-throughput microfluidic single-cell RT-qPCR. *Proceedings of the National Academy of Sciences of the U.S. Pat. No.* 2011, 108(34):13999-14004 or Men Y, Fu Y, Chen Z, Sims P A, Greenleaf W J, Huang Y: Digital polymerase chain reaction in an array of femtoliter polydimethylsiloxane microreactors. *Anal Chem* 2012, 84(10):4262-4266, the contents of which are incorporated by reference herein in their entirety.

In an aspect, fluids can be driven through the flow cell manually by, for example, laminar flow using a syringe or pipette. Fluid exchange in the microwells occurs by diffusion, while cells and beads can be loaded by gravity. The microwell arrays may be fabricated from, a polysiloxane substrate, for example, polydimethylsiloxane (PDMS), a silicone rubber commonly used in soft lithography. PDMS allows inexpensive, rapid, and repeatable fabrication from molds produced on silicon in photoresist using standard photolithography. See, for example, McDonald J C, Whitesides G M: Poly(dimethylsiloxane) as a material for fabricating microfluidic devices. *Accounts of chemical research* 2002, 35(7):491-499 and *First Single Cell Expression Analysis with PDMS*, Marcus et al., *Analytical Chemistry*, 2006. (Quake Lab), which are herein incorporated by reference in their entirety. In addition, the material properties of PDMS, including its hydrophobicity and flexibility, facilitate reversible sealing of the microwells against a flat surface using mechanical deformation and negative pressure (see, for example, FIG. 2A) or introduction of oil by laminar flow (See, for example, FIG. 3A).

In an aspect, the device or system described herein is capable of solid-phase capture of RNA from individual cells via two modes of operation—RNA "printing" on glass and RNA capture on beads. For example, in an aspect, in RNA printing mode, individual cells are loaded in the microwells, which are fabricated in a PDMS slab that faces a glass coverslip. Oligo(dT) primers are covalently grafted to the glass surface so that mature mRNA molecules can be immobilized by hybridization of their poly(A) tails. Following the introduction of lysis buffer, the microwells can be sealed by mechanically placing them in conformal contact with the functionalized glass surface. Cell lysis releases mRNA into the solution confined by the microwells, resulting in hybridization to the oligo(dT)-coated glass coverslip. By placing the flow channel under negative pressure, the seal can be maintained in the absence of mechanical force, making the device transportable and readily accessible to an optical microscope. See, for example, White A K, Vanlnsberghe M, Petriv O I, Hamidi M, Sikorski D, Marra M A, Piret J, Aparicio S, Hansen C L: High-throughput microfluidic single-cell RT-qPCR. *Proceedings of the National Academy of Sciences of the United States of America* 2011, 108(34):13999-14004, which is herein incorporated by reference in its entirety.

Because the mRNA is immobilized on a glass surface, enzymatic processing steps can take place on-chip, simply by sequential flow of reagents through the device. After incubating the trapped, single cell lysates with the glass capture surface, the seal may be released and the flow cell can be rinsed with a detergent-containing buffer followed by a reaction mixture containing DNase. Because the oligo(dT) primers are comprised of locked nucleic acid (LNA), they are resistant to nuclease digestion. See, for example, Koshkin A A, Nielsen P, Meldgaard M, Rajwanshi V K, Singh S K, Wengel J: LNA (locked nucleic acid): an RNA mimic forming exceedingly stable LNA: LNA duplexes. *Journal of the American Chemical Society* 1998, 120(50):13252-13253, the content of which is incorporated by reference in its entirety.

The immobilized single cell mRNA libraries can then be reverse transcribed in parallel, and the resulting mRNA/cDNA hybrids can be visualized by fluorescence microscopy after staining with a fluorogenic intercalator dye. For example, FIG. 4B illustrates a fluorescence image of single cell transcriptome "prints" arrayed on a glass coverslip as described above. Here, it is further confirmed by running a control experiment that the printed material originates from RNA. While some aggregates of genomic DNA were not fully digested (but are reduced in intensity by DNase treatment), the disclosure further confirms that the vast majority of material imaged in the circular prints originates from RNA. For example, the left-most panel of FIG. 4C shows a bright field image of a microwell array in which three microwells each contain an individual cell. The resulting RNA prints (middle panel) that can be visualized after reverse transcription are ablated by incubating the surface with RNaseH (right-most panel), which selectively digests RNA in RNA/DNA hybrids. Conversion of RNA/DNA hybrids to single-stranded cDNA precludes detection using the intercalator dye, and so removal of RNA from the prints eliminates the fluorescence signal almost completely. FIG. 4C also contains some small fluorescent objects associated with the interstitial walls of the microwell array or with microwells that did not contain a cell. These are substantially reduced in intensity by RNase treatment, confirming that they are, in fact, RNA that is spuriously captured or non-specifically absorbed. These objects could arise due to contamination from dead cells or other sources of freely floating RNA introduced with the cells prior to sealing.

Nonetheless, the vast majority of the observed signal in FIG. 4C is associated with the circular mRNA prints that correlate perfectly with microwells that initially contained a cell.

Figure 2B:
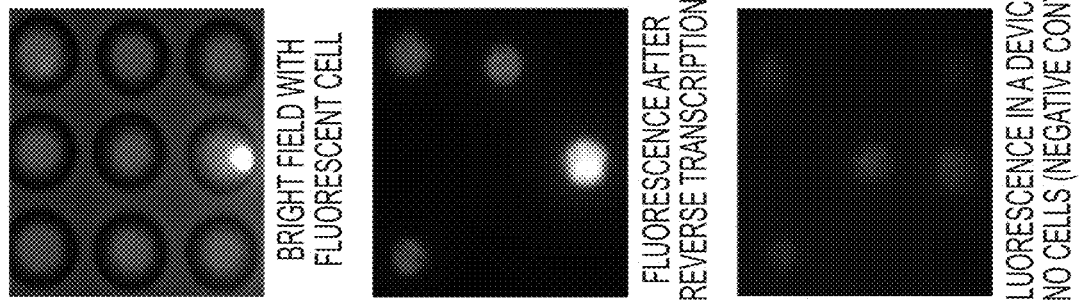
FIG. 2B contains images of single cell RNA capture on beads. The top panel is a bright field/fluorescence overlay of a microwell array in which four microwells contain a bead, but only one contains both a bead and a cell (fluorescently labeled with live stain). The middle panel is a fluorescence image of the array after RNA capture, reverse transcription, and staining with SYTOX Orange. Note that the bead associated with a cell is significantly brighter than the other beads. The bottom panel is a fluorescence image of beads in an array from a negative control experiment involving no RNA or cells, showing that the beads have a certain level of background fluorescence in the presence of stain, which explains the majority of the background signal observed in the beads with no cell in the middle panel.
Figure 4A:
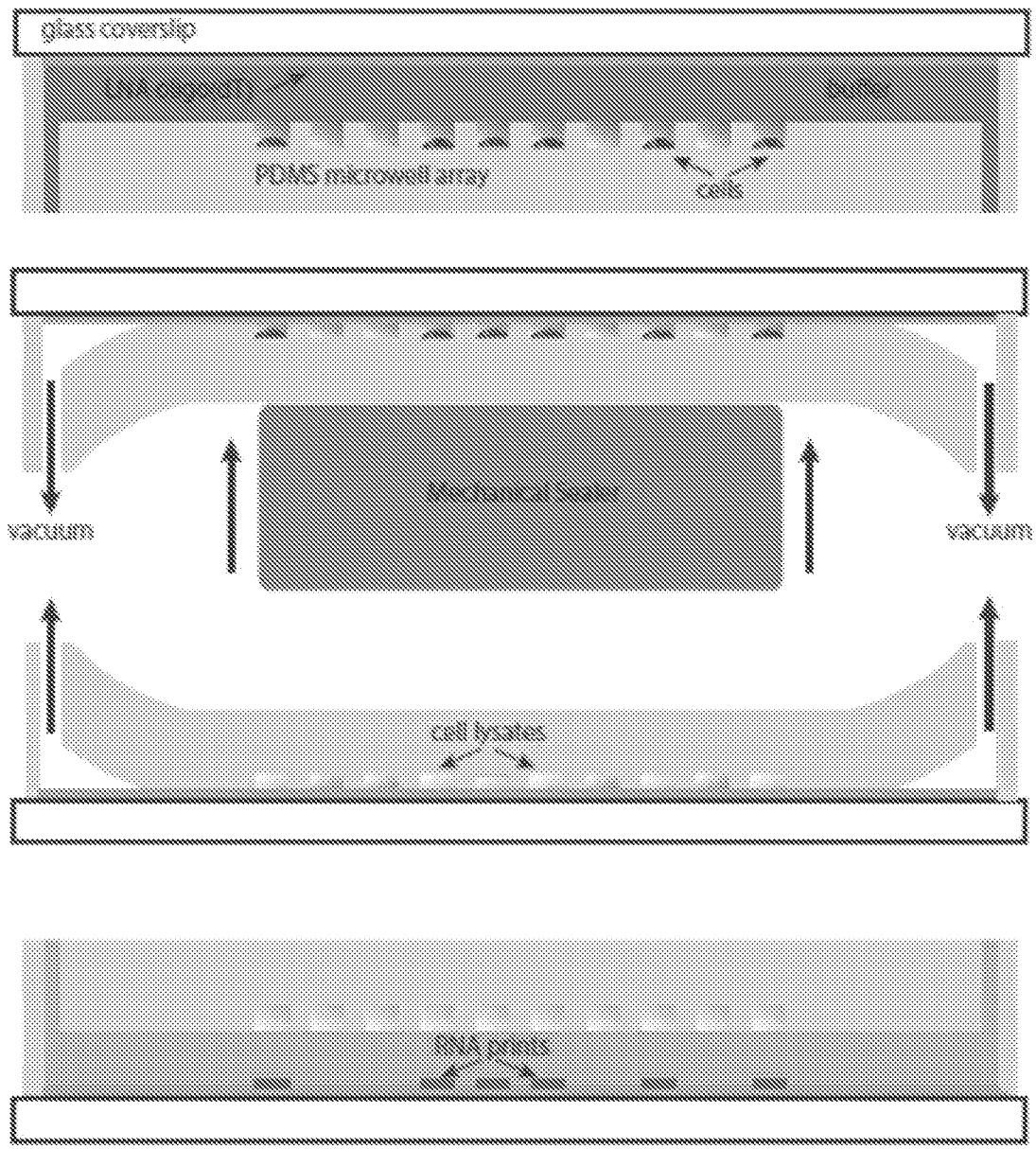
FIGS. 4A-4C provide for a schematic and fluorescence imaging data for single cell RNA printing.
Figure 4B:
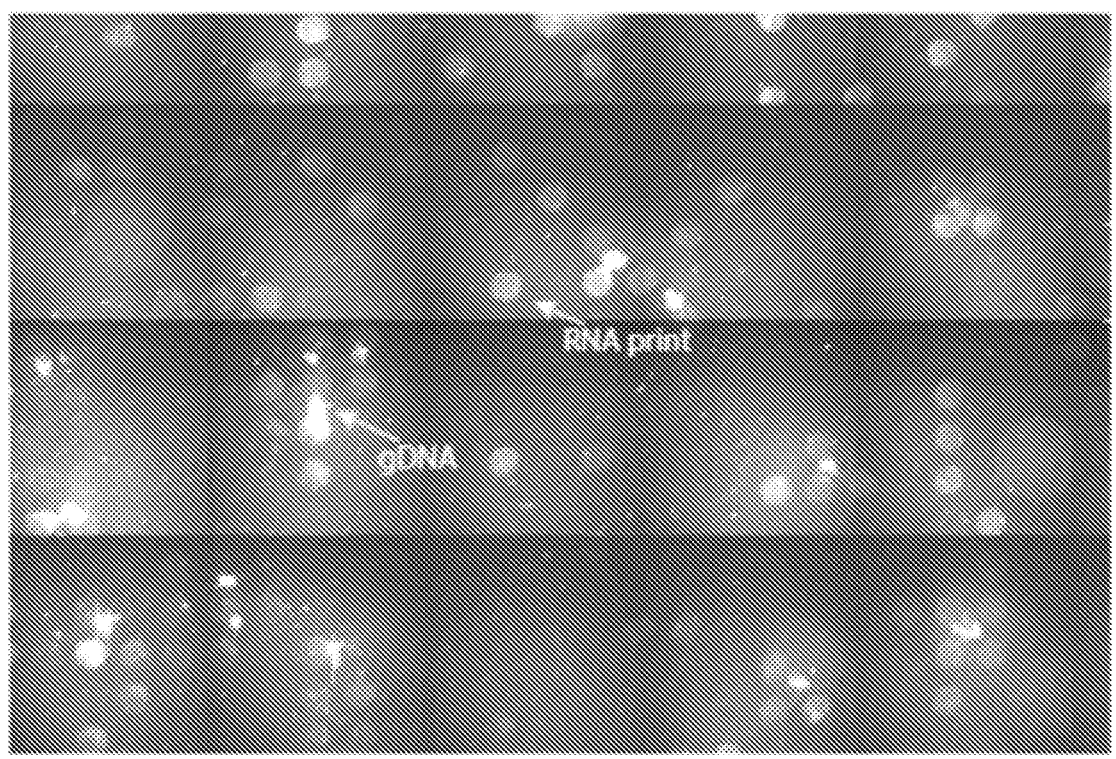
Figure 4C:
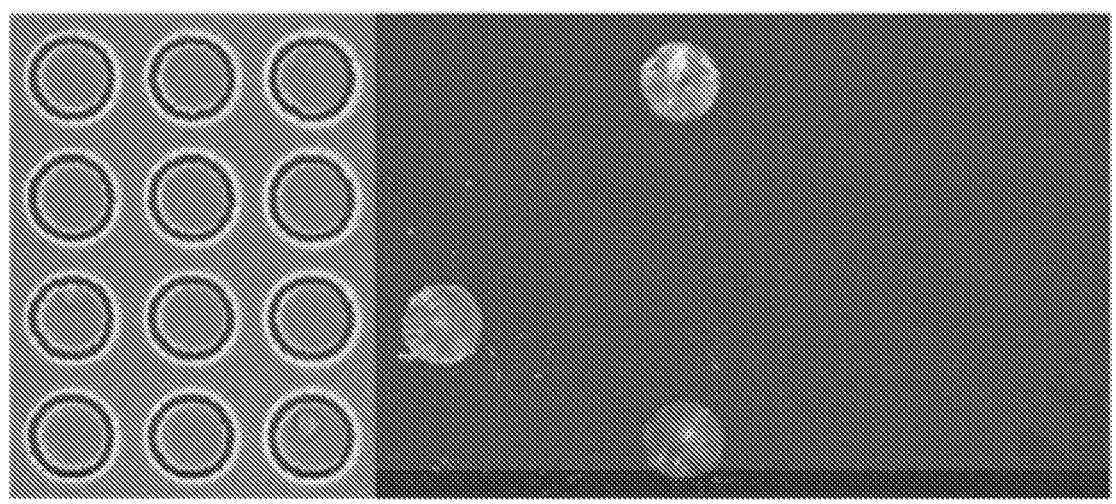

FIG. 4A shows a second, very similar version of the device where the microwells are fabricated in PDMS on a glass slide, and the sealing is accomplished by laminar flow of oil. Using nearly the same procedures as described above for RNA printing mode, we use this version of the device to capture RNA on beads. After introducing cells, we can load beads into the microwells by gravity and achieve super-Poisson loading by using beads with a mean diameter greater than the radius of the microwells. Like the glass surface in FIG. 4A, we coat the beads in oligo(dT) to facilitate mRNA capture after cell lysis and sealing. FIG. 2B shows bright field and fluorescence images of a bead-containing microwell array loaded with individual cells following solid-phase mRNA capture and reverse transcription. The bead contained in a microwell that also contains a cell is substantially more fluorescent following reverse transcription than the other beads. While there is some fluorescence signal associated with beads that do not contain a cell, this is mainly due to non-specific staining of the high-density of single-stranded primers on the bead surface and non-specific staining of the bead itself, as shown in the third panel of FIG. 2B where we depict fluorescence images of beads in the absence of cells, cell lysate, or RNA as a negative control.

A Scalable Platform for Single Cell RNA-Seq

A scalable platform for single cell RNA-Seq based on the bead capture modality is described herein. The low reagent volumes required for microfluidic processing result in a significant cost reduction relative to some conventional methods, for example, as described in Wu A R, Neff N F, Kalisky T, Dalerba P, Treutlein B, Rothenberg M E, Mburu F M, Mantalas G L, Sim S, Clarke M F et al: Quantitative assessment of single-cell RNA-sequencing methods. *Nat Methods* 2014, 11(1):41-46, which is herein incorporated by reference in its entirety.

A further reduction in cost can be realized by, for example, using microfluidics in combination with schemes for cDNA barcoding. A representative example of this, such as the CEL-Seq strategy, can be found in Hashimshony T, Wagner F, Sher N, Yanai I: CEL-Seq: single-cell RNA-Seq by multiplexed linear amplification. *Cell Rep* 2012, 2(3): 666-673, which is herein incorporated by reference in its entirety. By introducing a cell-specific barcode to the cDNA during reverse transcription, all subsequent sequencing library preparation steps can be accomplished on pooled cDNA from multiple cells, further reducing hands-on time and reagent consumption.

Figure 3A:
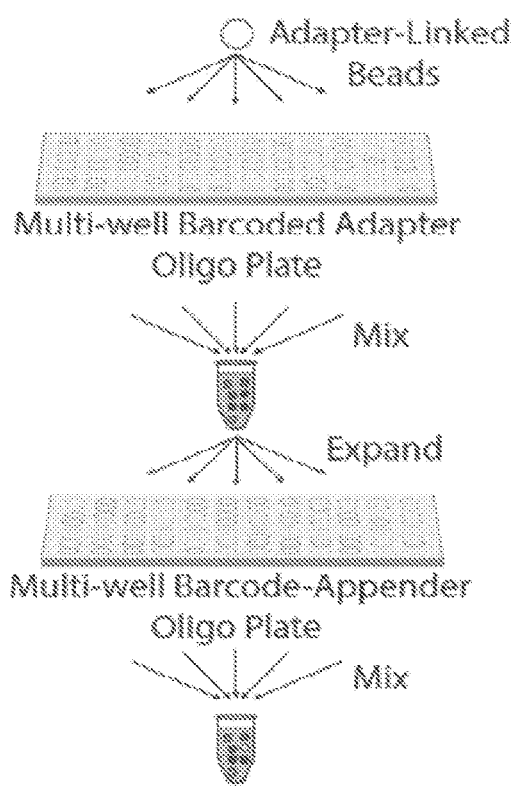
FIGS. 3A and 3B provide for combinatorial scheme for synthesis of barcoded capture beads.
Figure 3B:
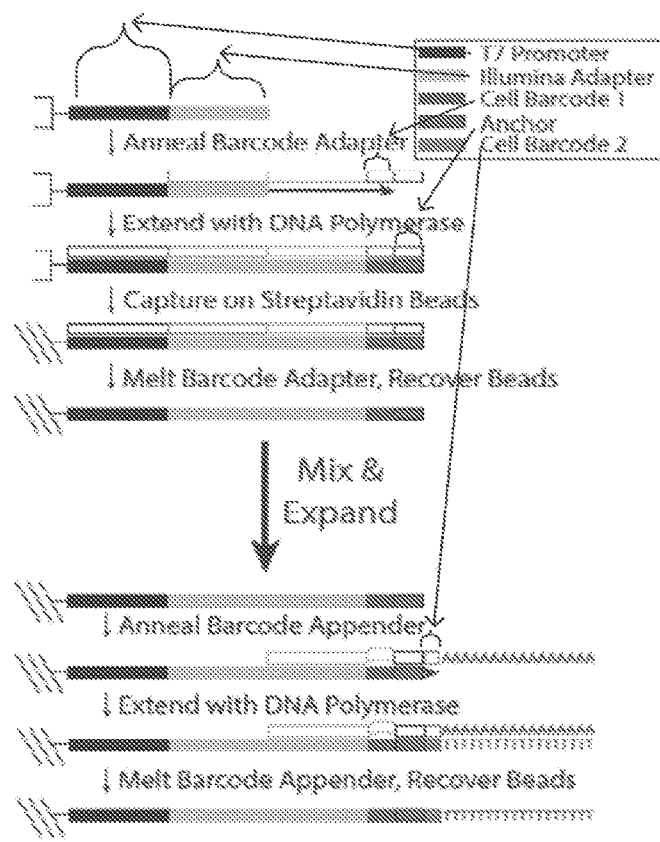

A pool of mRNA capture beads was generated in which each bead is attached to ~1 billion copies of a primer terminated on the 3'-end with one of 960 possible barcode sequences followed by oligo(dT) using a combinatorial synthesis technique (FIGS. 3A and 3B). If, for example, 100 cells loaded into the microwells of a device or system described herein receive a random barcoded bead from the pool, it is expected that the mRNA from ~95 of them would be uniquely labeled based on the binomial distribution. A copy of the T7 promoter sequence (TPS) and part of an Illumina sequencing adapter (ISA) comprise the 5'-end of the capture primer (Table 1) to allow linear pre-amplification by in vitro transcription (IVT) and library enrichment by PCR (FIG. 3B). To create this large pool of barcoded beads, 96 different barcode-containing oligonucleotides (Table 2) were copies onto a dual-biotinylated oligonucleotide containing TPS and ISA by primer extension with DNA polymerase in a 96-well plate. Each barcode is terminated with a universal, 6-base anchor sequence that becomes the 3'-end of the biotinylated oligonucleotide after the first round of primer extension (FIG. 3B). After this first reaction, each barcoded oligonucleotide was immobilized onto a set of streptavidin-coated Sepharose beads, quench the reaction, combine all of the barcoded beads in a pool, and remove original barcode-containing strand by denaturation. At this point, the pool of beads is split into ten new reactions and each containing one of ten unique second barcodes along with poly(dT) (Table 3) are added to the 3'-end of the immobilized oligonucleotide by primer extension from the universal anchor sequence (FIG. 3B). After quenching this reaction, the beads can be pooled, removing the unbiotinylated strands, and washed. The resulting pool of beads contains 960 barcoded capture primers.

A PDMS microwell device containing five flow channel lanes for physical multiplexing of samples and >10,000 microwells was constructed (FIG. 5A). The cylindrical microwells are about 50 μm in diameter and height with a volume of <100 pL. In another aspect, the microwells are about 100 μm to about 5 mm, about 5 μm to about 200 μm, about 10 μm to about 100 μm, about 25 μm to about 75 μm, about 30 μm to about 600 μm in diameter and height. In yet another aspect, the microwells comprise a volume of about 10 pL to about pL, about 10 pL to about 100 pL, about 25 pL to about 75 pL, about 25 pL to about 100 pL. In an aspect, cells are loaded in individual microwells randomly, according to Poisson statistics, such that the majority of cell-containing wells contain one cell. The concentration of the cellular suspension can be tuned in order to avoid overloading the microwell array. For example, if ~100 cells are captured in every 1,000 microwells of a given array, then about <5% of microwells will contain more than one cell. Beads can then be loaded into the wells at a somewhat higher density because the mean diameter of the beads (~30 μm) significantly reduces the probability double-loading (FIG. 5B and FIG. 5C). In an aspect, depending on the size of the microwell, it is rare to observe both beads and cells in an overloaded microwell. Given the pool of 960 cell-identifying barcodes and five lanes, the capacity of the system described herein for single cell RNA-Seq is ~600 cells at a unique barcoding rate of >94%. In another aspect, the capacity of the system described herein for single cell RNA-Seq is ~600 cells at a unique barcoding rate of about greater than 85%, greater than 90%, greater than 91%, greater than 92%, greater than 93%, greater than 94%, greater than 95% or more. In an aspect, the device or systems described herein may be scaled to increase capacity by synthesizing additional barcodes and/or adding microwells to the device or system.

After loading the cells and barcoded beads, procedures described above and herein can be employed to trap single cell lysates in sealed microwells, immobilizing captured mRNA on beads, and reverse transcribe (FIG. 5B). Following on-chip second-strand synthesis, the pool of single cell libraries can be simultaneously elute and pre-amplify overnight by IVT using T7 RNA polymerase (FIG. 5B). The resulting amplified RNA (aRNA) can be removed from each lane using a pipette, reverse transcribe the aRNA from each lane with primers containing lane-identifying barcodes, the cDNA libraries from all five lanes can be pooled, and enrichment of the sequencing library in a single PCR reaction can be undertaken. The primers used for aRNA reverse transcription contain 8-base unique molecular identifiers (UMIs) so that the vast majority of cDNA molecules are distinguishable. That way, genes can be quantified from sequencing data based on the number of UMIs associated with each gene rather than the number of reads, mitigating noise and bias that result from exponential amplification by PCR. See, for example, Shiroguchi K, Jia T Z, Sims P A, Xie X S: Digital RNA sequencing minimizes sequence-dependent bias and amplification noise with optimized single-molecule barcodes. *Proceedings of the National Academy of Sciences* 2012, 109(4):1347-1352 and Shiroguchi K, Jia T Z, Sims P A, Xie X S: Digital RNA sequencing minimizes sequence-dependent bias and amplification noise with optimized single-molecule barcodes. *Proceedings of the National Academy of Sciences* 2012, 109(4):1347-1352, which are incorporated by reference in their entirety.

Demonstration and Analysis of Highly Multiplexed Single Cell RNA-Seq

In an aspect, the microfluidic device described herein is used to obtain RNA-Seq profiles from ~600 cells across five lanes from two commonly used human cancer cell lines (described herein as "Experiment 1" throughout the text). One of the five lanes contained U87 human glioma cells, one contained MCF10a human breast cancer cells, and the other three contained a mixture of both cell lines. These two cell lines are highly mesenchymal, have been cultured for numerous passages, and have relatively similar expression profiles. Nonetheless, they are distinguishable by a few key genes and can be readily separated the data set. In addition, in an aspect, a slightly different protocol with less expensive reagents are used to obtain profiles of ~500 cells across five lanes for a different cell pair (U87 cells and the diploid cell line WI-38, which has not undergone malignant transformation) in Experiment 2.

A factor with any pooled library scheme is cross-talk between cell-identifying barcodes. As described herein, this issue is addressed by quantitative analysis of Experiment 1. For example, the disclosure provides for methodology wherein cross-talk is quantified by using both sequencing and imaging data. In an aspect, because the device or system described herein is compatible with fluorescence microscopy, a fraction of the streptavidin molecules on each bead can be labelled with red-fluorescent AlexaFluor 647 and pre-stained the cells with a blue-excitable live stain. This allows quantification of the number of cells paired with a barcoded capture bead and also allows for the estimation of the number of barcodes that are expected to be observed in the sequencing data for each lane. The sequencing data reveals that more barcodes are present in the library for each lane than expected based on the imaging data. Analysis reveals that the number of molecules associated with a given barcode placed the barcodes in two distinct populations. The size of the population of barcodes associated with a larger number of molecules was highly consistent with the imaging data (within −8%), which we take to demarcate our single cell RNA-Seq profiles. The second, larger population of barcodes with relatively few associated molecules likely results from multiple potential sources including sequencing error, actual cross-talk or spurious capture within our microfluidic device, and PCR jumping as observed in other implementations of multiplex single cell RNA-Seq. Across all five lanes the cell-identifying barcodes that were not associated with actual cells in the device had 200-300×fewer molecules per barcode than those associated with cells (based on the ratio of median unique molecules in the two populations).

Figure 6A:
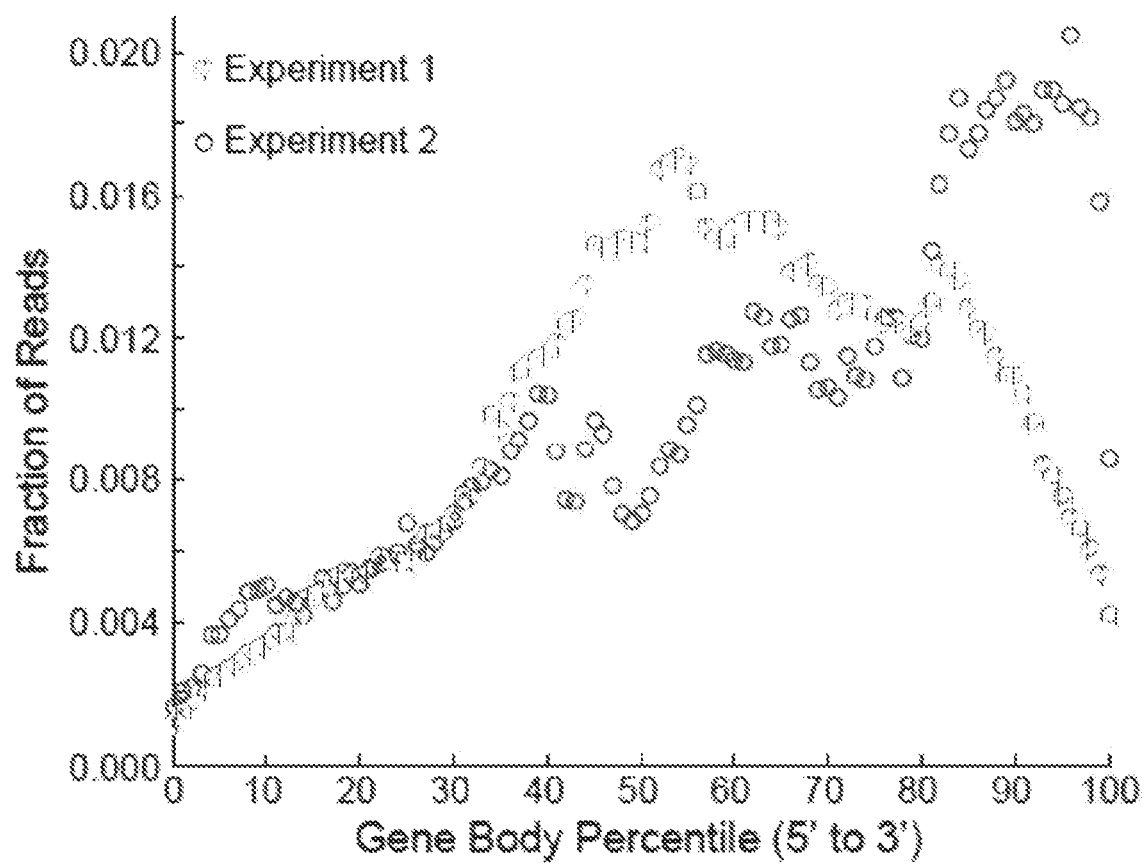
FIGS. 6A and 6B show an analysis of single cell RNA-Seq data.
Figure 6B:
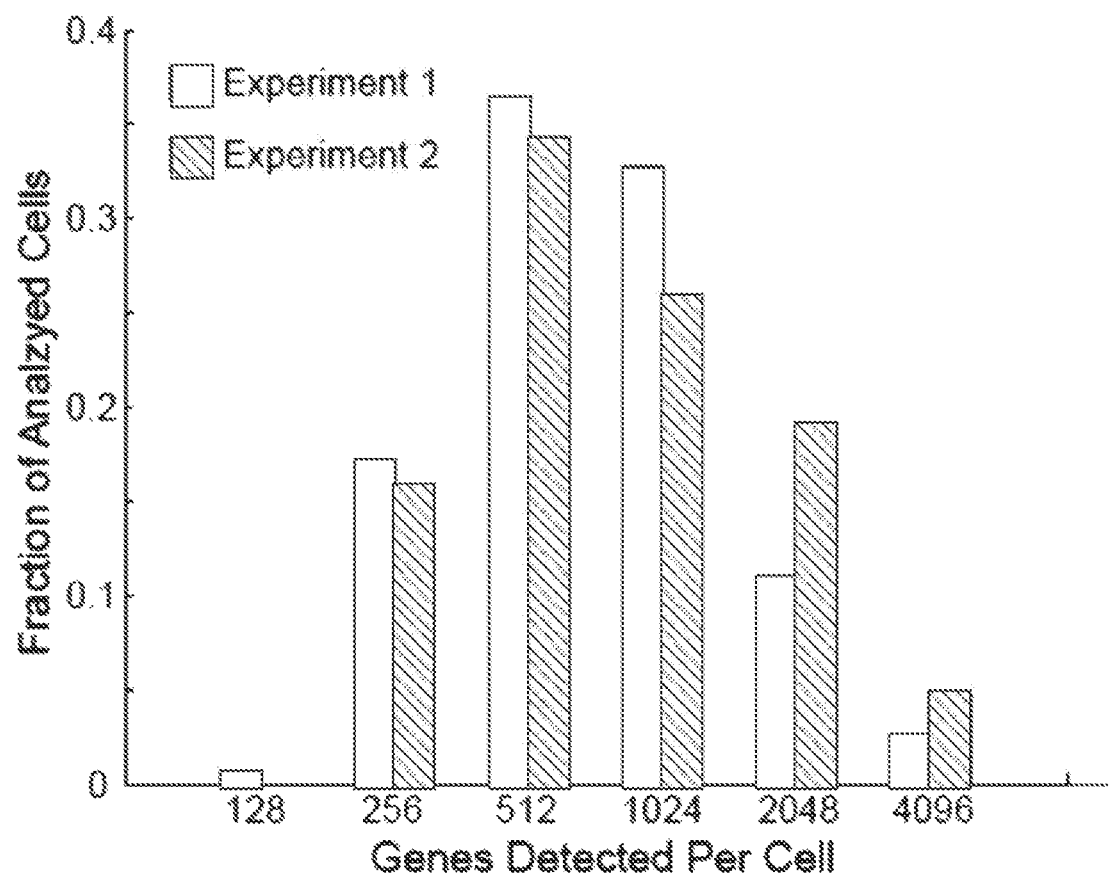

As described in FIGS. 6A and 6B, the systems and devices described herein produce useful single cell RNA-Seq profiles. For example, in an aspect, the library preparation protocol described herein is based on CEL-Seq where, rather than sequencing the full gene body and normalizing by transcript length, the 3'-end of transcripts are sequenced and counted. FIGS. 6A and 6B show the expected distribution of mapping positions for 3'-end sequencing, with most reads mapping to the 3'-UTRs or coding sequences. Subsequent analysis to demonstrate cell type separation using our data set will rely on the 396 single cell profiles that we obtained with the highest coverage. Although 635 genes on average were detected across all cell profiled in Experiment 1, an average of 876 genes from the top 396 cells were detected (FIG. 6B). Hence, the 204 cells that we discard from subsequent analysis have an average of ~170 genes detected per cell. Similarly, for Experiment 2, an average of 1,030 genes from the top 247 single cell profiles were detected, but 18 530 genes on average across all cells.

Figure 7A:
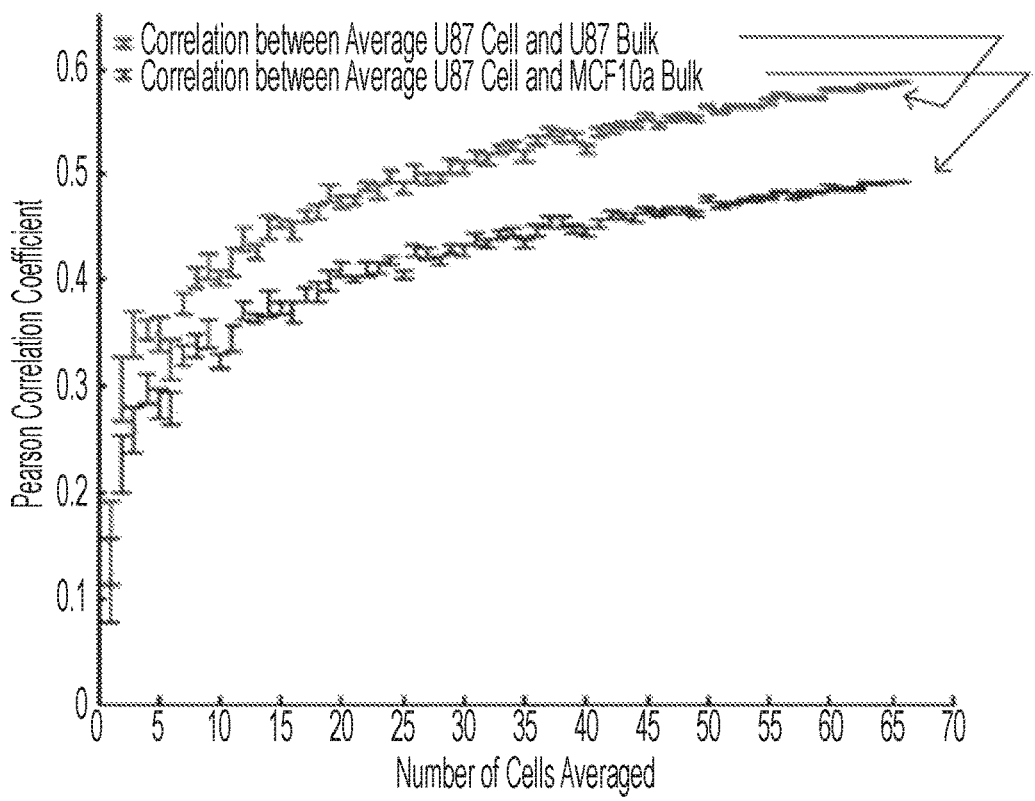
FIGS. 7A-7C provide for (FIG. 7A) a comparison of single cell median and population-level RNA-Seq profiles for cells originating from the U87-exclusive lane in Experiment 1. Each data point was obtained by constructing a median profile from a given number of cells and repeating this ten times by random sampling with replacement to obtain a median Pearson correlation coefficient and error bar (SEM). This exercise was repeated for comparison to both the U87 and MCF10a bulk RNA-Seq profiles to demonstrate better concordance between the U87 single cell profiles and the U87 bulk profile.
Figure 7B:
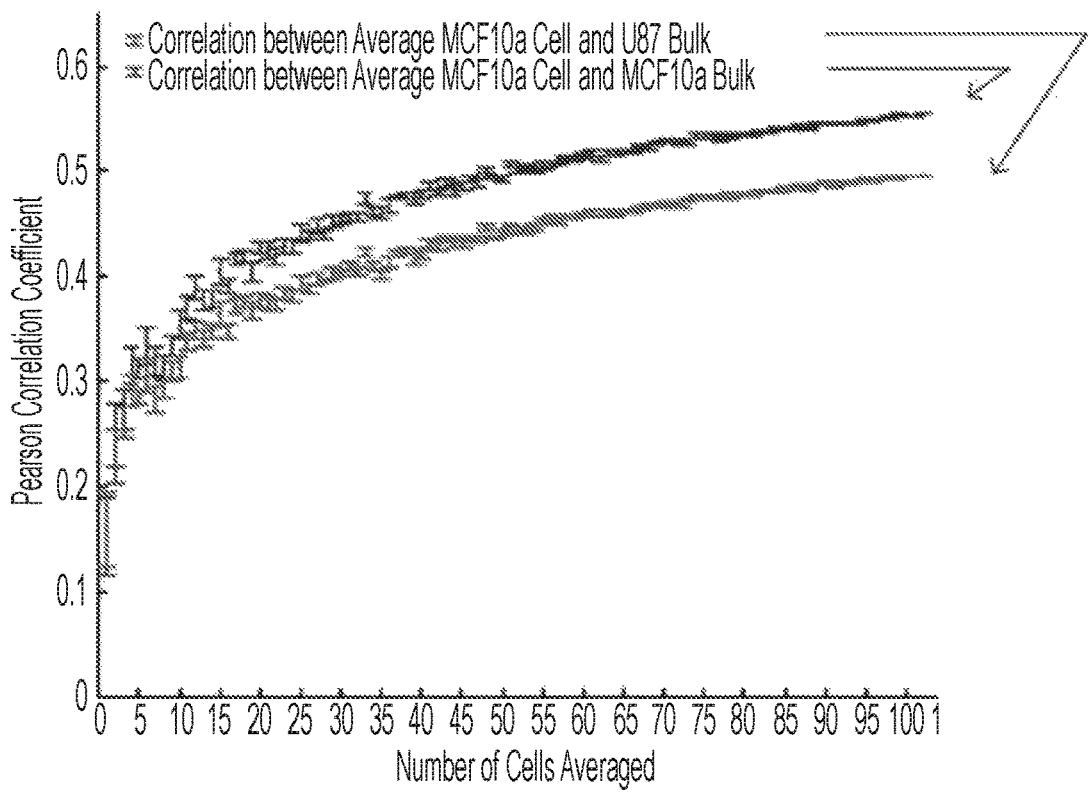

To assess the similarity of our single cell expression profiles to conventional, population-level RNA-Seq, the Pearson correlation between bulk RNA-Seq and single-cell medians constructed from different numbers of individual cells after normalizing by the total number of molecules detected in each cell were calculated (FIG. 7A and FIG. 7B). An analysis on single cell profiles originating from the U87-exclusive and MCF10a-exclusive lanes in Experiment 1 was conducted, randomly sampling the complete sets of profiles ten times without replacement for each point in the curves shown in FIG. 7A and FIG. 7B. This analysis shows that the single cell medians constructed from U87 single cell profiles correlate better with the bulk U87 RNA-Seq profile than with the bulk MCF10a RNA-Seq profile (FIG. 7A), and vice-versa (FIG. 7B). It also shows that the single cell median correlations saturate around $r=0.55$-$0.60$ depending on the cell type. As a point of comparison, an analysis for CEL-Seq and DR-Seq gave population-level Pearson correlations of 0.71 and 0.69, respectively. See, for example, Dey S S, Kester L, Spanjaard B, Bienko M, van Oudenaarden A: Integrated genome and transcriptome sequencing of the same cell. *Nat Biotechnol* 2015, 33(3):285-289, which is herein incorporated by reference in its entirety.

Figure 7C:
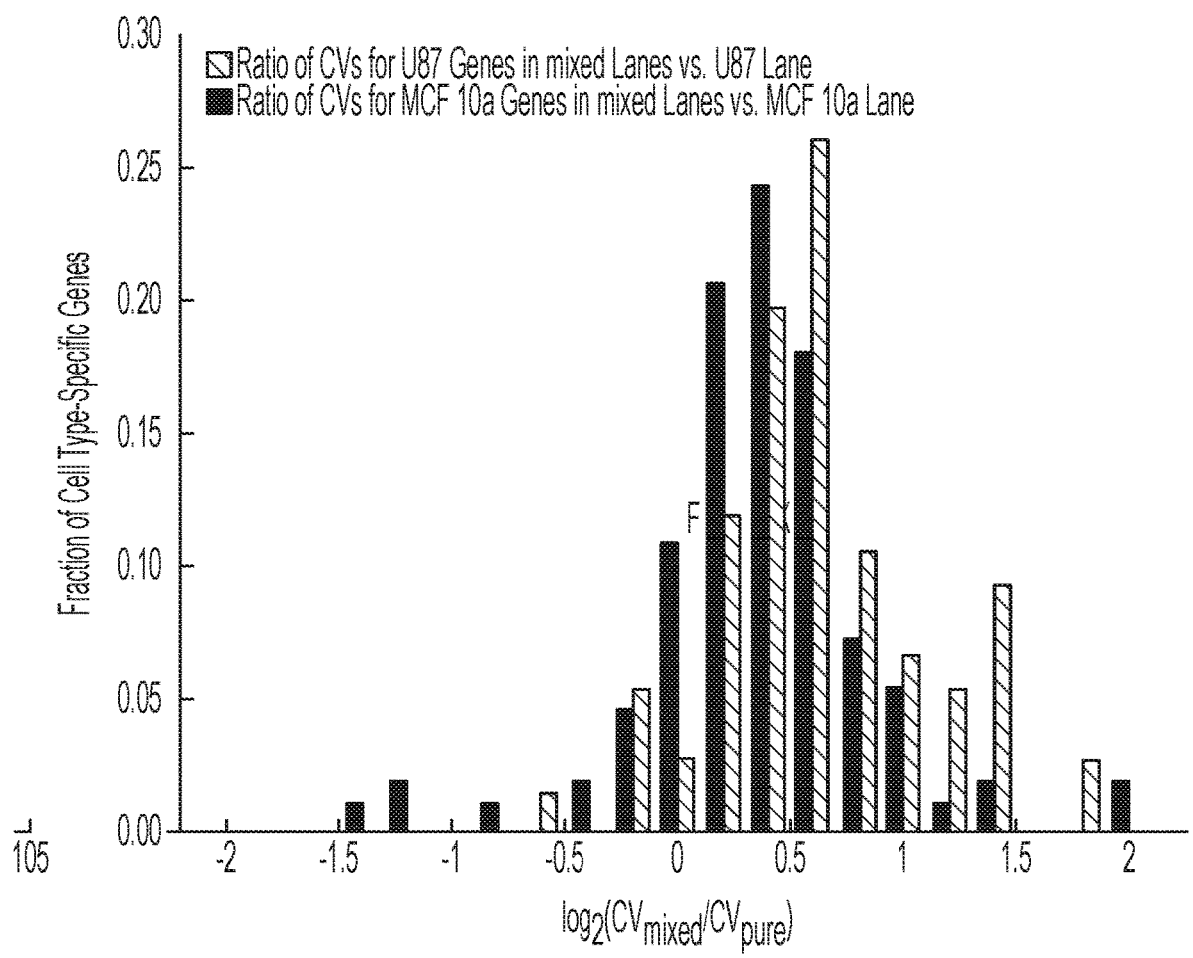

To further demonstrate the robustness of our data set, classifier for U87 and MCF10a cells in Experiment 1 were built. Single cell profiles from lanes that contained either exclusively U87 cells of MCF10a cells were used to identify 189 differentially expressed genes ($p<0.05$, Wilcoxin rank-sum test). FIG. 7C shows the log-ratio of the coefficients of variation (CVs) for each of these two genes sets between the mixed lane profiles and the profiles from the respective pure lanes. The log-ratio of CVs is greater than zero (CV ratio greater than one) for 92% of U87-specific genes and 85% of MCF10a-specific genes.

Figure 8A:
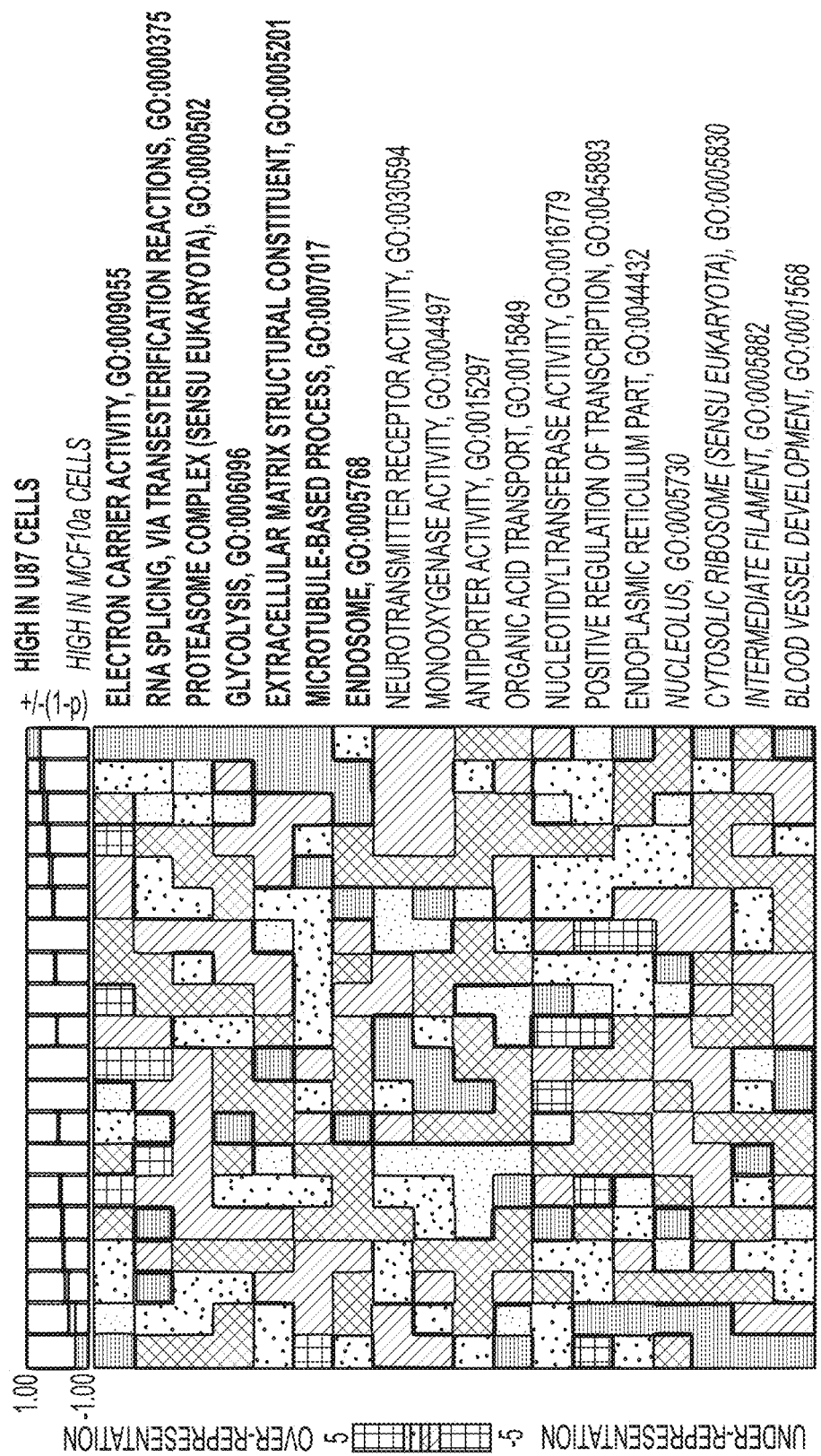
FIGS. 8A-8C provide for cell type separation by single cell RNA-Seq.
Figure 8B:
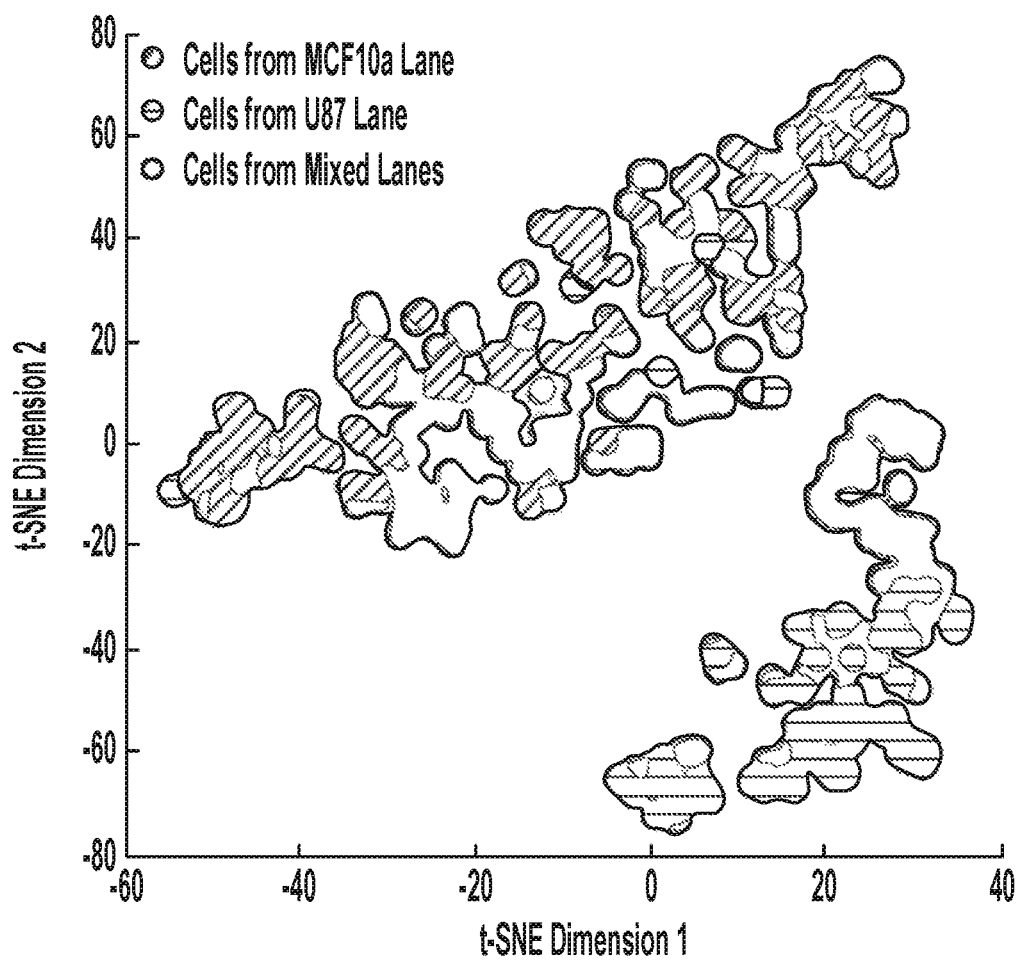
Figure 8C:
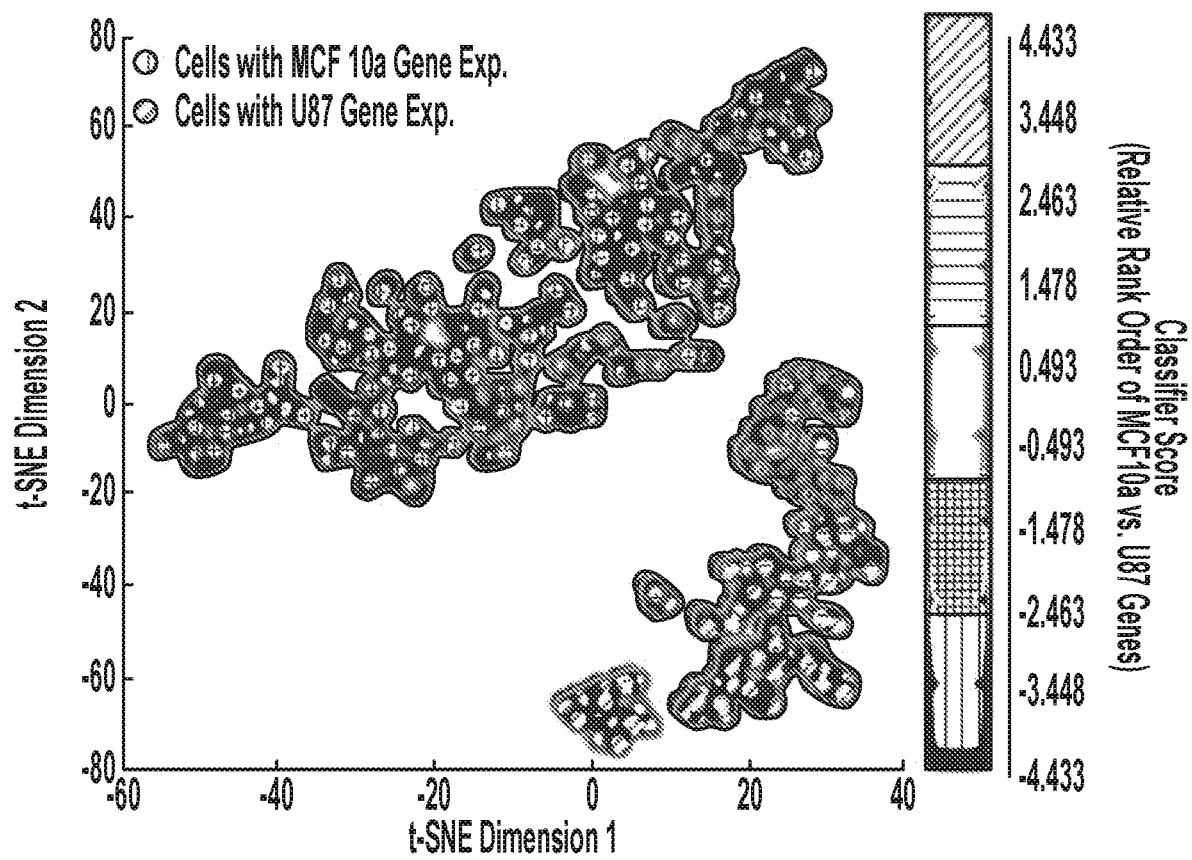
Figure 9:
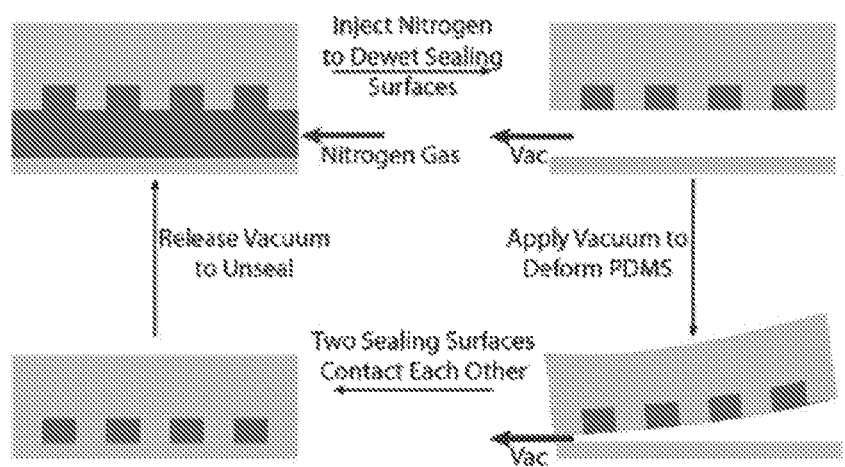
FIG. 9 provides for a schematic of a reversible PDMS-based device in one aspect of the disclosure.
Figure 10:
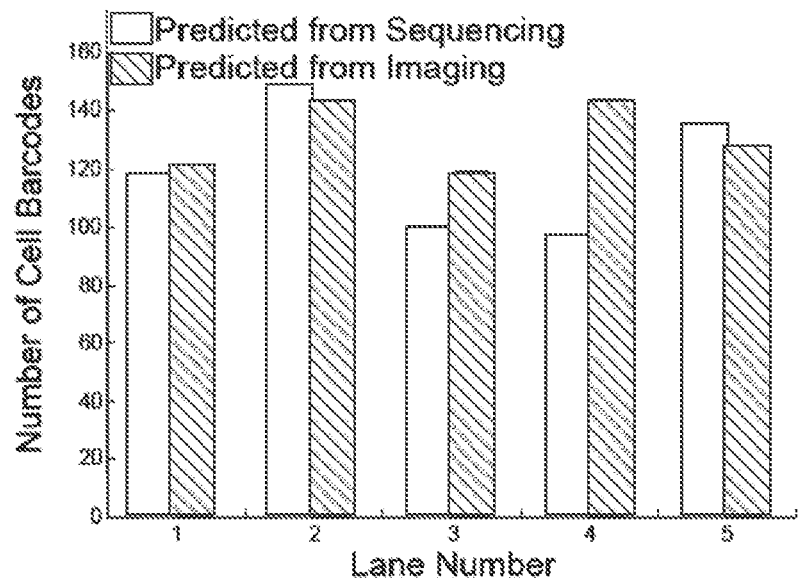
FIG. 10 describes ingle Cell RNA-Seq of U87 and MCF10a Cell Lines ~600 cells paired with beads in five-lane microfluidic device.
Figure 11:
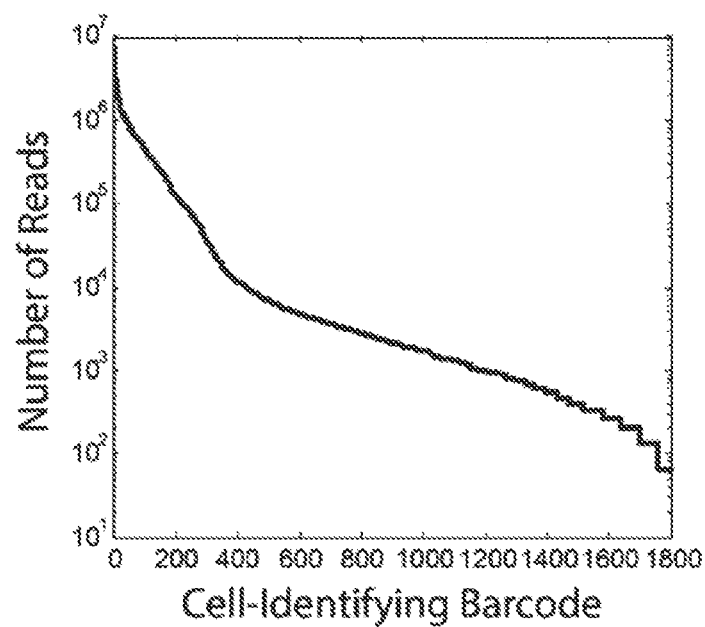
FIG. 11 shows the number of reads associated with each cell-identifying barcode showing a sharp change in slope at ~350 barcodes, consistent with the ~350 cell-bead pairs loaded in the microwell array. The remaining cell-identifying barcodes originate either from sequencing error or ambient, background mRNA hybridizing to beads in the device that were not associated with a cell.
Figure 12:
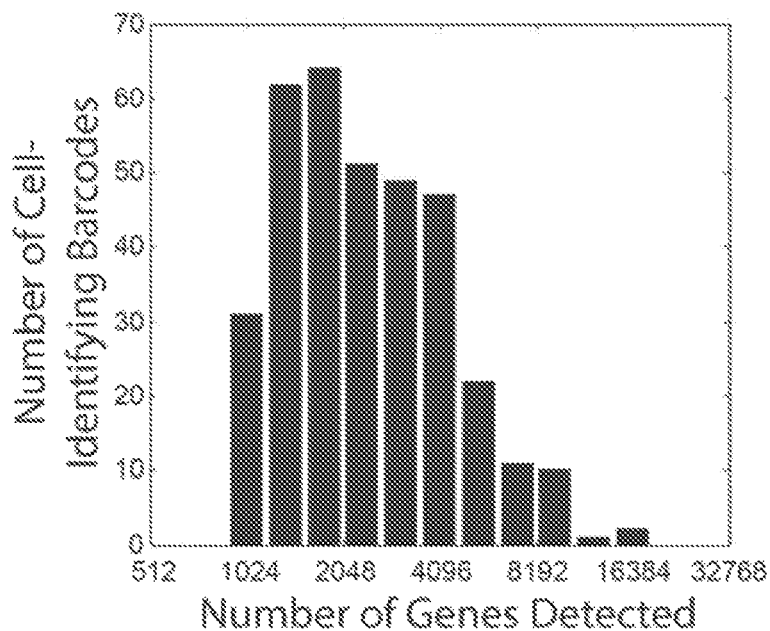
FIG. 12 is a histogram showing that the number of genes detected per individual cell ranges from 1,000 to 17,000 (~3,400 genes per cell on average).
Figure 13A:
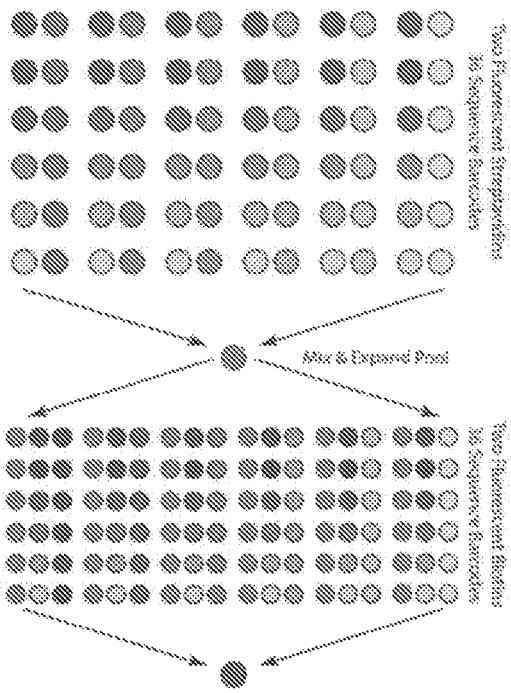
FIG. 13A and FIG. 13B describes a representative example of the capabilities described herein for linking high content imaging to single cell sequencing. For example, introducing 4 different at 6 intensities generates $6^4$ or 1296 optical barcodes (FIG. 13A).
Figure 13B:
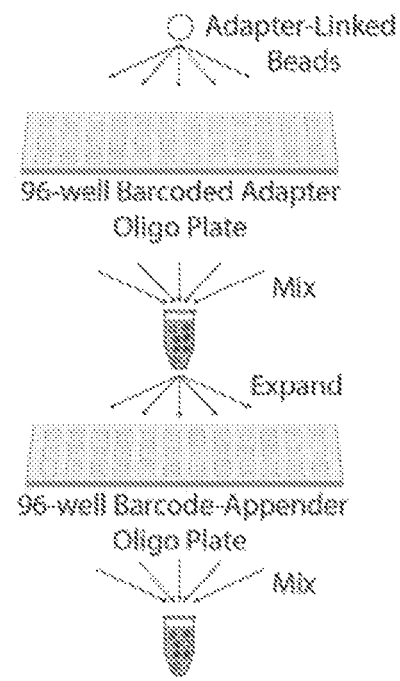
Figures 14A, 14B:
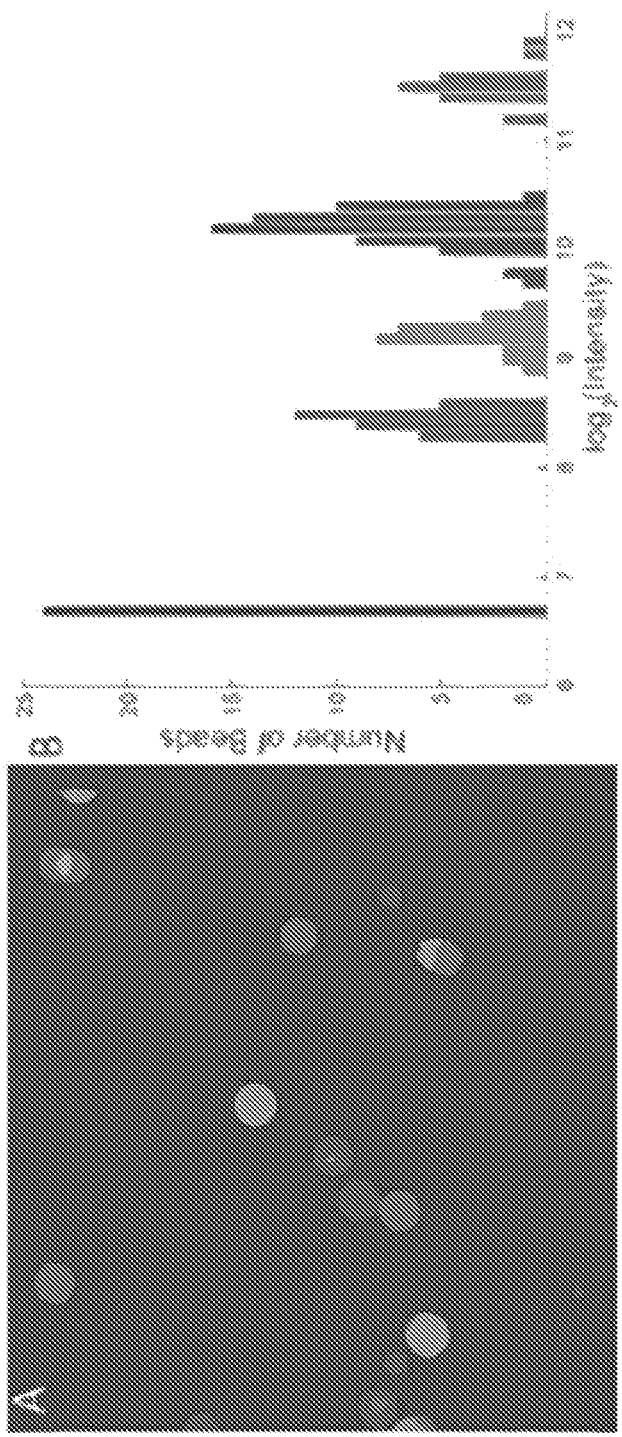
FIGS. 14A and 14B provides for (FIG. 14A) a fluorescence image of beads with different fluorescent colors generated by combinatorial mixing of different fluorescent dyes at different concentrations. Each color combination and intensity represents a different sequence barcode for mRNA capture that is also attached to the bead. In this example the optical barcodes themselves are not sequences.

FIG. 8A shows a pathway analysis of gene ontologies enriched across >11,600 genes that were both detected across our 396 single cell profiles and available in the iPAGE database and ranked based on differential expression in Experiment 1. See, for example, Goodarzi H, Elemento O, Tavazoie S: Revealing global regulatory perturbations across human cancers. *Mol Cell* 2009, 36(5):900-911, which is herein incorporated by reference in its entirety. A matrix of Spearman correlation coefficients across our 396 profiles based on rank-ordering the 189 differentially expressed genes in each cell was then generated. The data was clustered spatially using the t-stochastic neighborhood embedding (t-SNE) algorithm, described for example in Van der Maaten L, Hinton G: Visualizing data using t-SNE. *Journal of Machine Learning Research* 2008, 9(2579-2605):85, a clustering algorithm applied to high-dimensional single cell analysis data (FIG. 8B and FIG. 8C). This t-SNE result contains two closely associated clusters of individual cells.

To understand the origin of these two clusters, the t-SNE clustering with two different color-schemes are displayed. In FIG. 8B, it is shown how single cell profiles from the various lanes of a device described herein are distributed. One of the two clusters contains all of the cells from the MCF10a-exclusive lane, while the other contains nearly all of the cells from the U87 lane with a few exceptions. Single cell profiles from the mixed lanes are distributed throughout the two clusters. While the single cell profiles from mixed lanes are distributed uniformly throughout the MFC10a cluster, there is some separation between a subset of mixed lane profiles and the U87-exclusive lane profiles in the U87 cluster. In FIG. 8C, the same clustering result with a different color scheme that indicates the relative rank ordering of the U87 vs. MCF10a gene sets in each profile is described. This metric associates the cells in each of the two clusters with the expected cell type-specific expression pattern.

In an aspect, the microfluidic platforms described throughout are compatible with transcriptome-wide analysis of individual cells by RNA-Seq. In an another aspect, either could be combined with a sequence-based barcoding scheme to generate a pooled cDNA library from hundreds or thousands of individual cells. For example, in the bead capture device, barcoding is not strictly necessary because physical means could be used to extract the beads from the microwells for downstream processing with conventional labware. Alternatively, fluorescently labeled oligonucleotide probes could be used to image captured RNA molecules similar to RNA-FISH. Probes could be introduced sequentially, imaged, and removed in cycles or combined with previously reported multiplexing schemes. Similarly, sequential rounds of qRT-PCR in sealed microwells could allow targeted detection of specific genes or mutations in captured RNA.

Synthesis of Dual-Barcoded mRNA Capture Beads

In another aspect, dual-barcoded mRNA capture beads were synthesized by the work flow shown in FIG. 15A. Sequence-barcoded mRNA capture beads (MACOSKO-2011-10, ChemGenes) are thoroughly washed with water to remove free-floating oligonucleotides and then immediately evenly distributed into 64 wells on a 96 well plate. The 96 well plate is then sealed, vortexed, and sonicated. In doing so, a small amount of sequence-barcoded mRNA capture oligonucleotides fall off from the beads (bead-free DNA) and get released into the liquid phase. The supernatant from each well (contains bead-free DNA) are collected into separate tubes, converted into double stranded DNA, PCR amplified and indexed, pooled, gel purified, and sequenced (bead-free DNA sequencing data). A unique combination of short oligonucleotides selected from a first set of 6 types of short oligonucleotides and ligation reaction mixture are sequentially added into each of the 64 wells. This results in the attachment of a unique and known combination of oligonucleotides to the beads in each well (FIG. 15B). The sequencing barcode sequence of beads in each well can be obtained from the bead-free DNA sequencing data. Thus, a two-column look-up table (FIG. 15C) is generated where each row represents a bead, one column contains sequencing barcode sequence, and the other column contains a 6-digit optical barcode sequence. The beads are then pooled together and subjected to a second round of split-and-pool synthesis with a different set of 6 types of short oligonucleotides. This generates another two-column look-up table. Each bead appears once in each of the two look-up tables and has a 12-digit binary optical barcode sequence. A total of 4096 types of optically barcoded beads are made. To prevent these newly ligated oligonucleotides from interfering the single-cell RNA-seq library prep steps, a polyethylene glycol (PEG) chain is inserted in the short oligonucleotide.

It was initially attempted to optically barcode the beads spectrally (i.e., labeling the beads with varying amount of dyes with different emission wavelength). The challenge of this approach is that the emission wavelength of commercially available dyes is rather broad. Only a few distinct dyes can fit on the full spectrum of light thus limiting the barcoding capacity. We then tried to barcoding beads with a combination of short oligonucleotides with different sequences. Attachment methods involving use of DNA polymerase may not work.

Demultiplexing Work Flow 12 rounds of sequential fluorescent in situ hybridization (FISH) were used to read out the 12-digit binary optical barcode sequence. Each round of FISH has four major steps including background scan, probe hybridization (150 nM probes), probe scan, and probe stripping (150 mM NaOH). Here the probes used in each round are fluorophore-labeled short oligonucleotides whose sequences are complementary to each of the 12 short oligonucleotides that was ligated to the beads during bead synthesis step. During each FISH round, two populations of beads were detected in terms of fluorescent intensity in the fluorophore channel. Beads in the population that has a higher and lower intensity are assigned a binary sequence of 1 and 0 respectively. After the full 12 rounds of FISH, a 12-digit binary optical sequence is generated for each bead. FIG. 16A shows representative images from optical phenotyping of cells and from optical demultiplexing of beads. FIG. 16B is a histogram of bead intensity after each of the 12 rounds of probe hybridization. FIG. 16C is histogram of optical barcode sequence occurrences.

Instrumentation for Automated Optical Demultiplexing

An automated reagent delivery and scanning system (FIG. 17A) was built for automated on-chip optical demultiplexing (FIG. 17B). The design is illustrated in FIG. 17A. In the automated reagent delivery system, fixed positive pressure was used to drive fluid flow, multichannel rotary selector valves located at the upstream of the microwell array device were used to toggle between different reagent channels, and a solenoid valve located at the downstream of the microwell array device was used to control the on/off of the reagent flow. The microwell array device is thus constantly being pressurized during incubation steps which help prevent the device from drying and suppress bubble formation. A microfluidic flow cell which traps bubbles came from upstream is connected in-serial immediate upstream of the microwell array device to further prevent bubbles from entering the microwell array device. A water hammer arrestor consists of a half-filled cryotube was connected immediate downstream of the microwell array device and upstream of the on-off flow switch valve to buffer the hydraulic shock produced by the on-off switch valve which can cause bead loss. The automated scanning system consists of laser light source, motorized stage, shuttle, and filter wheel, an inverted microscope, and a camera. An optically transparent mechanical support (glass slide) was attached to the bottom surface of the microwell array device to prevent sagging which facilitates imaging. Both the reagent delivery system and the scanning system are controlled by a C++ program.

Full Single-Cell RNA Sequencing and Imaging Work Flow

An an embodiment, full single-cell RNA sequencing and imaging work flow may be as follows. A microwell array device is filled and flushed with TBS buffer. Single-cell suspension is then loaded into the device. The device is scanned under a microscope to obtain imaging phenotype and location of each individual cell in the device. Optically barcoded mRNA capture beads are then loaded into the device. Lysis buffer and oil are flowed into the device sequentially to trigger cell lysis and physically isolate the microwells from each other allowing mRNA from cells in different microwells to be captured by their respective co-localized beads. After the mRNA capture step, captured mRNA molecules are reverse transcribed which coverts mRNA into double-stranded DNA-RNA duplex resulting in the barcoding of cDNA. Any unused single-stranded capture primers on bead surface are removed by exonuclease I digestion. The device is then subject to twelve rounds of sequential FISH to read out the optical barcode sequence of each bead and their locations in the device. So far, all the reactions including cell lysis, mRNA capture, reverse transcription, exonuclease I digestion, and optical demultiplexing are performed on the device which allows the linking between each cell's imaging phenotype and optical barcode sequence of the bead that resides in the same well with the cell. After the optical demultiplexing step, all beads are extracted from the device. Tube-based PCR reactions are used to pre-amplify bead-bound cDNA molecules. In the case where the number of cells in the device is greater than the optical barcoding capacity enabled by the current 4096 unique optical sequences, the microwell array is cut into multiple pieces before the beads were extracted and processed in separate tubes in parallel. Each piece contains a number of cells within the optical barcoding capacity of the current 4096 unique optical sequences. By doing so, the optical barcoding capacity gains a n fold increase where n is the number of pieces the full device is cut into. The amplified cDNA copies are released into the liquid phase and further amplified into sequencing library and sequenced by commercially-available kit (Nextera XT, Illumina) and sequencers (NextSeq, Illumina). The raw fastq files generated by sequencers are processed to generate a digital expression matrix where each column represents the expression profile of a cell and each row represents the expression level of a gene. The look-up table generated in the bead synthesis step are then used to further link each cell's imaging phenotype to sequencing barcode sequence of the bead that resided in the same well with the cell and the associated mRNA expression profile.

Mixed Species

Performance of the technique was evaluated by an experiment using two cell lines of distinct species (human U87 and mouse 3T3). Each of the two cell lines were stained with a dye with different emission wavelength. The two cell lines were then mixed in approximately equal proportion and loaded into a microwell array device followed by the full work flow described above. The imaging phenotypes obtained in this experiment include live stain intensity, cell size and morphology.

Sequencing Data Quality

FIGS. 18A-E show sequencing data quality based on two major metrics for single-cell sequencing data quality: purity and molecular capture efficiency. In the mixed species experiment on human U87 and mouse 3T3, an average purity of 98% was observed, and an average molecular capture efficiency of 2452 genes/6224 molecules was detected per cell.

Linking Accuracy

Since the two cell lines are from different species (human and mouse) that have different genomes, the species identity of each cell was determined based on the genome that majority of its mRNA molecules was mapped to. In addition, cells from different species were live stained with different dyes. Therefore, the species identity of each cell was independently determined based on the imaging data. The linking accuracy is defined as the percentage of cells having consistent species calls based on both sequencing and imaging data. A linking accuracy of 90% was demonstrated in this initial proof-of-concept experiment.

Single-Stranded Ligation and Detached Oligonucleotides

Optically barcoded mRNA capture beads are generated by modifying sequence barcoded mRNA capture beads. These beads contain oligonucleotides with a universal primer sequence on the 5'-end, barcode sequences in the middle, and oligo(dT) on the 3'-end for mRNA capture. DNA-replicating enzymes, such as DNA polymerase, are used to attach the optical barcode oligonucleotides to the 3'-end of a subset of mRNA capture oligos on the beads. In addition, DNA-replicating enzymes, such as DNA polymerase, are used to generate sequencing libraries for identifying the barcode sequences attached to each bead. Exposure of the mRNA capture beads to enzymes that replicate DNA in a template-directed fashion prior to conducting single-cell RNA-Seq may be disadvantageous. This may be due to these enzymes causing mRNA capture oligonucleotides and optical barcode oligonucleotides to serve as primers and templates for each other, generating "primer-dimers" on the surface of the beads. This may reduce the concentration of mRNA capture oligonucleotides on the bead that is available for hybridization to mRNA and cDNA synthesis in single-cell RNA-Seq.

In an aspect, the potential problems noted above may be resolved by avoiding exposure of the beads to DNA-replicating enzymes when modifying the oligonucleotides on the bead and generating sequencing libraries for identifying the barcode sequences on each bead. In this aspect, a single-stranded ligation reaction facilitated by a DNA ligase, rather than primer extension facilitated by DNA polymerase is used to attach the optical barcode oligonucleotides to a subset of mRNA capture oligonucleotides on the bead.

In an aspect, sequencing libraries containing the barcode sequences of each bead are generated by taking advantage of the fact that a small number of oligonucleotides detach from the beads at a slow rate, making them available in solution. By allowing this to occur and isolating these detached oligonucleotides from the supernatant of the beads, a sequencing library using DNA polymerase can be generated, but without exposing the beads directly to this enzyme.

Single-stranded ligation and use of detached oligonucleotides permit synthesis of optically barcoded mRNA capture beads, decoding of the barcode sequences, and efficient single-cell RNA-Seq using those beads.

The challenge noted above could be applicable to other areas. While the mRNA capture beads modified with optical barcode sequences, it may be desireable to modify the mRNA capture beads for applications such as targeted capture of specific gene sequences. For example, one could envision modifying a subset of oligonucleotides on the mRNA capture beads using the methods described above to facilitate targeted enrichment of a specific gene sequence from individual cells while still allowing unbiased profiling of the mRNA from those cells using the remaining oligo(dT) capture sequence. Specific cases include targeted enrichment of the T cell receptor repertoire or antibody repertoire from immune populations with simultaneous, unbiased mRNA profiling of the same individual cells.

Kits

In another aspect, the disclosure provides for a kit comprising, consisting essentially of, or consisting of any of probes, beads, and regents disclosed herein. In an aspect, the kit includes any of the combination of probes, beads, and regents disclosed in the Figures herein. In another aspect, the kit provides for probes, beads, and regents applied in a manner that is consistent with the methodology of the examples and figures. In another aspect, the kit provides instructions or guidance regarding the use of the compositions, probes, devices, systems or methods described herein.

In an aspect, the kit includes instructions describing the methodology described herein.

The following examples serve to illustrate certain aspects of the disclosure and are not intended to limit the disclosure.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1

Generation of Optically Barcoded mRNA Capture Beads for Optical Demultiplexing by Multi-Color Fluorescence Imaging for Single Cell RNA-Seq N-succinimide-coated Sepharose beads with a mean diameter of ~30 μm were obtained from GE Healthcare in isopropanol. The beads were washed three times with water by centrifugation and split into 125 different tubes. The beads were then re-suspended in a reaction mixture with a final concentration of 100 mM sodium borate (pH 8.5) along with three differently-labeled streptavidin proteins (streptavidin-AlexaFluor 488, streptavidin-AlexaFluor 546, and Streptavidin-AlexaFluor 647 from Life Technologies). For each of the 125 reaction mixtures, the three proteins were added at one of 5 concentrations such that each of the 125 reaction mixtures had one of $5^3=125$ unique combinations of labels and label intensities. The reaction was incubated at room temperature for one hour on a rotisserie to allow the labeled streptavidins to covalently react with the beads, form amide bonds. The beads were then washed five times in 50 mM Tris-HCl pH 8, 50 mM NaCl, and 0.1% Tween-20 before using to completely quench any remaining reactive groups on the beads. Each of the 125 uniquely labeled sets of beads were then incubated with a uniquely barcoded, 5'-biotinylated oligonucleotide. The oligonucleotides had a universal adapter sequence on the 5'-end to facilitate amplification, a barcode sequence, and oligo(dT) on the 3'-end to facilitate mRNA capture. The oligonucleotides became bound to the beads through the biotin-streptavidin interaction, resulting in beads that could be identified by fluorescence microscopy based on their unique configuration of fluorescent labels to harbor a specific nucleic acid barcode sequence.

Generation of Optically Barcoded mRNA Capture Beads for Optical Demultiplexing by Sequential Fluorescence Hybridization for Single Cell RNA-Seq 2.4 million beads aminated polystyrene beads (Custom Primer Support 200 Amino, GE) were reacted with an 8% solution of glutaraldehyde in Cyanoborohydride Coupling Buffer (Sigma) for six hours a room temperature. After washing the beads in phosphate buffered saline (PBS), the beads were divided evenly into each of 32 tubes. To each tube, 62.5 pmol of a unique 5'-aminated oligonucleotide were added containing an adapter sequence, a unique capture barcode sequence, and a linker sequence. In addition, zero or more 5'-aminated oligonucleotides were added from a set of five, each of which contains a unique optical barcode sequence and a linker sequence. The constellation of oligonucleotides on the bead surface forms a binary code. For example, if there are five oligonucleotides in a set, and the first, third, and fourth oligonucleotides are present on the bead, then the code could be in an aspect, 10110. However, there will also be a bead in the set with the code 00000, where none of the oligonucleotides are present. This also provides a signal, a bead that does not fluoresce when exposed to any of the probes 2.5 pmol of each optical barcode oligonucleotide was further added. Each capture barcode sequence is associated with a unique set of optical barcode sequences. In this embodiment, there are 32 capture barcode sequences and $2^5=32$ possible combinations of optical barcode configurations added in the first round of synthesis. The 5'-aminated oligonucleotides were reacted with the aldehyde-conjugated beads in Cyanoborohydride Coupling buffer for 12 hours at room temperature. The reaction was then quenched by the reaction by adding 1 M Tris-HCl to each well. The beads were then washed in PBS.

In a second barcode synthesis, the 32 reactions from the first round were pooled and then re-distributed into each of 128 tubes. To each tube, 150 pmol of a unique oligonucleotide was added containing a linker sequence complementary to that in the capture barcode oligonucleotides already attached to the beads, a second capture barcode sequence, a random sequence (for unique molecular identification), and a poly(A) sequence. In addition, zero or more oligonucleotides from a set of seven were added, each of which contains a unique optical barcode sequence and a linker sequence complementary to that in the optical barcode oligonucleotides already attached to the beads. 20 pmol of each optical barcode oligonucleotide. Each capture barcode sequence is associated with a unique set of optical barcode sequences. There are 128 capture barcode sequences and $2^7=128$ possible combinations of optical barcode configurations added in the second round of synthesis. In combination with the first round of synthesis, the second round of synthesis results in a set of 32×128=4,096 uniquely barcoded beads with both unique capture and optical barcodes attached. The second round oligonucleotides was hybridized to the oligonucleotides attached in the first round in Buffer 2 (New England BioLabs) with 1% tween-20 (Sigma) at 50 C for 20 minutes and at room temperature for 12 hours. The beads were then washed and then copied the second round oligonucleotides onto the 3'-end of the first round oligonucleotides by primer extension with Klenow Large Fragment DNA Polymerase (New England BioLabs) at room temperature for 2 hours. The primer extension reaction was quenched with EDTA followed by sodium hydroxide. The beads from all 128 reactions were then pooled and washed them extensively in sodium hydroxide and Wash Buffer (10 mM Tris pH 8, 1 mM EDTA, 0.01% tween-20).

Fabrication of a PDMS Microwell Array Device

Microfabricated arrays of cylindrical pillars in photoresist on a silicon wafer were obtained from FlowJEM. The pillars were 50 microns in diameter and 50 microns tall. A second wafer contained a relief pattern of a flow channel. A 1:10 mixture of liquid polydimethylsiloxane (PDMS) base and curing agent (Sylgard 184, Dow-Corning) was poured on each wafer. A glass microscope slide was pressed onto the uncured liquid PDMS that had been poured on the wafer containing cylindrical pillars, forming a thin layer of PDMS between the wafer and the glass slide. Both wafers with liquid PDMS were then placed in an oven to cure at 90° C. overnight. The cured, solidified PDMS were then peeled from both wafers resulting in a thin microwell array on the glass slide and a PDMS flow channel. After using a punch to insert inlet and outlet holes on either end of the flow channel, air plasma was used to bond the flow channel over the microwell array. The resulting microwell array flow cell device was then used for single cell RNA-Seq and optical demultiplexing.

Single Cell RNA-Seq Library Generation in a Microwell Array Device Using In Vitro Transcription Prior to the experiment, the device was flushed with 0.1% Tween-20 and incubated for several hours to hydrate the microwells, which were subsequently washed with PBS. Cell suspensions were counted using the Countess automated cell counter (Life Technologies). A suspension of cells in PBS mixed with Calcein AM (live stain) was flowed into the device and incubated for five minutes. Cells were deposited in the microwells by gravity. After thoroughly removing any excess cells with PBS, a suspension of barcoded capture beads that had been pre-counted by microscopy was introduced in PBS and allowed to load under gravity for five minutes. Excess beads were thoroughly removed with PBS and the flow cell was incubated on ice. A lysis buffer containing 0.08% Triton X-100 supplemented with SUPERaseIN (Life Technologies) was flowed under ice-cold conditions immediately followed by fluorinert oil (Sigma) to seal the device. After two cycles of freeze-thaw at −80 C to enhance cell lysis, the device was incubated at room temperature for 60 minutes for mRNA capture. After one hour of incubation for mRNA capture, the device was unsealed by rapid removal of the fluorinert oil with 20 mM Tris-HCl pH 8 containing 1% Triton X-100 and SUPERaseIN followed by thorough washing of the device with 20 mM Tris-HCl pH 8, 50 mM NaCl, and 0.1% Tween-20.

The mRNA captured on the beads was reverse transcribed using ProtoScript II Reverse Transcriptase (New England BioLabs) for two hours at 42 C in 1× ProtoScript Reverse Transcriptase Buffer supplemented with 10 mM DTT, 0.5 mM dNTPs, 0.1% Tween-20, and SUPERaseIN. The reaction mixture was then removed with 20 mM Tris-HCl pH 8, 50 mM NaCl, and 0.1% Tween-20. Second strand synthesis was carried out using the MessageAmp II aRNA amplification kit (Ambion) according to the manufacturer's instructions. This involves a reaction mixture with DNA polymerase and RNaseH that is incubated for two hours at 16 C. After removing the second strand reaction mixture with 20 mM Tris-HCl pH 8, 50 mM NaCl, and 0.1% Tween-20, in vitro transcription (IVT) was carried out using reagents in the MessageAmp II aRNA amplification kit (Ambion) including T7 RNA polymerase according to the manufacturer's instructions for 13 hours at 37 C. The reaction linearly amplified the double-stranded cDNA libraries on the beads, eluting pools of barcoded aRNA into the flow channel which was subsequently removed using a pipette and purified using an RNA Clean & Concentrator Column (Zymo).

aRNA was then reverse transcribed using uniquely barcoded random hexamer primers using PrimeScript Reverse Transcriptase (Clontech) supplemented with 0.5 mM dNTPs, 10 mM DTT, 1× PrimeScript Buffer, and 0.1 U/uL SUPERaseIN. The reaction proceeded for 10 minutes at 25° C. and two hours at 42° C. The RNA-cDNA hybrid product was purified twice using 0.65×Ampure XP beads (Beckman). The resulting cDNA libraries were then enriched by PCR using Phusion High Fidelity DNA polymerase (New England BioLabs) using the Illumina RP1 and RPI primers. The resulting PCR product was then purified on a 1.5% agarose gel, extracted using a Gel Extraction Kit (Qiagen), purified using 0.65× Ampure XP beads (Beckman), and sequenced on a NextSeq 500 sequencer (Illumina).

Single Cell RNA-Seq Library Generation in a Microwell Array Device Using Template-Switching Cells and mRNA capture beads were loaded into the microwell array device as described above. The device was then placed on a computerized temperature and fluidic control system for automated single cell library production. The system consists of a manually controlled pressurization system, software, an electronic six-port rotary selector valve (Rheodyne), and a thermoelectric heater-cooler module (TE Technology). After cooling the system to 4 C, a lysis solution comprised of TCL Buffer (Qiagen) and 1% 2-mercaptoethanol was introduced to the device, which was rapidly and automatically sealed with fluorinert (Sigma). After removing the oil and unsealing the microwells, a reverse transcription reaction mixture comprised of 1× Maxima RT Buffer, 1 mM dNTPs, 1 U/uL SUPERaseIN, 2.5 uM template-switching oligonucleotide, 0.1% Tween-20, and 10 U/uL Maxima H-Reverse Transcriptase (ThermoFisher) was introduced and incubated for 30 minutes at room temperature followed by 90 minutes at 42 C.

After removing the reverse transcription reaction mixture, the beads were removed from the microwells by sonication, concentrated by centrifugation and incubated for 30 minutes at 37 C with Exonuclease I in 1× Exonuclease I Buffer (New England BioLabs). The beads were then washed in 10 mM Tris-HCl pH 8, 1 mM EDTA, and 0.5% sodium dodecyl sulfate (SDS) followed by 10 mM Tris-HCl pH 8, 1 mM EDTA, and 0.01% Tween-20. The beads were then re-suspended in a PCR reaction mixture containing 1× HiFi Hot Start Ready Mix (Kappa) and 1 uM PCR primer and thermocycled to amplify a full-length, double-stranded, pooled cDNA library. The PCR product was purified with 0.6× Ampure XP beads (Beckman). The library was then fragmented and a sequencing adapter introduced using the Nextera XT library preparation kit (Illumina) according to the manufacturer's instructions. Finally, the sequencing library was enriched by PCR using a reverse PCR primer from the Nextera XT kit and a custom forward PCR primer along with amplification reagents from the Nextera XT kit used according to the manufacturer's instructions. The resulting PCR product was purified with 0.6× Ampure XP beads (Beckman) and sequenced on a NextSeq 500 sequencer (Illumina).

Optical Demultiplexing of Barcoded mRNA Capture Beads

Figure 1B:
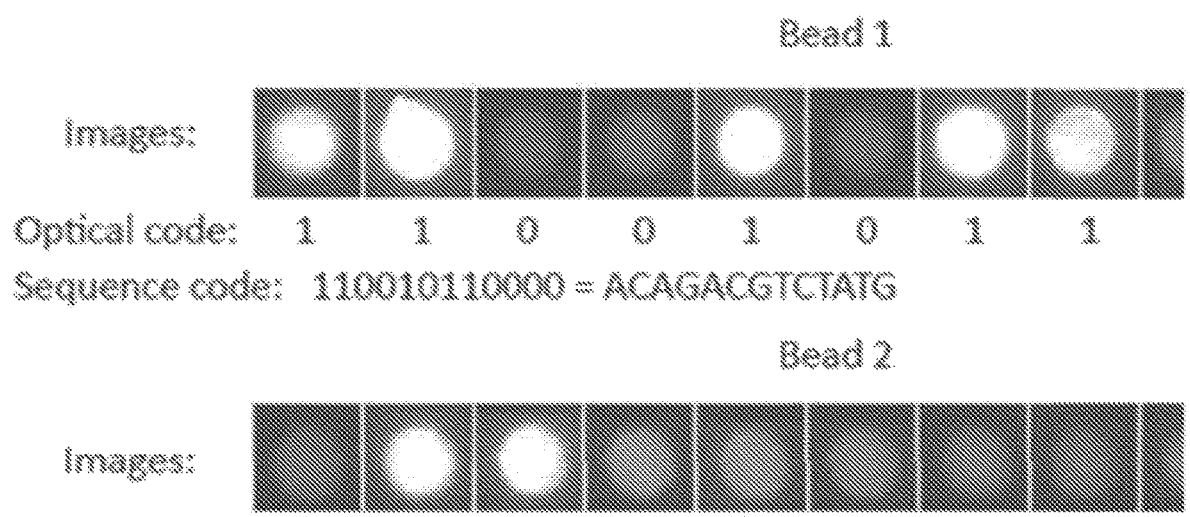
FIG. 1B provides for a series of 12 fluorescence images from each of two beads in the microwell array device after introduction of each of 12 barcoded probes. When a probe is complimentary to optical barcode oligonucleotides on the bead surface, the bead becomes fluorescent, resulting in the 12-digit binary code that corresponds to a sequence attached to the capture oligonucleotides on the bead.

Following cDNA synthesis on the surface of optically barcoded capture beads, the microwell array device was transferred to an epifluorescence microscope system. The microscope system contains an inverted microscope frame (Ti-U, Nikon), an electron-multiplied charge coupled device (EM-CCD) camera (iXon, Andor), a 20× 0.75 NA air objective lens (Nikon), a three-axis motorized stage (ASI), a 140 mW 637 nm optically pumped semiconductor laser (OBIS, Coherent), and custom optics for coupling the laser beam into the microscope. The custom optical path includes an engineered diffusor (Thorlabs) and electronic phase scrambling device for flattening the illumination field. An automated, computer-controlled fluidics system is attached the microscope system and contains two, ten-channel rotary selector valves (Rheodyne). A single computer program controls the fluidics system, laser shutter, camera, and microscope stage. Each of twelve, Cy5-labeled optical barcode probes was loaded into the channels of the fluidics system. The optical barcode probes were each complementary to one of the optical barcode oligonucleotides attached the beads as described above. In addition, a wash buffer (20 mM Tris-HCl pH 8, 50 mM NaCl, and 0.1% Tween-20) and a denaturing solution (100 mM NaOH) were loaded into independent channels of the fluidics system. The first of twelve optical barcode probes was flowed into the flow cell, incubated at room temperature for ten minutes, and washed out with wash buffer. After washing, the microscope automatically scanned and imaged the entire microwell array and identifies the beads in each microwell that are fluorescently labeled with the first optical barcode probe by hybridization, indicating the presence of the first optical barcode sequence. The denaturing solution was then introduced to the flow cell which causes the first optical barcode probe to dissociate from the beads and exit the flow cell. After washing with wash buffer, the process was repeated for all of the remaining optical barcode probes. At conclusion, the configuration of optical barcode sequences attached to each bead can be inferred from the series of twelve fluorescence images. Because each unique configuration of optical barcode sequences corresponds to a specific capture barcode sequence associated with the cDNA that is also attached to each bead, the capture barcode sequence for each individual cell can be identified (see, for example, FIG. 1A and FIG. 1B). This allows a direct association between imaging information acquired from the cells, the capture barcode associated with the cDNA of the at cell that is read out on the sequencer, and therefore the transcriptome of that cell all through identification of the corresponding optical barcode.

Example 2

Fabrication PDMS Microwell Arrays for Single Cell RNA Printing

Silicon wafer masters (~4 in) with cylindrical pillars (diameter 50 micron; height 30 micron) for photolithography were obtained from Stanford Microfluidics Foundry and were subsequently exposed to 1H,1H,2H,2H-perfluorooctyltrichlorosilane (Alfa Aesar) vapor under vacuum for ~30 minutes to avoid curing of the PDMS on the wafer. PDMS (Sylgard 184, Dow Corning) was thoroughly mixed 10:1 (base:curing agent) and degassed under house vacuum for 2 hours. ~15 g of degassed PDMS was poured onto the 4 in silicon wafer master and allowed to cure overnight at ~90° C. This slab with microwells was then gently peeled off from the master and used to construct PDMS microreactor flow cells.

Surface Chemistry on Glass Coverslip

VistaVision Microscope cover glass (22×50×0.16 mm) was plasma sterilized (Harrick Plasma) for ~5 mins, and immediately immersed in 10% acetic acid (pH 3.5) ethanol solution containing 0.5% trimethoxysilanealdehyde (United Chemical Technologies), and incubated for 15 mins. The cover glass was then washed with ethanol, air-dried and heat cured at 90° C. for 10 mins. A 2.5 µM solution of 5'-aminated-LNA-oligo(dT) (Exiqon) in cyanoborohyride coupling buffer (Sigma) supplemented with 1M NaCl was added on the aldehyde surface of the cover glass. The cover glass was incubated for 3 hours at room temperature inside a humid chamber, and then washed with DI water. The aldehyde surface was then incubated in 10% ethanolamine in cyanoborohydride coupling buffer for 30 mins to quench the unreacted aldehydes.

Construction of the Flowcell

A rectangular slab (3.5×1.5×0.1 cm) of PDMS containing the microwell array in the center was cut and a double-sided adhesive tape (~120 micron thickness, Grace BioLabs) was adhered to the flat side of the PDMS slab that contained the microwells. The tape was cut in an elongated hexagonal shape, which formed the microchannel in the flowcell. The other side of the tape was pasted on the LNA coated cover glass to build the microfluidic device. Two holes were punched at the two end of the microchannel with a biopsy punch, which acted as the inlet and outlet of the device and tubing were attached to allow liquid flow. The periphery of the PDMS slab was sealed on to the cover glass using epoxy glue.

Experimental Procedure for Single Cell mRNA Printing on Glass

Figure 2A:
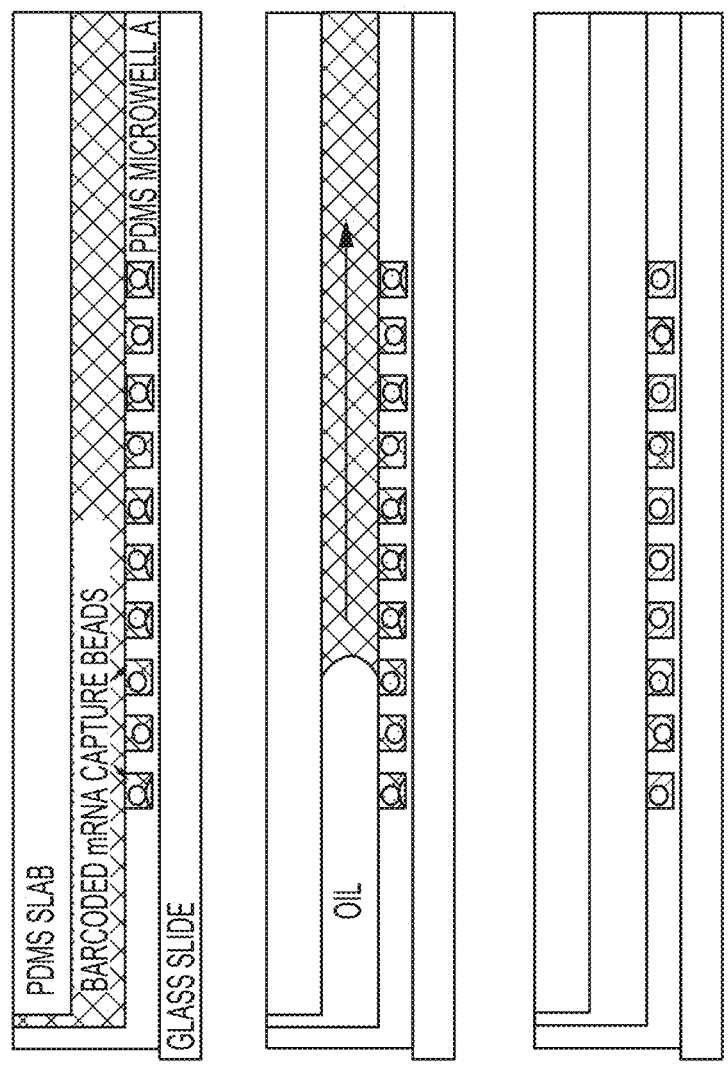
FIG. 2A shows schematic and fluorescence imaging data for single cell RNA capture on beads.

A suspension of U87 cells in PBS was flowed in to the device and loaded into the microwells by gravity (kept upside down) for 5 mins at room temperature. After washing with PBS buffer supplemented with SUPERaseIN (Ambion), the microwells were sealed using an automated mechanical device by placing the flow cell upside down on a screw mounted on a motorized z-stage (ASI) so that the top PDMS slab containing the microwells was pressed against the glass bottom. After sealing the wells mechanically, the seal was retained by hermetic sealing to trap the single cell lysate within a single microwell. The cells were lysed by freeze-thaw. Once the cells lysed, the mRNAs were captured on the LNA surface by hybridization of the 3'-polyA tail of the mRNA to the LNA-oligo(dT) during a 60 minute incubation. The microwells were then unsealed and the flow cell was immediately and vigorously washed with the Wash Buffer (20 mM Tris pH 8.0, 50 mM NaCl, 0.1% Tween-20), supplemented with SUPERaseIN (FIG. 2A). The flowcell was then incubated with TURBO DNase (Ambion) in TURBO DNase buffer, supplemented with 0.1% Tween-20 and SUPERaseIN for 30 mins at 37° C. to digest any residual genomic DNA. The mRNA captured on the LNA surface was reverse transcribed using M-MuLV Reverse Transcriptase (New England Biolabs) for 2 hours at 42° C. in 1× M-MuLV Reverse Transcriptase buffer, supplemented with 10 mM DTT, 5 mM dNTPs, 0.1% Tween-20 and SUPERaseIN. After reverse transcription the double stranded RNA-cDNA hybrids were stained with 10 nM SYTOX Orange dye (Invitrogen), an intercalator that is selective for double-stranded DNA, and incubated for 5 mins prior to imaging.

The epifluorescence imaging system was constructed on an inverted Nikon Eclipse Ti-U microscope with 20×, 0.75 NA air objective (Plan Apo X, Nikon). SYTOX Orange was excited using a 532 nm diode-pumped solid state laser (Dragon Lasers), and the fluorescence was collected and imaged onto an electron multiplying charge coupled device (EMCCD) camera (iXON3, Andor Technologies). The images were acquired with 0.5 s exposure time (controlled by external shutter) at 1 MHz digitization (with no EM gain). Automated scanning of the surface (motorized X-Y stage, ASI), image acquisition, and illumination were controlled with custom software written in C/C++. The images were analyzed using ImageJ software.

Microfluidic Device for Single Cell RNA-Seq

For the single cell RNA-Seq experiment a monolithic PDMS was designated based multi-channel device, by fabricating each channel with a microwell array. Two key soft lithography techniques were used to fabricate this device. First, instead of using silicon wafer master directly for fabricating the microwell array as done in the case of RNA printing device, we generated a secondary master made out of PDMS. This was done because the aspect ratio of the micropillars results in a relatively fragile silicon master. It was found that the PDMS master to be more durable. Second, instead of using a double-sided adhesive tape for the device assembly, the bottom and the top of the device were bonded together by partial curing. This provided us with more durable and reliable partitions between the individual channels of our device than could be generated using tape. For the multi-lane microfluidic device, two different silicon wafer masters were fabricated, one for the top and other for the bottom containing the array of microwells. Masters for soft lithography were generated from 4-inch silicon test wafers (University Wafer) coated with SU-8 2005 (MicroChem) photoresist. The wafer master for the bottom of the device contained five arrays of cylindrical pillars (diameter 50 micron; height 50 micron). The wafer was then fluorosilanized as described above. To avoid repeated use of the silicon wafer, we fabricated secondary masters in PDMS as follows. 40 g of degassed PDMS 10:1 (base:curing agent) was poured and cured on the wafer, and then peeled off and cut into a rectangular slab. The surface containing an array of microwells was oxidized in plasma chamber (Harrick Plasma) for ~2 mins and immediately fluorosilanized. Using this microwell-containing slab as a master, ~10 g of degassed PDMS was cured on it and peeled off. This new PDMS slab containing array of pillars is an exact replica of the silicon wafer, and is fluorosilanized and served as a secondary master for soft lithography for microfabrication of the bottom part of the microfluidic flowcell device. ~2 g of degassed PDMS 10:1 (base:curing agent) was poured on a plasma cleaned glass slide and the secondary master with pillar array was placed gently with pillars immersed into the liquid PDMS. The slide, PDMS and master (on top) was degassed for ~5 mins and then cured hard at 90° C. for 2 hours. After curing, the master is peeled off and a thin layer of PDMS is bonded to the glass slide with 5 lane arrays of microwells.

A second silicon wafer master was constructed containing five longitudinal ridges (with a height of 100 microns) with rounded ends on which ~30 g of degassed PDMS 15:1 (base:curing agent) was poured and allowed to cure partially at 60° C. for 90 mins. The partially cured PDMS was cut into a slab, holes were punched at either end of each channel, and the slab was placed gently on the top of the glass slide containing the microwell array in such a way that the longitudinal grooves were aligned over each of the five microwell arrays. The slide assembly was then incubated at 90° C. overnight to form a single monolithic PDMS structure as shown in FIG. 5A.

Synthesis of Uniquely Barcoded Beads for mRNA Capture

N-succinimide-coated Sepharose beads with a mean diameter of ~30 µm were obtained from GE Healthcare in isopropanol. The beads were washed three times with water by centrifugation and re-suspended in a reaction mixture with a final concentration of 100 mM sodium borate (pH 8.5) and ~0.8 mg/mL streptavidin (streptavidin from New England BioLabs was spiked with ~2% AlexaFluor 647-labeled streptavidin from Life Technologies). The reaction was incubated at room temperature for one hour on a rotisserie to allow the streptavidin to covalently attach to the beads. The beads were then washed five times in Wash Buffer and incubated in 1 Wash Buffer for 30 minutes before using to completely quench any remaining reactive groups on the beads.

A dual-biotinylated oligonucleotide containing both the T7 promoter sequence and a partial Illumina adapter sequence (Table 1) were annealed to each of 96 oligonucleotides (Table 2) that are complementary to the partial Illumina adapter sequence on the 3'-end and contain a unique barcode and universal anchor sequence on the 5'-end (FIGS. 3A and 3B). Table 1 describes a list of oligonucleotides used for barcoding and library preparation in additional to list of cell-identifying barcodes in Table 2 for Experiment 1.

TABLE 1

| Oligonucleotide Name | Oligonucleotide Sequence | SEQ ID NO: |
|---|---|---|
| Bead Capture Oligo (5'-dual biotinylated) | AGGTAAGGTAATACGACTCACTATAGGG GTTCAGAGTTCTACAGTCCGACGATC | 9464 |
| RT1 (Reverse Transcription Primer for Lane 1) | GCCTTGGCACCCGAGAATTCCANNNNNN NNCGTGATNNNNNN | 9465 |
| RT2 (Reverse Transcription Primer for Lane 2) | GCCTTGGCACCCGAGAATTCCANNNNNN NNACATCGNNNNNN | 9466 |
| RT3 (Reverse Transcription Primer for Lane 3) | GCCTTGGCACCCGAGAATTCCANNNNNN NNGCCTAANNNNNN | 9467 |
| RT4 (Reverse Transcription Primer for Lane 4) | GCCTTGGCACCCGAGAATTCCANNNNNN NNTGGTCANNNNNN | 9468 |
| RT5 (Reverse Transcription Primer for Lane 5) | GCCTTGGCACCCGAGAATTCCANNNNNN NNCACTGTNNNNNN | 9469 |
| RP1 (PCR Primer 1) | AATGATACGGCGACCACCGAGATCTACA CGTTCAGAGTTCTACAGTCCGA | 9470 |
| RPI1 (PCR Primer 2) | CAAGCAGAAGACGGCATACGAGATCGTG ATGTGACTGGAGTTCCTTGGCACCCGAG AATTCCA | 9471 |

TABLE 2

| Oligonucleotide Name | Oligonucleotide Sequence | SEQ ID NO: |
|---|---|---|
| FBC_Oligo1 | CAGGTCAACCAGAGAGATCGTCGGACTGTAGAACTCTGAAC | 9472 |
| FBC_Oligo2 | CAGGTCAAAGTACGCGATCGTCGGACTGTAGAACTCTGAAC | 9473 |
| FBC_Oligo3 | CAGGTCGTTTGGCATGATCGTCGGACTGTAGAACTCTGAAC | 9474 |
| FBC_Oligo4 | CAGGTCAAGTGAGGTGATCGTCGGACTGTAGAACTCTGAAC | 9475 |
| FBC_Oligo5 | CAGGTCACGTTAGCTGATCGTCGGACTGTAGAACTCTGAAC | 9476 |
| FBC_Oligo6 | CAGGTCGTGCTAGAGGATCGTCGGACTGTAGAACTCTGAAC | 9477 |
| FBC_Oligo7 | CAGGTCGTCCTGTGTGATCGTCGGACTGTAGAACTCTGAAC | 9478 |
| FBC_Oligo8 | CAGGTCTCTACGGCAGATCGTCGGACTGTAGAACTCTGAAC | 9479 |
| FBC_Oligo9 | CAGGTCACAGGGCTTGATCGTCGGACTGTAGAACTCTGAAC | 9480 |
| FBC_Oligo10 | CAGGTCGTGCGTTATGATCGTCGGACTGTAGAACTCTGAAC | 9481 |
| FBC_Oligo11 | CAGGTCGGGTAAGTAGATCGTCGGACTGTAGAACTCTGAAC | 9482 |
| FBC_Oligo12 | CAGGTCTCCCTTAGGGATCGTCGGACTGTAGAACTCTGAAC | 9483 |
| FBC_Oligo13 | CAGGTCCAAGTTGGTGATCGTCGGACTGTAGAACTCTGAAC | 9484 |
| FBC_Oligo14 | CAGGTCTTCTCACTCGATCGTCGGACTGTAGAACTCTGAAC | 9485 |
| FBC_Oligo15 | CAGGTCTCCCACTCTGATCGTCGGACTGTAGAACTCTGAAC | 9486 |
| FBC_Oligo16 | CAGGTCCGGTATACCGATCGTCGGACTGTAGAACTCTGAAC | 9487 |
| FBC_Oligo17 | CAGGTCAGGCATGTGGATCGTCGGACTGTAGAACTCTGAAC | 9488 |
| FBC_Oligo18 | CAGGTCCCCAGATTGGATCGTCGGACTGTAGAACTCTGAAC | 9489 |
| FBC_Oligo19 | CAGGTCTTCCCTTGAGATCGTCGGACTGTAGAACTCTGAAC | 9490 |
| FBC_Oligo20 | CAGGTCGTTGTACGAGATCGTCGGACTGTAGAACTCTGAAC | 9491 |
| FBC_Oligo21 | CAGGTCTGCTTGCAGGATCGTCGGACTGTAGAACTCTGAAC | 9492 |
| FBC_Oligo22 | CAGGTCGGCCTCATTGATCGTCGGACTGTAGAACTCTGAAC | 9493 |
| FBC_Oligo23 | CAGGTCAACAGCCTAGATCGTCGGACTGTAGAACTCTGAAC | 9494 |
| FBC_Oligo24 | CAGGTCGATGCAATGGATCGTCGGACTGTAGAACTCTGAAC | 9495 |
| FBC_Oligo25 | CAGGTCGAAGGAACGGATCGTCGGACTGTAGAACTCTGAAC | 9496 |
| FBC_Oligo26 | CAGGTCCAGCCACTTGATCGTCGGACTGTAGAACTCTGAAC | 9497 |
| FBC_Oligo27 | CAGGTCCTCTGCTTCGATCGTCGGACTGTAGAACTCTGAAC | 9498 |
| FBC_Oligo28 | CAGGTCGGCTTATGAGATCGTCGGACTGTAGAACTCTGAAC | 9499 |
| FBC_Oligo29 | CAGGTCCTAGTCCTCGATCGTCGGACTGTAGAACTCTGAAC | 9500 |
| FBC_Oligo30 | CAGGTCCTAGAGGAGGATCGTCGGACTGTAGAACTCTGAAC | 9501 |
| FBC_Oligo31 | CAGGTCAGCTTTACCGATCGTCGGACTGTAGAACTCTGAAC | 9502 |
| FBC_Oligo32 | CAGGTCGTCCATGAAGATCGTCGGACTGTAGAACTCTGAAC | 9503 |
| FBC_Oligo33 | CAGGTCCTCGAACCTGATCGTCGGACTGTAGAACTCTGAAC | 9504 |
| FBC_Oligo34 | CAGGTCCATTGTACGGATCGTCGGACTGTAGAACTCTGAAC | 9505 |
| FBC_Oligo35 | CAGGTCTTGAACGCTGATCGTCGGACTGTAGAACTCTGAAC | 9506 |
| FBC_Oligo36 | CAGGTCTACGTCATGGATCGTCGGACTGTAGAACTCTGAAC | 9507 |
| FBC_Oligo37 | CAGGTCAAGCCGTTAGATCGTCGGACTGTAGAACTCTGAAC | 9508 |
| FBC_Oligo38 | CAGGTCCGGACGTATGATCGTCGGACTGTAGAACTCTGAAC | 9509 |
| FBC_Oligo39 | CAGGTCTCGTTACCGGATCGTCGGACTGTAGAACTCTGAAC | 9510 |

TABLE 2-continued

| Oligonucleotide Name | Oligonucleotide Sequence | SEQ ID NO: |
|---|---|---|
| FBC_Oligo40 | CAGGTCATCCCCCATGATCGTCGGACTGTAGAACTCTGAAC | 9511 |
| FBC_Oligo41 | CAGGTCCAGACGATTGATCGTCGGACTGTAGAACTCTGAAC | 9512 |
| FBC_Oligo42 | CAGGTCATCGATCCCGATCGTCGGACTGTAGAACTCTGAAC | 9513 |
| FBC_Oligo43 | CAGGTCCCTGAGGATGATCGTCGGACTGTAGAACTCTGAAC | 9514 |
| FBC_Oligo44 | CAGGTCAGCTCTTTGGATCGTCGGACTGTAGAACTCTGAAC | 9515 |
| FBC_Oligo45 | CAGGTCGGAATACGGGATCGTCGGACTGTAGAACTCTGAAC | 9516 |
| FBC_Oligo46 | CAGGTCCTATCCTGGGATCGTCGGACTGTAGAACTCTGAAC | 9517 |
| FBC_Oligo47 | CAGGTCGGTTGTAGTGATCGTCGGACTGTAGAACTCTGAAC | 9518 |
| FBC_Oligo48 | CAGGTCGAACGTAGCGATCGTCGGACTGTAGAACTCTGAAC | 9519 |
| FBC_Oligo49 | CAGGTCGTCTATCGGATCGTCGGACTGTAGAACTCTGAAC | 9520 |
| FBC_Oligo50 | CAGGTCTACGAGTGGATCGTCGGACTGTAGAACTCTGAAC | 9521 |
| FBC_Oligo51 | CAGGTCTCATGTCGGATCGTCGGACTGTAGAACTCTGAAC | 9522 |
| FBC_Oligo52 | CAGGTCAAACACCCGATCGTCGGACTGTAGAACTCTGAAC | 9523 |
| FBC_Oligo53 | CAGGTCACTAGTCCGATCGTCGGACTGTAGAACTCTGAAC | 9524 |
| FBC_Oligo54 | CAGGTCCGAGGAATGATCGTCGGACTGTAGAACTCTGAAC | 9525 |
| FBC_Oligo55 | CAGGTCACAATGGCGATCGTCGGACTGTAGAACTCTGAAC | 9526 |
| FBC_Oligo56 | CAGGTCTAGGTCTCGATCGTCGGACTGTAGAACTCTGAAC | 9527 |
| FBC_Oligo57 | CAGGTCTCTGTGAGGATCGTCGGACTGTAGAACTCTGAAC | 9528 |
| FBC_Oligo58 | CAGGTCGGGATTGAGATCGTCGGACTGTAGAACTCTGAAC | 9529 |
| FBC_Oligo59 | CAGGTCAACTCTGGGATCGTCGGACTGTAGAACTCTGAAC | 9530 |
| FBC_Oligo60 | CAGGTCAAACGCGTGATCGTCGGACTGTAGAACTCTGAAC | 9531 |
| FBC_Oligo61 | CAGGTCTCCTACGAGATCGTCGGACTGTAGAACTCTGAAC | 9532 |
| FBC_Oligo62 | CAGGTCTAGCAGGTGATCGTCGGACTGTAGAACTCTGAAC | 9533 |
| FBC_Oligo63 | CAGGTCCCTGCATTGATCGTCGGACTGTAGAACTCTGAAC | 9534 |
| FBC_Oligo64 | CAGGTCGTGATGCAGATCGTCGGACTGTAGAACTCTGAAC | 9535 |
| FBC_Oligo65 | CAGGTCCGATTCAGGATCGTCGGACTGTAGAACTCTGAAC | 9536 |
| FBC_Oligo66 | CAGGTCAGGATGACGATCGTCGGACTGTAGAACTCTGAAC | 9537 |
| FBC_Oligo67 | CAGGTCAGGCCATAGATCGTCGGACTGTAGAACTCTGAAC | 9538 |
| FBC_Oligo68 | CAGGTCGCTTGCTTGATCGTCGGACTGTAGAACTCTGAAC | 9539 |
| FBC_Oligo69 | CAGGTCTCCCAAGTGATCGTCGGACTGTAGAACTCTGAAC | 9540 |
| FBC_Oligo70 | CAGGTCTCAAGGCAGATCGTCGGACTGTAGAACTCTGAAC | 9541 |
| FBC_Oligo71 | CAGGTCACGAGGTAGATCGTCGGACTGTAGAACTCTGAAC | 9542 |
| FBC_Oligo72 | CAGGTCGGAACGAAGATCGTCGGACTGTAGAACTCTGAAC | 9543 |
| FBC_Oligo73 | CAGGTCAATCCCAGGATCGTCGGACTGTAGAACTCTGAAC | 9544 |
| FBC_Oligo74 | CAGGTCCGATAAGGGATCGTCGGACTGTAGAACTCTGAAC | 9545 |
| FBC_Oligo75 | CAGGTCTATCGCGAGATCGTCGGACTGTAGAACTCTGAAC | 9546 |
| FBC_Oligo76 | CAGGTCCGCATAACGATCGTCGGACTGTAGAACTCTGAAC | 9547 |
| FBC_Oligo77 | CAGGTCGTGCAGTTGATCGTCGGACTGTAGAACTCTGAAC | 9548 |

TABLE 2-continued

| Oligonucleotide Name | Oligonucleotide Sequence | SEQ ID NO: |
|---|---|---|
| FBC_Oligo78 | CAGGTCAGAACGCTGATCGTCGGACTGTAGAACTCTGAAC | 9549 |
| FBC_Oligo79 | CAGGTCTAGAGGTCGATCGTCGGACTGTAGAACTCTGAAC | 9550 |
| FBC_Oligo80 | CAGGTCCTGTGATGGATCGTCGGACTGTAGAACTCTGAAC | 9551 |
| FBC_Oligo81 | CAGGTCTAGAGCCAGATCGTCGGACTGTAGAACTCTGAAC | 9552 |
| FBC_Oligo82 | CAGGTCCTTGATGCGATCGTCGGACTGTAGAACTCTGAAC | 9553 |
| FBC_Oligo83 | CAGGTCTTCGTGTCGATCGTCGGACTGTAGAACTCTGAAC | 9554 |
| FBC_Oligo84 | CAGGTCTATCTGCGGATCGTCGGACTGTAGAACTCTGAAC | 9555 |
| FBC_Oligo85 | CAGGTCTGGTAGGAGATCGTCGGACTGTAGAACTCTGAAC | 9556 |
| FBC_Oligo86 | CAGGTCCCTAGACAGATCGTCGGACTGTAGAACTCTGAAC | 9557 |
| FBC_Oligo87 | CAGGTCAGTCAACGGATCGTCGGACTGTAGAACTCTGAAC | 9558 |
| FBC_Oligo88 | CAGGTCAAGGGTGAGATCGTCGGACTGTAGAACTCTGAAC | 9559 |
| FBC_Oligo89 | CAGGTCCTTCACACGATCGTCGGACTGTAGAACTCTGAAC | 9560 |
| FBC_Oligo90 | CAGGTCAGGTTGCTGATCGTCGGACTGTAGAACTCTGAAC | 9561 |
| FBC_Oligo91 | CAGGTCACCCGAAAGATCGTCGGACTGTAGAACTCTGAAC | 9562 |
| FBC_Oligo92 | CAGGTCGAAAAGGGGATCGTCGGACTGTAGAACTCTGAAC | 9563 |
| FBC_Oligo93 | CAGGTCACTTCCCAGATCGTCGGACTGTAGAACTCTGAAC | 9564 |
| FBC_Oligo94 | CAGGTCTGCTGCATGATCGTCGGACTGTAGAACTCTGAAC | 9565 |
| FBC_Oligo95 | CAGGTCATTCCTGGGATCGTCGGACTGTAGAACTCTGAAC | 9566 |
| FBC_Oligo96 | CAGGTCCAGAACTCGATCGTCGGACTGTAGAACTCTGAAC | 9567 |

Table 2 describes a list of ooligonucleotide sequences used to generate the first set of barcoded beads (FBC) for combinatorial synthesis in Experiment 1.

The dual-biotinylated oligonucleotide was annealed at a final concentration of 2 µM in the presence of a four-fold molar excess of the barcoded oligonucleotide in a 96-well plate by stepwise cooling from 85° C. to 30° C. over 30 minutes. A DNA polymerase master mix was then added to each well such that the final concentration of the reaction components was 1×NEB Buffer 2 (New England BioLabs), 0.25 U/µL Klenow Fragment (exo-) (New England BioLabs), and 0.5 mM dNTPs. The reaction was incubated in each well at 37 C for 30 minutes before heat inactivating the polymerase at 75° C. for 20 minutes.

An equal volume of beads was then added to each reaction mixture so that the extended, dual-biotinylated oligonucleotide could conjugate to the streptavidin coated beads at a final density of ~1 billion oligonucleotide primers per bead. The conjugation reaction was incubated at room temperature overnight on a rotisserie and quenched with biotin at a final concentration of 2 mM and sodium hydroxide at a final concentration of 125 mM to melt the template strand off of the beads. The beads were then pooled and washed five times in 125 mM sodium hydroxide supplemented with 0.1 mM biotin and then washed an additional three times with Wash Buffer and 0.1 mM biotin. The beads were then re-suspended in Hybridization Buffer (20 mM Tris pH 8.0, 1 M NaCl, 0.1% Tween-20) supplemented with 0.1 mM biotin.

The pooled beads were split into ten reactions to which one of ten partially complementary oligonucleotides (Table 3) each containing a specific second barcode was added at a final concentration of 5 µM. The second barcode-containing oligonucleotides were allowed to hybridize to the beads at room temperature overnight on a rotisserie.

TABLE 3

| Oligonucleotide Name | Oligonucleotide Sequence | SEQ ID NO: |
|---|---|---|
| SBC_Oligo1 | AAAAAAAAAAAAAAAAAAAAAAAAAGGTGATACAG GTCAAAAAAAAAGATCGTCGGACTGTAGAACTC | 9568 |
| SBC_Oligo2 | AAAAAAAAAAAAAAAAAAAAAAAATGAATGCCAG GTCAAAAAAAAAGATCGTCGGACTGTAGAACTC | 9569 |
| SBC_Oligo3 | AAAAAAAAAAAAAAAAAAAAAAAATGCCAAACAG GTCAAAAAAAAAGATCGTCGGACTGTAGAACTC | 9570 |

TABLE 3-continued

| Oligonucleotide Name | Oligonucleotide Sequence | SEQ ID NO: |
|---|---|---|
| SBC_Oligo4 | AAAAAAAAAAAAAAAAAAAAAAAAACAGAAGCAGGTCAAAAAAAAAGATCGTCGGACTGTAGAACTC | 9571 |
| SBC_Oligo5 | AAAAAAAAAAAAAAAAAAAAAAAAACACTGGACAGGTCAAAAAAAAAGATCGTCGGACTGTAGAACTC | 9572 |
| SBC_Oligo6 | AAAAAAAAAAAAAAAAAAAAAAAAACGATGATCAGGTCAAAAAAAAAGATCGTCGGACTGTAGAACTC | 9573 |
| SBC_Oligo7 | AAAAAAAAAAAAAAAAAAAAAAAAAGTGTCCACAGGTCAAAAAAAAAGATCGTCGGACTGTAGAACTC | 9574 |
| SBC_Oligo8 | AAAAAAAAAAAAAAAAAAAAAAAAATCCTCTTCAGGTCAAAAAAAAAGATCGTCGGACTGTAGAACTC | 9575 |
| SBC_Oligo9 | AAAAAAAAAAAAAAAAAAAAAAAAAGTGCAGTCAGGTCAAAAAAAAAGATCGTCGGACTGTAGAACTC | 9576 |
| SBC_Oligo10 | AAAAAAAAAAAAAAAAAAAAAAAAAGGTAGACAGGTCAAAAAAAAAGATCGTCGGACTGTAGAACTC | 9577 |

Table 3 describes oligonucleotide sequences used to generate the second set of barcoded beads (SBC) for combinatorial synthesis in Experiment 1.

The beads were then washed five times in Wash Buffer supplemented with 0.1 mM biotin and then re-suspended in a reaction mixture with final concentrations of 0.5 mM dNTPs, 1×NEB Buffer 2 (New England BioLabs), and 0.1 mM biotin. We included biotin in the wash and storage buffers in order to saturate any remaining streptavidin sites on the beads so that, in the even that a barcoded capture primer dissociates form a beads, it cannot re-associate with a different bead. The reactions were cooled to 16° C. on a thermocycler and Klenow Fragment (exo-) (New England BioLabs) was added at a final concentration of 0.25 U/μL. The reaction was incubated for one hour at 16° C. with mixing every 10 minutes with a pipette followed by heat inactivation at 75° C. for 20 minutes.

The ten reaction mixtures were then quenched and the hybridized strand was denatured by addition of sodium hydroxide to a final concentration of 125 mM. The reaction mixtures were then washed five times in 125 mM sodium hydroxide with 0.1 mM biotin, pooled, and then further washed three times with Wash Buffer supplemented with 0.1 mM biotin.

Procedure for Single Cell RNA-Seq Experiment 1

Prior to the experiment, each lane of the device was flushed with 0.1% Tween-20 solution and incubated for several hours to hydrate the microwells, which were subsequently washed with 2 mL of phosphate-buffered saline (PBS). Cell suspensions were counted using Countess automated cell counter (Life Technologies). A suspension of cells in PBS mixed with Calcein AM (live stain) dye was flowed in to each lane and incubated for ~5 mins, so that the cells load in to the microwells under gravity. After thoroughly washing out the excess cells with PBS, a suspension of barcoded capture beads that had been pre-counted by microscopy was introduced in PBS and allowed to load under gravity for ~5 mins. In an aspect, ~3,000 cells to each lane of the device was introduced. It is also noted that only 25% of the lower surface of each channel contains a microwell array, and so by expanding this area, the number of cells captured without incurring increased reagent costs for on-chip library generation were significantly increased (for example, as long as the size of the barcode pool was pooled). Excess beads were washed out thoroughly with PBS and the flow cell was incubated on ice. 20 μL 0.08% TritonX-100 (Sigma) supplemented with SUPERaseIN in PBS was flowed under ice-cold conditions immediately followed by fluorinert oil (Sigma) to seal the device. After two cycles of freeze-thaw at −80° C. to enhance cell lysis, the device was incubated at room temperature for 60 mins for mRNA capture (FIG. 2A).

Two of the lanes contained pure U87 and MCF10a cells, respectively, and other lanes were loaded with a mixture of both the cell types. All lanes were imaged twice, first with blue laser ($\lambda_{ex}$=473 nm, Dragon Lasers) for imaging the cells and secondly with a red laser ($\lambda_{ex}$=637 nm, Obis, Coherent) for imaging the beads labeled with AlexaFluor 647 tagged streptavidin. We used the two-color images to determine number of bead-cell pairs in the array. After an hour of incubation for mRNA capture, all the lanes were unsealed by rapid washing of the oil with 20 mM Tris, containing 1% TritonX-100 and SUPERaseIN, followed by Wash Buffer supplemented with SUPERaseIN. After this point the microwells stay open and subsequent enzymatic steps occur simultaneously in separate lanes of the open device.

The single cell library preparation protocol is adopted from the recently reported CEL-Seq protocol with few modifications as described below. The mRNA captured on the beads was reverse transcribed using ProtoScript II Reverse Transcriptase (New England Biolabs) for 2 hours at 42° C. in 1× ProtoScript Reverse Transcriptase buffer, supplemented with 10 mM DTT, 0.5 mM dNTPs, 0.1% Tween-20 and SUPERaseIN. The reaction mixture was washed out with Wash Buffer. The second strand synthesis was carried out using reagents from the MessageAmp II aRNA amplification kit (Ambion), where a mixture of DNA polymerase and RNaseH in second strand buffer was used along with dNTPs by incubating the device at 16° C. for 2 hours. After flushing out the second strand reaction mixture with Wash Buffer, an in vitro transcription mixture from the MessageAmp II kit containing four nucleotides and T7 RNA polymerase enzyme mix in T7 buffer was introduced to all lanes and incubated for 13 hours at 37° C. (FIGS. 5A-5C). The reaction linearly amplified our cDNA, eluting pools of barcoded aRNA into the flow channels of the device which was then removed from each lane using a pipette and purified separately using RNA Clean & Concentrator columns (Zymo) and eluted into five separate tubes. The aRNA from the 5 lanes was reverse transcribed separately using random hexamers tagged with five different barcodes and 8-base UMIs to differentiate cDNA for all five lanes and part of an Illumina sequencing adapter. The aRNA along with the hexamer primers was heated to 70° C. for 2 mins and immediately placed on ice for 5 mins. The reverse transcription mix containing PrimeScript Reverse Transcriptase (Clontech-Takara), 0.5 mM dNTPs, 10 mM DTT, 1× PrimeScript buffer supplemented with SUPERaseIN was added and incubated at 25° C. for 10 mins followed by 2 hour incubation at 42° C. The RNA-cDNA hybrid product was purified twice using 0.65× ratio of Agencourt Ampure beads (Beckman Coulter) and the purified cDNA from all the lanes were pooled together for PCR. Phusion High Fidelity DNA polymerase (New England Biolabs) was used for amplifying the cDNA using RP1 and RPI Illumina primers in 1× PhusionHF buffer supplemented with dNTPs. The PCR product was purified on a 1.5% agarose gel which was stained with SybrGold (Life Technologies) before being cut between 400-800 bp. The library was extracted from the gel using Gel Extraction kit (Qiagen), and further purified and concentrated using a 0.65× ratio of the AMpure beads (Beckman Coulter). The final library was quantified using a Qubit (Life Technologies) and Bioanalyzer (Agilent) and sequenced on NextSeq 500 desktop sequencer (Illumina). ~240 million paired-end reads with a 26-base first read and a 66-base second read were obtained.

Procedure for Single Cell RNA-Seq Experiment 2

Experiment 2 was identical to Experiment 1 with a few exceptions. First, the two cell types under study were U87 human glioma cells and WI-38 human fibroblast cells (a diploid, limited-passage, non-cancer cell line). Second, reagents from the HiScribe In Vitro Transcription kit (New England BioLabs) were substituted for the MessageAmp II kit for the IVT portion of the protocol. Third, some of the oligonucleotides used were different from in Experiment 1 and are tabulated as detailed in Tables 4-6.

Table 4 describes a group of preferred oligonucleotides used for barcoding and library preparation for Experiment 2.

TABLE 4

| Oligonucleotide Name | Oligonucleotide Sequence | SEQ ID NO: |
| --- | --- | --- |
| Bead Capture Oligo (5'-dual biotinylated) | AGGTAAGGTAATACGACTCACTATAGGGGTTCAGAGTTCTACAGTCCGACGATC | 9578 |
| RT1 (Reverse Transcription Primer for Lane 1) | GCCTTGGCACCCGAGAATTCCANNNNNNNNCGTCATNNNNNN | 9579 |
| RT2 (Reverse Transcription Primer for Lane 2) | GCCTTGGCACCCGAGAATTCCANNNNNNNNTACCCANNNNNN | 9580 |
| RT3 (Reverse Transcription Primer for Lane 3) | GCCTTGGCACCCGAGAATTCCANNNNNNNNGCCATTNNNNNN | 9581 |
| RT4 (Reverse Transcription Primer for Lane 4) | GCCTTGGCACCCGAGAATTCCANNNNNNNNGAGTACNNNNNN | 9582 |
| RT5 (Reverse Transcription Primer for Lane 5) | GCCTTGGCACCCGAGAATTCCANNNNNNNNAGAGTCNNNNNN | 9583 |
| RP1 (PCR Primer 1) | AATGATACGGCGACCACCGAGATCTACACGTTCAGAGTTCTACAGTCCGA | 9584 |
| RPI2 (PCR Primer 2) | CAAGCAGAAGACGGCATACGAGATACATCGGTGACTGGAGTTCCTTGGCACCCGAGAATTCCA | 9585 |

Table 5 describes oligonucleotide sequences used to generate the first set of barcoded beads (FBC) for combinatorial synthesis in Experiment 2.

TABLE 5

| Oligonucleotide Name | Oligonucleotide Sequence | SEQ ID NO: |
| --- | --- | --- |
| FBC_Oligo1 | CAGGTCCTGATCGATGATCGTCGGACTGTAGAACTCTGAAC | 9586 |
| FBC_Oligo2 | CAGGTCGTGTAGACAGATCGTCGGACTGTAGAACTCTGAAC | 9587 |
| FBC_Oligo3 | CAGGTCCATTGTTCCGATCGTCGGACTGTAGAACTCTGAAC | 9588 |

TABLE 5-continued

| Oligonucleotide Name | Oligonucleotide Sequence | SEQ ID NO: |
|---|---|---|
| FBC_Oligo4 | CAGGTCCTTGACTACGATCGTCGGACTGTAGAACTCTGAAC | 9589 |
| FBC_Oligo5 | CAGGTCACCGTTTCGGATCGTCGGACTGTAGAACTCTGAAC | 9590 |
| FBC_Oligo6 | CAGGTCAAGGACCGTGATCGTCGGACTGTAGAACTCTGAAC | 9591 |
| FBC_Oligo7 | CAGGTCTCACTATGCGATCGTCGGACTGTAGAACTCTGAAC | 9592 |
| FBC_Oligo8 | CAGGTCCTGCAATGGGATCGTCGGACTGTAGAACTCTGAAC | 9593 |
| FBC_Oligo9 | CAGGTCTGAGTCGTCGATCGTCGGACTGTAGAACTCTGAAC | 9594 |
| FBC_Oligo10 | CAGGTCCTCACACTAGATCGTCGGACTGTAGAACTCTGAAC | 9595 |
| FBC_Oligo11 | CAGGTCTTACCCCCTGATCGTCGGACTGTAGAACTCTGAAC | 9596 |
| FBC_Oligo12 | CAGGTCCCAAGTAGAGATCGTCGGACTGTAGAACTCTGAAC | 9597 |
| FBC_Oligo13 | CAGGTCATAGCGCACGATCGTCGGACTGTAGAACTCTGAAC | 9598 |
| FBC_Oligo14 | CAGGTCTGACGTACGGATCGTCGGACTGTAGAACTCTGAAC | 9599 |
| FBC_Oligo15 | CAGGTCGTAGAGTTGGATCGTCGGACTGTAGAACTCTGAAC | 9600 |
| FBC_Oligo16 | CAGGTCTTTCTGGCGGATCGTCGGACTGTAGAACTCTGAAC | 9601 |
| FBC_Oligo17 | CAGGTCGGAATGTGTGATCGTCGGACTGTAGAACTCTGAAC | 9602 |
| FBC_Oligo18 | CAGGTCCTATGGAAGGATCGTCGGACTGTAGAACTCTGAAC | 9603 |
| FBC_Oligo19 | CAGGTCAAGTCCATGGATCGTCGGACTGTAGAACTCTGAAC | 9604 |
| FBC_Oligo20 | CAGGTCAGTACTTGGGATCGTCGGACTGTAGAACTCTGAAC | 9605 |
| FBC_Oligo21 | CAGGTCACAGGACTAGATCGTCGGACTGTAGAACTCTGAAC | 9606 |
| FBC_Oligo22 | CAGGTCACCAGGTAAGATCGTCGGACTGTAGAACTCTGAAC | 9607 |
| FBC_Oligo23 | CAGGTCGCATGAACCGATCGTCGGACTGTAGAACTCTGAAC | 9608 |
| FBC_Oligo24 | CAGGTCGTTGGTGTTGATCGTCGGACTGTAGAACTCTGAAC | 9609 |
| FBC_Oligo25 | CAGGTCCCTTCAGACGATCGTCGGACTGTAGAACTCTGAAC | 9610 |
| FBC_Oligo26 | CAGGTCCCTCTTGGTGATCGTCGGACTGTAGAACTCTGAAC | 9611 |
| FBC_Oligo27 | CAGGTCGGGAAAGTTGATCGTCGGACTGTAGAACTCTGAAC | 9612 |
| FBC_Oligo28 | CAGGTCAGCCAGAGTGATCGTCGGACTGTAGAACTCTGAAC | 9613 |
| FBC_Oligo29 | CAGGTCTCGCATCTGGATCGTCGGACTGTAGAACTCTGAAC | 9614 |
| FBC_Oligo30 | CAGGTCGATACGGCAGATCGTCGGACTGTAGAACTCTGAAC | 9615 |
| FBC_Oligo31 | CAGGTCTCGGCCAAAGATCGTCGGACTGTAGAACTCTGAAC | 9616 |
| FBC_Oligo32 | CAGGTCAGATTTCGCGATCGTCGGACTGTAGAACTCTGAAC | 9617 |
| FBC_Oligo33 | CAGGTCGACCCTCAAGATCGTCGGACTGTAGAACTCTGAAC | 9618 |
| FBC_Oligo34 | CAGGTCAGTCCACTCGATCGTCGGACTGTAGAACTCTGAAC | 9619 |
| FBC_Oligo35 | CAGGTCCAAACGATCGATCGTCGGACTGTAGAACTCTGAAC | 9620 |
| FBC_Oligo36 | CAGGTCGCCTAATAGGATCGTCGGACTGTAGAACTCTGAAC | 9621 |
| FBC_Oligo37 | CAGGTCGGCTACATCGATCGTCGGACTGTAGAACTCTGAAC | 9622 |
| FBC_Oligo38 | CAGGTCTATGAGCAGGATCGTCGGACTGTAGAACTCTGAAC | 9623 |
| FBC_Oligo39 | CAGGTCGGTAGTAACGATCGTCGGACTGTAGAACTCTGAAC | 9624 |
| FBC_Oligo40 | CAGGTCCGCGTATATGATCGTCGGACTGTAGAACTCTGAAC | 9625 |
| FBC_Oligo41 | CAGGTCTACTGGAGCGATCGTCGGACTGTAGAACTCTGAAC | 9626 |

TABLE 5-continued

| Oligonucleotide Name | Oligonucleotide Sequence | SEQ ID NO: |
|---|---|---|
| FBC_Oligo42 | CAGGTCAGGGAATCAGATCGTCGGACTGTAGAACTCTGAAC | 9627 |
| FBC_Oligo43 | CAGGTCATCCGAGATGATCGTCGGACTGTAGAACTCTGAAC | 9628 |
| FBC_Oligo44 | CAGGTCTCCCAAGCAGATCGTCGGACTGTAGAACTCTGAAC | 9629 |
| FBC_Oligo45 | CAGGTCGAGCCGTTTGATCGTCGGACTGTAGAACTCTGAAC | 9630 |
| FBC_Oligo46 | CAGGTCTGCTCTTACGATCGTCGGACTGTAGAACTCTGAAC | 9631 |
| FBC_Oligo47 | CAGGTCACGACTACCGATCGTCGGACTGTAGAACTCTGAAC | 9632 |
| FBC_Oligo48 | CAGGTCCAAGCAGCTGATCGTCGGACTGTAGAACTCTGAAC | 9633 |
| FBC_Oligo49 | CAGGTCGTATTCGCGATCGTCGGACTGTAGAACTCTGAAC | 9634 |
| FBC_Oligo50 | CAGGTCGCTCTGAAGATCGTCGGACTGTAGAACTCTGAAC | 9635 |
| FBC_Oligo51 | CAGGTCACGTAGTGGATCGTCGGACTGTAGAACTCTGAAC | 9636 |
| FBC_Oligo52 | CAGGTCATTGGGTCGATCGTCGGACTGTAGAACTCTGAAC | 9637 |
| FBC_Oligo53 | CAGGTCAACAGCACGATCGTCGGACTGTAGAACTCTGAAC | 9638 |
| FBC_Oligo54 | CAGGTCTCAGAGACGATCGTCGGACTGTAGAACTCTGAAC | 9639 |
| FBC_Oligo55 | CAGGTCGTGTGCTAGATCGTCGGACTGTAGAACTCTGAAC | 9640 |
| FBC_Oligo56 | CAGGTCGCAGTTGAGATCGTCGGACTGTAGAACTCTGAAC | 9641 |
| FBC_Oligo57 | CAGGTCTTAACGGGGATCGTCGGACTGTAGAACTCTGAAC | 9642 |
| FBC_Oligo58 | CAGGTCGCTCGATTGATCGTCGGACTGTAGAACTCTGAAC | 9643 |
| FBC_Oligo59 | CAGGTCACACCTGTGATCGTCGGACTGTAGAACTCTGAAC | 9644 |
| FBC_Oligo60 | CAGGTCAGACGGTTGATCGTCGGACTGTAGAACTCTGAAC | 9645 |
| FBC_Oligo61 | CAGGTCGCAAACCAGATCGTCGGACTGTAGAACTCTGAAC | 9646 |
| FBC_Oligo62 | CAGGTCGAGTATGGATCGTCGGACTGTAGAACTCTGAAC | 9647 |
| FBC_Oligo63 | CAGGTCGGTCTTTCGATCGTCGGACTGTAGAACTCTGAAC | 9648 |
| FBC_Oligo64 | CAGGTCCATCTGCTGATCGTCGGACTGTAGAACTCTGAAC | 9649 |
| FBC_Oligo65 | CAGGTCTTCGCAAGGATCGTCGGACTGTAGAACTCTGAAC | 9650 |
| FBC_Oligo66 | CAGGTCTTGTGACGGATCGTCGGACTGTAGAACTCTGAAC | 9651 |
| FBC_Oligo67 | CAGGTCTGCATGACGATCGTCGGACTGTAGAACTCTGAAC | 9652 |
| FBC_Oligo68 | CAGGTCCAACGTGAGATCGTCGGACTGTAGAACTCTGAAC | 9653 |
| FBC_Oligo69 | CAGGTCTAGGCTTCGATCGTCGGACTGTAGAACTCTGAAC | 9654 |
| FBC_Oligo70 | CAGGTCTGGTAGGAGATCGTCGGACTGTAGAACTCTGAAC | 9655 |
| FBC_Oligo71 | CAGGTCTGCAGCTTGATCGTCGGACTGTAGAACTCTGAAC | 9656 |
| FBC_Oligo72 | CAGGTCCTGTACCTGATCGTCGGACTGTAGAACTCTGAAC | 9657 |
| FBC_Oligo73 | CAGGTCCGCAATGAGATCGTCGGACTGTAGAACTCTGAAC | 9658 |
| FBC_Oligo74 | CAGGTCGATCCAAGGATCGTCGGACTGTAGAACTCTGAAC | 9659 |
| FBC_Oligo75 | CAGGTCCACTTACGGATCGTCGGACTGTAGAACTCTGAAC | 9660 |
| FBC_Oligo76 | CAGGTCAACTAGGCGATCGTCGGACTGTAGAACTCTGAAC | 9661 |
| FBC_Oligo77 | CAGGTCACTAGCGTGATCGTCGGACTGTAGAACTCTGAAC | 9662 |
| FBC_Oligo78 | CAGGTCCGTTCGTTGATCGTCGGACTGTAGAACTCTGAAC | 9663 |
| FBC_Oligo79 | CAGGTCAGTCACGAGATCGTCGGACTGTAGAACTCTGAAC | 9664 |
| FBC_Oligo80 | CAGGTCCCTGTAACGATCGTCGGACTGTAGAACTCTGAAC | 9665 |

TABLE 5-continued

| Oligonucleotide Name | Oligonucleotide Sequence | SEQ ID NO: |
|---|---|---|
| FBC_Oligo81 | CAGGTCGTCCTCTTGATCGTCGGACTGTAGAACTCTGAAC | 9666 |
| FBC_Oligo82 | CAGGTCCAGCGAATGATCGTCGGACTGTAGAACTCTGAAC | 9667 |
| FBC_Oligo83 | CAGGTCATGGTTGGGATCGTCGGACTGTAGAACTCTGAAC | 9668 |
| FBC_Oligo84 | CAGGTCGAGGTTCTGATCGTCGGACTGTAGAACTCTGAAC | 9669 |
| FBC_Oligo85 | CAGGTCTACCTCGAGATCGTCGGACTGTAGAACTCTGAAC | 9670 |
| FBC_Oligo86 | CAGGTCTTCTGTGCGATCGTCGGACTGTAGAACTCTGAAC | 9671 |
| FBC_Oligo87 | CAGGTCGACAACTGGATCGTCGGACTGTAGAACTCTGAAC | 9672 |
| FBC_Oligo88 | CAGGTCCGACAACAGATCGTCGGACTGTAGAACTCTGAAC | 9673 |
| FBC_Oligo89 | CAGGTCTCGATACCGATCGTCGGACTGTAGAACTCTGAAC | 9674 |
| FBC_Oligo90 | CAGGTCCCATACTCGATCGTCGGACTGTAGAACTCTGAAC | 9675 |
| FBC_Oligo91 | CAGGTCATTCGCAGGATCGTCGGACTGTAGAACTCTGAAC | 9676 |
| FBC_Oligo92 | CAGGTCACCATAGGGATCGTCGGACTGTAGAACTCTGAAC | 9677 |
| FBC_Oligo93 | CAGGTCCGATCAAGGATCGTCGGACTGTAGAACTCTGAAC | 9678 |
| FBC_Oligo94 | CAGGTCACCTTGCTGATCGTCGGACTGTAGAACTCTGAAC | 9679 |
| FBC_Oligo95 | CAGGTCGACTCAGTGATCGTCGGACTGTAGAACTCTGAAC | 9680 |
| FBC_Oligo96 | CAGGTCGTCAATCCGATCGTCGGACTGTAGAACTCTGAAC | 9681 |

Table 6 provides for oligonucleotide sequences used to generate the second set of barcoded beads (SBC) for combinatorial synthesis in Experiment 2.

TABLE 6

| Oligonucleotide Name | Oligonucleotide Sequence | SEQ ID NO: |
|---|---|---|
| SBC_Oligo1 | AAAAAAAAAAAAAAAAAAAAAAAAGGTGATACAGGTCAAAAAAAAAGATCGTCGGACTGTAGAACTC | 9682 |
| SBC_Oligo2 | AAAAAAAAAAAAAAAAAAAAAAAATGAATGCCAGGTCAAAAAAAAAGATCGTCGGACTGTAGAACTC | 9683 |
| SBC_Oligo3 | AAAAAAAAAAAAAAAAAAAAAAAATGCCAAACAGGTCAAAAAAAAAGATCGTCGGACTGTAGAACTC | 9684 |
| SBC_Oligo4 | AAAAAAAAAAAAAAAAAAAAAAAACAGAAGCAGGTCAAAAAAAAAGATCGTCGGACTGTAGAACTC | 9685 |
| SBC_Oligo5 | AAAAAAAAAAAAAAAAAAAAAAAACACTGGACAGGTCAAAAAAAAAGATCGTCGGACTGTAGAACTC | 9686 |
| SBC_Oligo6 | AAAAAAAAAAAAAAAAAAAAAAAACGATGATCAGGTCAAAAAAAAAGATCGTCGGACTGTAGAACTC | 9687 |
| SBC_Oligo7 | AAAAAAAAAAAAAAAAAAAAAAAAGTGTCCACAGGTCAAAAAAAAAGATCGTCGGACTGTAGAACTC | 9688 |
| SBC_Oligo8 | AAAAAAAAAAAAAAAAAAAAAAAATCCTCTTCAGGTCAAAAAAAAAGATCGTCGGACTGTAGAACTC | 9689 |
| SBC_Oligo9 | AAAAAAAAAAAAAAAAAAAAAAAAGTGCAGTCAGGTCAAAAAAAAAGATCGTCGGACTGTAGAACTC | 9690 |
| SBC_Oligo10 | AAAAAAAAAAAAAAAAAAAAAAAAGGTAGACAGGTCAAAAAAAAAGATCGTCGGACTGTAGAACTC | 9691 |

Analysis of Single Cell RNA-Seq Data

Read 1 of the single cell RNA-Seq data contains a cell-identifying barcode sequence followed by poly(dT), and read 2 contains a 8-base UMI followed by a 6-base lane-identifying barcode and a transcript sequence. The reads are first demultiplex based on the lane-identifying barcode while recording the corresponding UMI using a custom Python script. We then map the remainder of read 2 to the human genome and transcriptome (hg19, Ensembl annotation from Illumina iGenomes) using the STAR aligner. Mapped reads for each lane are then demultiplexed based on the cell-identifying barcodes in read 1 and assigned to a gene using HTSeq. Both the lane- and cell-identifying barcodes were allowed to have a single-base mismatch during demultiplexing.

The set of reads that uniquely mapped to the transcriptome were collected and assigned an address comprised of its cell-identifying barcode, gene, UMI, and mapping position. In addition, the reads that mapped to both the genome and transcriptome were kept, but that mapped to only one position on the transcriptome and mapped to that position with the appropriate strand-specificity. The reads to identify unique molecules were filtered. Reads with identical addresses were collapsed to a single molecule. In addition, reads with identical cell-identifying barcodes, genes, mapping positions, and with UMIs having a Hamming distance less than or equal to two were collapsed to a single molecule. All reads considered identical molecules by the above definition (UMIs with a Hamming distance less than or equal to two and mapping position within six bases) were removed but that also occurred with different cell-identifying barcodes within the same lane. This approach likely underestimates of the true number of molecules associated with each cell and gene and results in some loss of gene detection. However, it also removes molecules that may become spuriously associated with the incorrect cell via PCR recombination, as observed and similarly filtered in previous studies that used very similar library construction protocols.

To identify barcodes that correspond to actual individual cells in our device in Experiment 1, the observed cell-identifying barcodes were filtered by progressively down-sampling the corresponding gene profiles to the same number of total reads and assessing the number of unique molecules detected from each cell-identifying barcode. After excluding cell-identifying barcodes having zero associated molecules, it was found that the distribution of associated unique molecules to be bimodal, with one small subpopulation having nearly as many unique molecules as reads at low read totals. It was found the size of this subpopulation to be in excellent agreement with our device imaging data. These 598 profiles were taken to represent the actual individual cells captured in the device with a barcoded bead. We used the same approach to assess the cell-identifying barcodes in Experiment 2.

The 396 single-cell profiles were kept with the highest coverage in the data set (all five lanes represented). The U87 and MCF10a single cell profiles were compared to bulk RNA-Seq profiles of U87 and MCF10a cells. Bulk RNA-Seq library from ~$10^7$ U87 cells were prepared using the TruSeq RNA-Seq library preparation kit (Illumina) and sequenced the library to a depth of ~30M, 100-base single-end reads on an Illumina HiSeq 2500. Publically available bulk RNA-Seq profile of MCF10a cells was obtained from the Gene Expression Omnibus (entry GSE45258). Reads were mapped to the transcriptome as described above and expression values (FPKM) were computed using Cufflinks. Pearson correlation coefficients between single cell and bulk profiles were computed between log-transformed single-cell expression profiles (unique molecules per million reads plus one) and log-transformed bulk values (FPKM plus one). Single cell median profiles were generated from different numbers of randomly selected single cell profiles and repeated this random sampling ten times without replacement for each data point in FIGS. 7A and 7B. For each Pearson correlation calculation, only genes with log-transformed single cell median or bulk values greater than 0.5 were included.

Differential expression analysis was conducted by comparing each detected gene in the two cell type-exclusive lanes using Wilcoxin's rank-sum test. Genes with $p<0.05$ were used for clustering analysis. Regardless of differential expression $+/-(1-p)$ was used (which is positive for expression biased in one cell type and negative for expression biased towards a second cell type) for each gene as input to iPAGE, a mutual information-based algorithm that can associate gene ontologies with genes based on an assigned numerical value [35]. A matrix of pairwise Spearman correlation coefficients was generated based on unique molecules detected across 396 single cell profiles in Experiment 1 (247 profiles in Experiment 2) using only the differentially expressed genes. The data was then clustered with the MATLAB implementation t-SNE using the correlation matrix as input. The single cell profiles were color coated in the t-SNE clusters using a simple classifier score given by the log-ratio of the number of cell type-specific genes for each of the two cell types in a given cell with an above-average rank in expression level (FIG. 8C).

Table 7 describes estimated costs per reagents and associated costs in an aspect of the disclosure.

TABLE 7

| Reagent | Volume | Stock Volume | Price of Stock | Price per Run |
|---|---|---|---|---|
| SUPERaseIN (Ambion) | 19 uL | 500 uL | $350.40 | $13.32 |
| dNTPs (NEB) | 10 uL | 800 uL | $44.80 | $0.56 |
| HiScribe IVT Kit (NEB) | 1 uL | 50 uL | $169.60 | $3.39 |
| MessageAamp II Kit (Ambion) | 3 uL | 740 uL | $3,668.00 | $14.87 |
| PrimeScript RT (Clontech) | 5 uL | 200 uL | $501.63 | $12.54 |
| Phusion polymerase (NEB) | 0.5 uL | 250 uL | $336.00 | $0.67 |
| Lane Barcode RT primers (IDT) | 15 uL | 3155 uL | $542.25 | $0.86 |
| NHS beads (GE) | 3.25 uL | 25000 uL | $155.80 | $0.02 |
| Streptavidin (NEB) | 5 uL | 1000 uL | $188.80 | $0.94 |
| Dual-biotin anchor oligo (IDT) | 0.64 uL | 700 uL | $225.75 | $0.21 |
| Klenow fragment exo-(NEB) | 1.5 uL | 200 uL | $188.80 | $1.42 |
| dNTPs (NEB) | 3.5 uL | 800 uL | $44.80 | $0.20 |
| FBC primers (IDT) | 0.96 uL (all 96) | 240,000 (all 96) | $484.56 total | $0.002 |
| SBC primers (IDT) | 0.66 uL (all 10) | 4000 uL (all 10) | $340.00 total | $0.67 |
| Experiment Costs | | | | $46.21 |
| Bead Costs | | | | $3.46 |
| Total Cost per Run | | | | $49.67 |
| Cost per Cell | | 250-500 cells | | $0.10-$0.20 |

Example 3

Bead Synthesis 1 million sequence-barcoded mRNA capture beads (MA-COSKO-2011-10, ChemGenes) were washed 6 times with DI water, re-suspended in 1280 uL of DI water, and evenly distributed to 64 wells on a 96-well plate. The plate is then sealed with adhesive cover, vortexed for 5 minutes, centrifuged at 300 g for 1 minute, sonicated in a water batch sonicator (FS-20, Fisher Scientific) for 5 minutes, incubated at 4° C. for 12 hours, and centrifuged again at 300 g for 1 minute.

Figure 19:
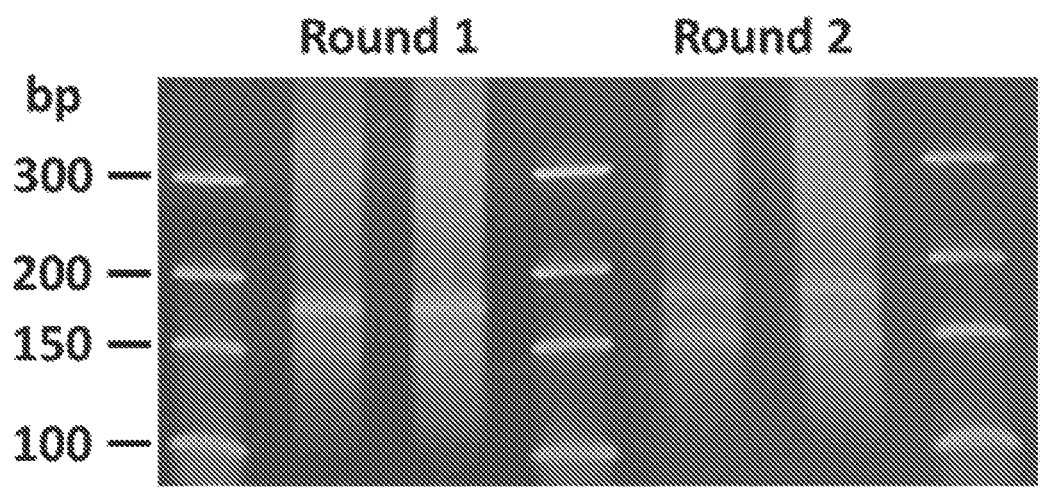
FIG. 19 shows gel electrophoresis analysis of the bead-free oligo PCR product from a first (left) and second (right) round of bead synthesis reactions.
Figure 20:
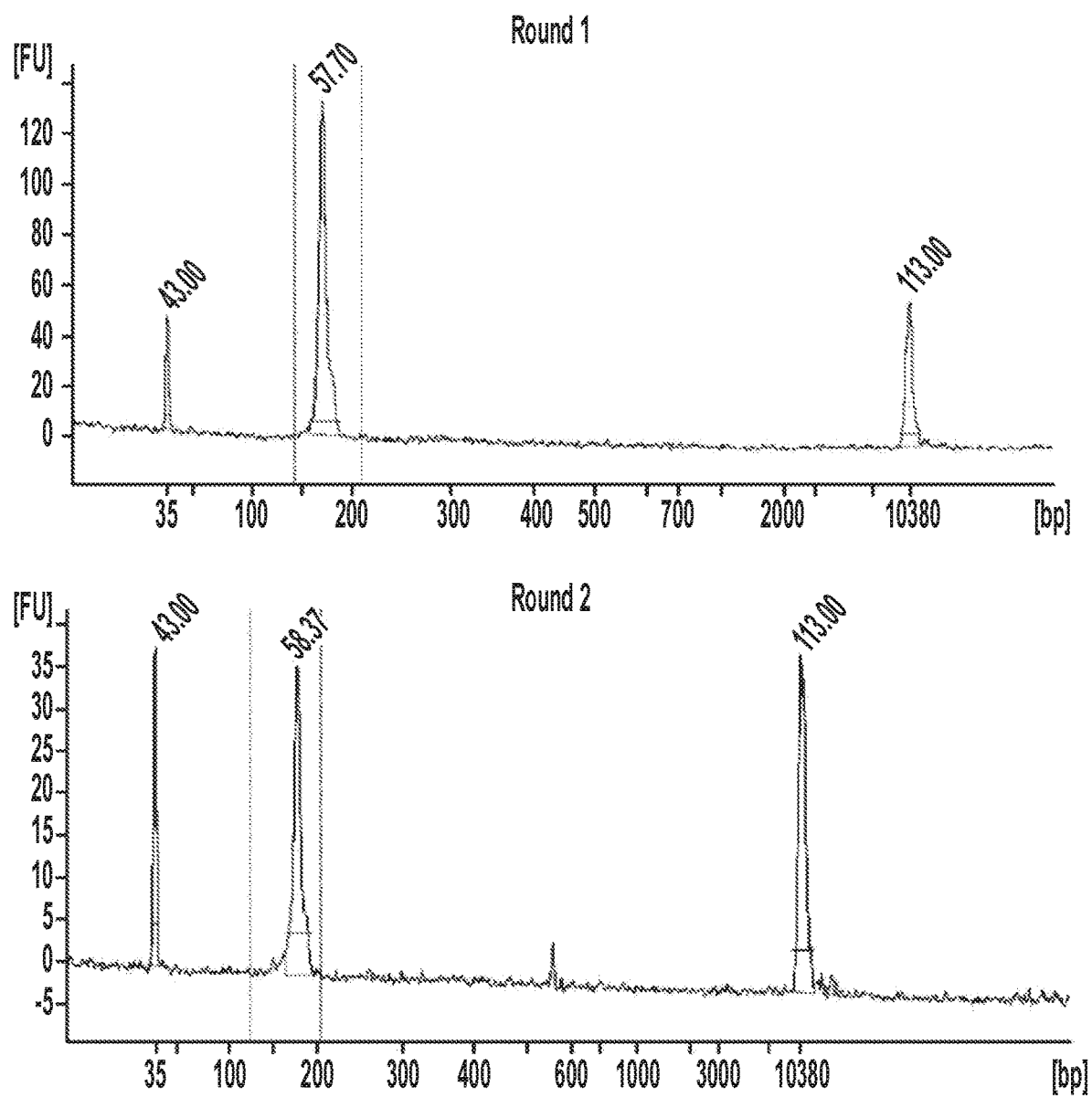
FIGS. 20A and 20B show capillary electrophoresis analysis of the gel-purified bead-free oligo PCR product from a first round (FIG. 20A) and a second round (FIG. 20B) of bead synthesis reactions.

Library Preparation and Sequencing of the Bead-Free DNA 5 uL supernatant from each well was collected and mixed with 10 uL of 1 uM NexterapolyA primer and 2 uL 10×NEBuffer 2 (B7002S, NEB) in separate wells on a 96-well plate. The mixtures were incubated at 95° C. for 2 minutes, then cooled down to 25° C. on a thermocycler. 2 uL of 10 mM dNTPs (N04475, NEB) and 1 uL of DNA polymerase (M0212S, NEB) were then added to each reaction mixture, incubated at 25° C. for 15 minutes and at 37° C. for 1 hour followed by heat inactivation of the DNA polymerase at 75° C. for 20 minutes, then cooled down to 4° C. 4 uL sample from each reaction was mixed with 2 uL of 2 uM well-specific barcoded custom P7 primer, 2 uL of 2 uM custom P5 primer (AATGATACGGCGAC-CACCGAGATCTACACGCCTGTCCGCG-GAAGCAGTGGTATC AACGCAGAGT*A*C, (SEQ ID NO: 9692) IDT), and 8 uL of 2× Kapa HiFi Hotstart Readymix (KK2601, Kapabiosystems). The mixture was then subjected to a PCR amplification protocol (95 C 3 minutes, 14 cycles of (95 C 10 s, 55 C 30 s, 72 C 30 s), 72 C 5 minutes, hold at 4 C). 5 uL of the PCR product from each reaction were pooled together and purified using the solid-phase reversible immobilization (SPRI) paramagnetic bead technology (A63880, Beckman Coulter) with a 2:1 bead-to-sample volume ratio and eluted in 50 uL of nuclease free water. The PCR product was further purified by gel electrophoresis (456-5034, Biorad). A 180 bp gel band (FIG. 19) was observed and extracted. The extracted product was further analyzed by capillary gel electrophoresis (5067-4626, Agilent Technologies) to further examine the length distribution of the purified product (FIGS. 20A and 20B).

Ligation of Optical Oligoes to the mRNA Capture Beads

The remaining beads in each well were washed with DI water and resuspended in a 50 uL reaction mixture that contained 5 uL of 10× T4 RNA ligase reaction buffer (M0204S, NEB), 25 uL of 50% PEG 8000 (M0204S, NEB), 5 uL of 10 Mm ATP (M0204S, NEB), 1 uL of 5% Tween-20, 2.5 uL of T4 RNA ligase 1 (M0204S, NEB), a well-specific unique combination of a set of 6 optical barcode oligo species (2 uL at 100 uM each), and water. The reactions were incubated at room temperature for 24 hours on a rotisserie. 5 uL of 10% SDS and 1 uL of 500 Mm EDTA were then added to each well, and incubated for 5 minutes at room temperature. All beads were then pooled together into a single microcentrifuge tube, washed twice with TE/TW buffer (10 mM Tris-HCl, 1 mM EDTA, 0.01% Tween-20, pH 8.0) and re-suspended in 1280 uL of TE/TW buffer.

The beads were subjected to a second round of the synthesis workflow described above using a separate set of 64 well-specific barcoded custom P7 primers in the PCR amplification of bead-free oligoes and a separate set of 6 optical barcode oligoes for the ligation reactions.

The 128 bead-free DNA libraries resulted from the above two rounds of synthesis reactions were sequenced on a NextSeq 500 machine (Illumina) with a custom read 1 sequencing primer (GCCTGTCCGCG-GAAGCAGTGGTATCAACGCAGAGTAC (SEQ ID NO: 9693), IDT). 21 bases were sequenced on read 1. The resulting raw fastq files were processed to obtain the list of sequence-barcoded mRNA capture beads that were present in each of the 128 ligation reactions to which a unique known combination of optical barcode oligoes were added. Thus, a two-column look-up table was obtained where each row represents a bead, one column contains a 12-base sequencing barcode sequence, and the other column contains a 12-digit binary optical barcode sequence.

Example 4: Mixed Species Experiment

Figure 21:
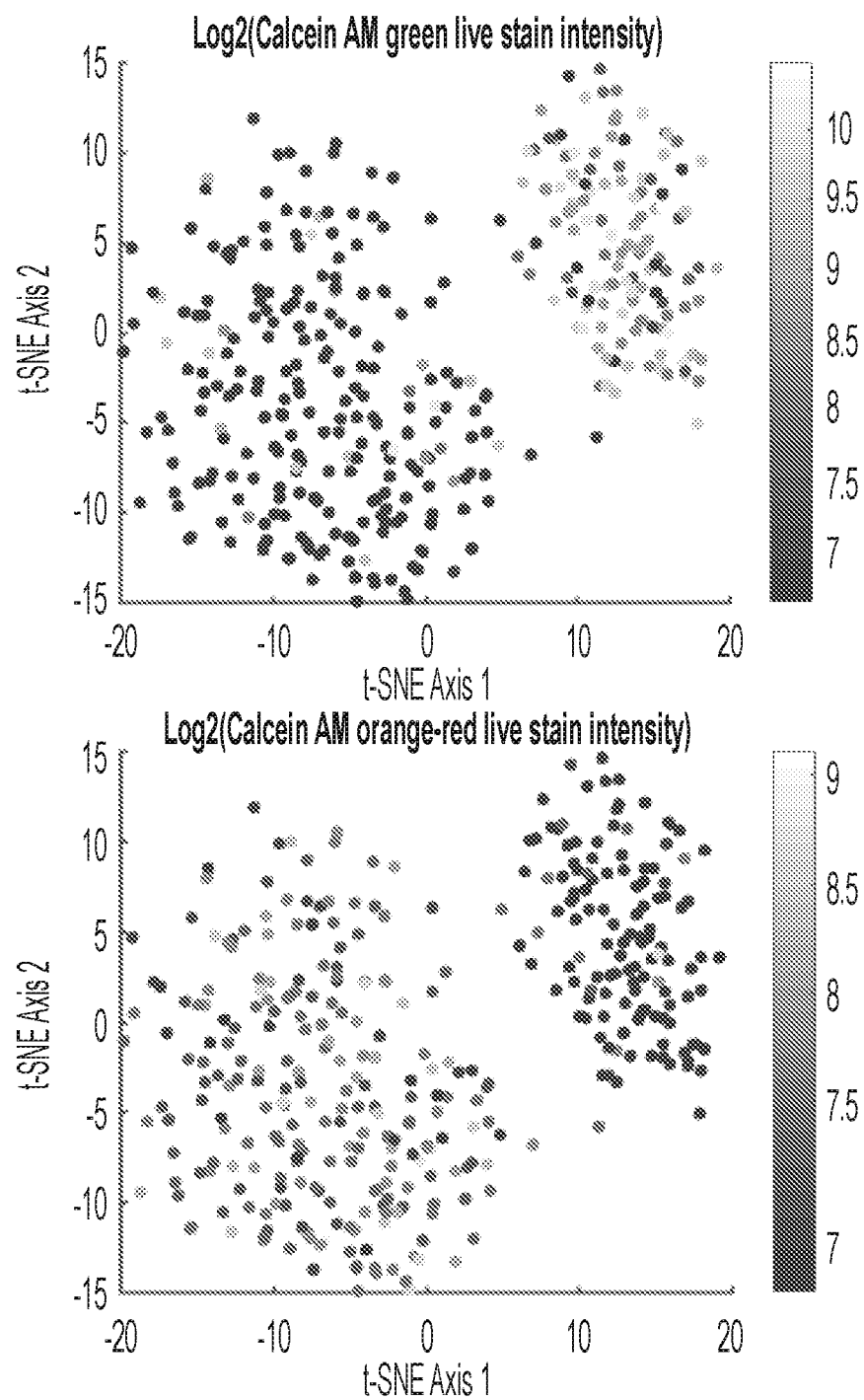
FIGS. 21A and 21B present integrated sequencing and imaging data for a mixed species experiment.

FIGS. 21A and 21B present integrated sequencing and imaging data for a mixed species experiment. Mixed human-mouse single-cell RNA-Seq data was projected using tSNE, revealing two clusters of cells that correspond to U87 (human) and 3T3 (mouse). The points in the tSNE plot were shaded according to the fluorescence intensity of the two live stain dyes, one of which was used to stain U87 (human) and 3T3 (mouse). The vast majority of cells with high fluorescence intensity in the channel used to image human cells are in the human cluster and vice versa, demonstrating the efficacy of the approach even without any error-correcting barcodes.

Device Preparation

On the day before the experiment, a microwell array flow cell device that has 15,000 microwells was filled with wash buffer (20 Mm Tris-HCl, 50 Mm NaCl, 0.1% Tween-20, pH 7.9) and stored in a humid chamber (a pipette tip box half-filled with water) at room temperature. On the day of the experiment, the device was washed by TBS buffer.

Cell Preparation

Human U87 cells and mouse 3T3 cells were live stained respectively with 4 uM green (C3100MP, ThermoFisher Scientific) and orange-red (C34851, ThermoFisher Scientific) live stain dyes in cell culture media (10% FBS in DMEM) in a 37° C. incubator for 15 minutes. The cells were then dissociated into single cell suspension in separate colonial tubes using 0.25% Trypsin-EDTA (25200-072, Life Technologies), re-suspended in TBS, and counted.

Cell Loading and Imaging

The two cell lines were then mixed at 1:1 ratio and diluted into 1000 total cells/uL concentration. 20 uL diluted mixed species cell suspension was then pipetted into the microwell array flow cell device and incubated for 3 minutes. Any uncaptured cells were flushed out by a TBS buffer wash. The cell-loaded device was then scanned in three channels including bright field, green, and orange channels.

Reagent Preparation for scRNA-Seq Library Prep

While the device was being scanned, fresh lysis buffer (1% 2-Mercaptoethanol, 99% Buffer TCL (1031576, Qiagen)), RNase inhibitor doped wash buffer (0.02 U/uL SUPERaseIN (AM2696, Thermo Fisher Scientific) in wash buffer), reverse transcription (RT) reaction mix (1× Maxima RT buffer, 1 Mm dNTPs, 1 U/uL SUPERaseIN, 2.5 uM template switch oligo (AAGCAGTGGTAT-CAACGCAGAGTGAATrGrGrG (SEQ ID NO: 9694), IDT), 10 U/uL Maxima H Minus reverse transcriptase (EP0752, Thermo Fisher Scientific), 0.1% Tween-20), and perfluorinated oil (F3556-25ML, Sigma-Aldrich) were prepared and loaded into their designated reservoirs on an automated reagent delivery/temperature control system as described before (Yuan & Sims, Scientific Reports 6, 33883 (2016)). The perfluorinated oil, lysis buffer, wash buffer reagent channels were primed by sequentially turning on the channels for 10 seconds, 10 seconds, and 30 seconds, respectively.

Bead Loading

After the device scan was completed, about 20000 of dual-barcoded mRNA capture beads were re-suspended in 30 uL of TBS buffer and then loaded into the device. Gentle flow (<3 uL/s) were used for the bead loading and all subsequent fluid exchange in the device to minimize cell and bead loss. Bead suspension was circulated through the device 5 to 10 times to achieve a high bead loading rate (defined as the fraction of wells having a bead) and a high bead capture efficiency (defined as the fraction of beads captured in the wells). Uncaptured beads were then washed out by a TBS buffer wash.

Automated Cell Lysis, mRNA Capture, cDNA Synthesis and Barcoding

The cell/bead loaded device was then connected to the system for the automated cell lysis, mRNA capture, and cDNA synthesis and barcoding. The device was temporarily disconnected from the fluidic system, scanned on a fluorescence microscope, and then reconnected to the fluidic system. Fluorescent signal from the stained cell lysate is used to check sealing integrity and the completeness of cell lysis.

Removal of Unused Capture Primers by Exo-I Digestion

When reverse transcription reaction was completed, the device was washed with wash buffer, refilled with Exo-I reaction mixture (1×Exo-I buffer, 1 U/uL Exo-I (M0293L, NEB)), and incubated at 37° C. for 45 minutes, cooled down to room temperature, and washed with TE/TW buffer.

Sequential Fluorescence Hybridization

The device was then connected to an automated reagent delivery/scanning system for 12 rounds of sequential fluorescence hybridization in order to measure the presence of each of the 12 optical barcode oligoes on each bead in the device. Cy5-labeled oligoes whose sequences are complementary to the ligated optical barcode oligoes were used as the read-out probes. During each round of fluorescence hybridization, the device was first scanned in both bright field and the Cy5 probe channel. 200 nM probe diluted in wash buffer was then flowed into the device, followed by a 10-minute incubation step. Unbound probe molecules were then washed out using wash buffer. The device was scanned again in both bright field and Cy5 probe channel. 150 mM NaOH in water was then flowed into the device, followed by a 10-minute incubation step. Detached probe molecules were then washed out using wash buffer, which concludes one round of fluorescence hybridization.

Bead Extraction

Once all 12 rounds of fluoresce hybridization were complete, the device was cut evenly into multiple pieces using a razor blade such that each piece contained about 400 cell/bead pairs. The pieces were processed in parallel in separate reaction tubes. Beads in each piece were extracted by a 30-second gentle water bath sonication in ethanol followed by a 1-minute centrifugation at 200 g. The extracted beads were then washed with 1 mL 150 mM NaOH, 1 mL TE/TW buffer, and 1 mL water.

Pre-Amplification of Full-Length cDNA

The small pieces of device were then assembled together and scanned to identify the borderlines between the small pieces. Beads from each piece were split into four 50 uL PCR reactions that contains 25 uL of 2× Kapa HiFi Hotstart Readymix (KK2601, Kapabiosystems), 0.5 uL 100 uM SMRTpcr primer (AAGCAGTGGTATCAACGCAGAGT (SEQ ID NO: 9696), IDT), and 24.5 uL of water. The mixtures were subjected to a PCR amplification protocol on a thermocycler (95° C. 3 minutes, 4 cycles of (98° C. 20 seconds, 65° C. 45 seconds, 72° C. 3 minutes), 8 cycles of (98° C. 20 seconds, 67° C. 20 seconds, 72° C. 3 minutes), 72° C. 5 minutes, hold at 4° C.). SMRT PCR product (supernatant only) of beads from each small piece were pooled together and purified using the SPRI paramagnetic bead technology (A63880, Beckman Coulter) with a 0.6:1 bead-to-sample volume ratio and eluted in 10 uL of nuclease free water. The purified products were then quantified by a fluorimeter.

Amplification and Sequencing of Tagmented cDNA

Purified product from each of the small piece was tagmented, barcoded, and amplified using a commercially available kit (Nextera XT, FC-131-1024, Illumina) per the vendor's instructions with the following modifications. First, 0.6 ng was used as input for each reaction. Second, a custom P5 primer (AATGATACGGCGAC-CACCGAGATCTACACGCCTGTCCGCG-GAAGCAGTGGTATC AACGCAGAGT*A*C (SEQ ID NO: 9692), IDT) was used in the PCR amplification. The Nextera PCR products were then pooled and purified twice using the SPRI paramagnetic bead technology (A63880, Beckman Coulter) with a 0.6:1 and 1:1 bead-to-sample volume ratios in the first and second round of purification respectively. The purified Nextera PCR product was sequenced on a NextSeq 500 machine (Illumina) with a custom read 1 sequencing primer (GCCTGTCCGCG-GAAGCAGTGGTATCAACGCAGAGTAC (SEQ ID NO: 9695), IDT). 21 bases were sequenced on read 1 and 63 bases were sequenced on read 2. The raw fastq files generated by sequencers were processed to obtain a digital expression matrix where each column represents the expression profile of a cell and each row represents the expression level of a gene for cells from each of the small pieces. The look-up table generated in the bead synthesis step was then used to link each cell's imaging phenotype to sequencing barcode sequence of the bead that resided in the same well with the cell and the associated mRNA expression profile.

Example 5

Merged Barcode for Sequence/Microscope

In the dual barcode embodiment described in previous examples, the mRNA capture beads contain two barcodes. The first barcode (sequencing barcode) becomes associated with the cDNA library obtained from each individual cell and distinguishes the cDNA from each cell on the sequencer. The second barcode (optical barcode) is used to identify the same cell by imaging with a microscope. Having two separate barcodes requires two manufacturing steps to synthesize the beads. Having two separate barcodes also requires a separate sequencing experiment to determine which optical barcode is attached to each sequencing barcode, as these are associated randomly in the synthesis process. To avoid these complications, an embodiment is provided wherein the sequencing barcode and the optical barcode are merged into the same entity.

In the dual barcode embodiment described in previous examples, the optical barcode is attached to a subset of the mRNA capture sites (poly-dT sequences) on each bead. This reduces the number of sites available for mRNA capture and therefore efficiency. This problem is avoided by making the sequencing barcode and optical barcode the same entity, because the resulting merged barcode can be located upstream of the mRNA capture site and does not have to be attached to its 3'-end, which ablates its ability to prime cDNA synthesis.

In the dual barcode embodiment described in previous examples, because only a subset of mRNA capture sites on each bead can be occupied by an optical barcode, the fluorescence signal obtainable from the optical barcode is relatively low. The fluorescence signal is improved by making the sequencing barcode and optical barcode the same entity, since the resulting merged barcode can be located upstream of the mRNA capture site and 100% of oligonucleotides on the bead can contain an optical barcode.

The merged barcode permits a simpler manufacturing process for optically barcoded mRNA capture beads, yields higher signal-to-noise allowing use of simpler microscopy equipment, and provides higher-quality scRNA-seq data.

The merged barcodes can be characterized by three parameters: N, M, and L. Each merged barcode contains N oligonucleotide sequence blocks. There is a unique set of M oligonucleotide sequences, each of length L nucleotides for each of the N blocks. For each sequence block on each bead, an oligonucleotide sequence is selected from the corresponding set of M oligonucleotide sequences. For example, for a given bead, the oligonucleotide sequence of block 1 would be chosen from the first set of M oligonucleotide sequences and the oligonucleotide sequence of block 2 would be chosen from the second set of M oligonucleotide sequences, etc. In this way, one can combinatorially generate a set of M^N unique merged barcodes from M×N oligonucleotide sequences. For example, if M=100 and N=2, one could generate 100^2=10,000 unique merged barcodes from 2 sets of 100 oligonucleotide sequences (M×N=100×2=200 total oligonucleotide sequences). If sequential fluorescence hybridization is to be used as a read-out, then it is convenient for all M×N oligonucleotide sequences to be unique. However, if sequencing is to be used as a read-out, then one could have, for example, identical sets of M oligonucleotide sequences for each block because the positional information afforded by sequencing could be used to distinguish the N oligonucleotide sequence blocks.

One approach to manufacturing beads conjugated to merged barcodes as described above is to use split-pool ligation of oligonucleotides. Consider the case that N=2 and M=96. One would purchase a 96-well plate of unique, 5'-phosphorylated oligonucleotides for each of the two sequence blocks in the barcode. One would then take beads conjugated to a universal oligonucleotide sequence adapter and add them to each well of the first 96-well plate along with reagents for DNA ligation (e.g., DNA ligase, an appropriate buffer, ATP). This set of 96 reactions would produce a library of beads conjugated to 96 different oligonucleotide sequences. Next, one would mix all of the beads from all 96 wells together in a single vessel and then add an equal proportion of the resulting pool to each of the 96 wells in the second plate of unique, 5'-phosphorylated oligonucleotides along with reagents for DNA ligation. At the end of this second reaction, one would again mix all of the beads from all 96 wells together in a single vessel. The second set of 96 reactions would produce a library of beads conjugated to 96^2=9,216 unique merged barcodes.

A second approach to manufacturing beads conjugated to merged barcodes as described above is to use split-pool solid-phase oligonucleotide synthesis. Consider again the case that N=2 and M=96. One would take beads conjugated to a universal oligonucleotide sequence adapter and split them into 96 wells. One would then use solid-phase (e.g., phosphoramidite-based) oligonucleotide synthesis to synthesize a unique oligonucleotide sequence onto the end of the universal oligonucleotide sequence adapters on the beads in each well. This set of 96 reactions would produce a library of beads conjugated to 96 different oligonucleotide sequences. Next, one would mix all of the beads from all 96 wells together in a single vessel and then add an equal proportion of the resulting pool to each of the 96 wells in the second plate. In the second plate, one would again use solid-phase (e.g., phosphoramidite-based) oligonucleotide synthesis to synthesize a unique oligonucleotide sequence onto the end of the first barcode sequence block that had been added to each bead in the first plate. At the end of this second reaction, one would again mix all of the beads from all 96 wells together in a single vessel. The second set of 96 reactions would produce a library of beads conjugated to 96^2=9,216 unique merged barcodes.

Figure 22:
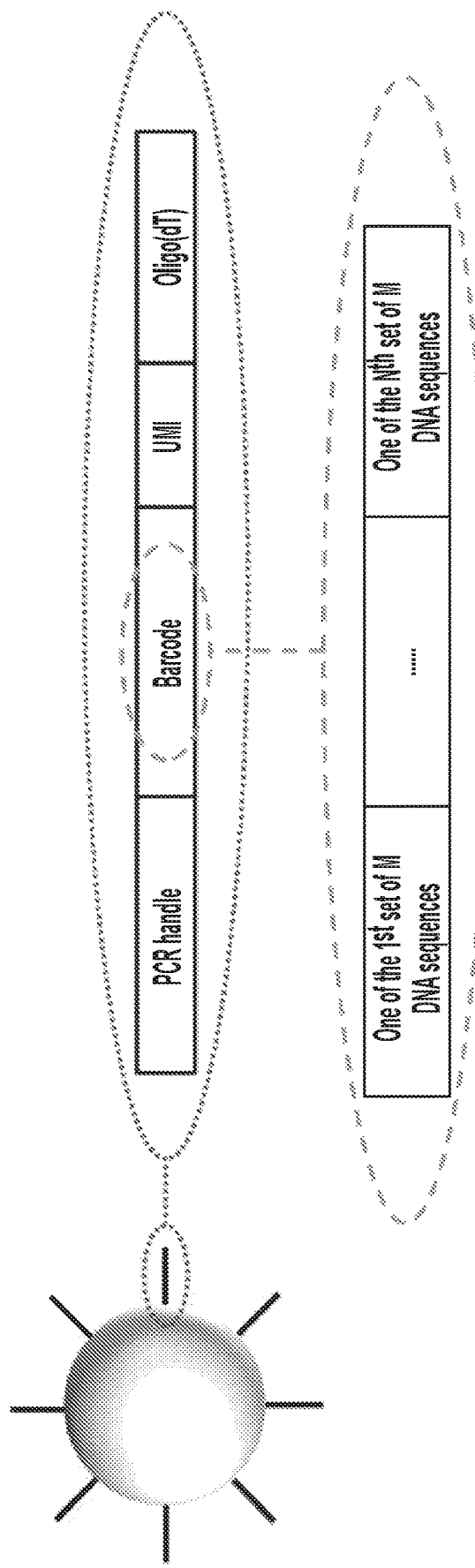
FIG. 22 illustrates bead design for a merged barcode oligonucleotide, with oligonucleotides attached to optically barcoded mRNA capture beads that enable simultaneous sequencing-based and optical demultiplexing of the same barcode sequence.

FIG. 22 shows the simplified design of the optically barcoded mRNA capture beads for the merged barcode. Unlike the previously-described dual barcode embodiments, there is only one cell-identifying barcode located upstream of the oligo(dT) mRNA capture site. This merged barcode contains a unique combination of multiple sequence blocks.

As illustrated in FIG. 22, we have N sets of M DNA sequences from which the N sequence blocks on each bead are generated, and one DNA sequence from each set is concatenated to form a unique barcode for each bead. For example, if there were three sets of 24 DNA sequences, one could generate 24^3=13,824 unique barcodes. These barcodes can be demultiplexed optically using sequential fluorescence hybridization just as in the previous implementation with a few practical modifications.

Figure 23:
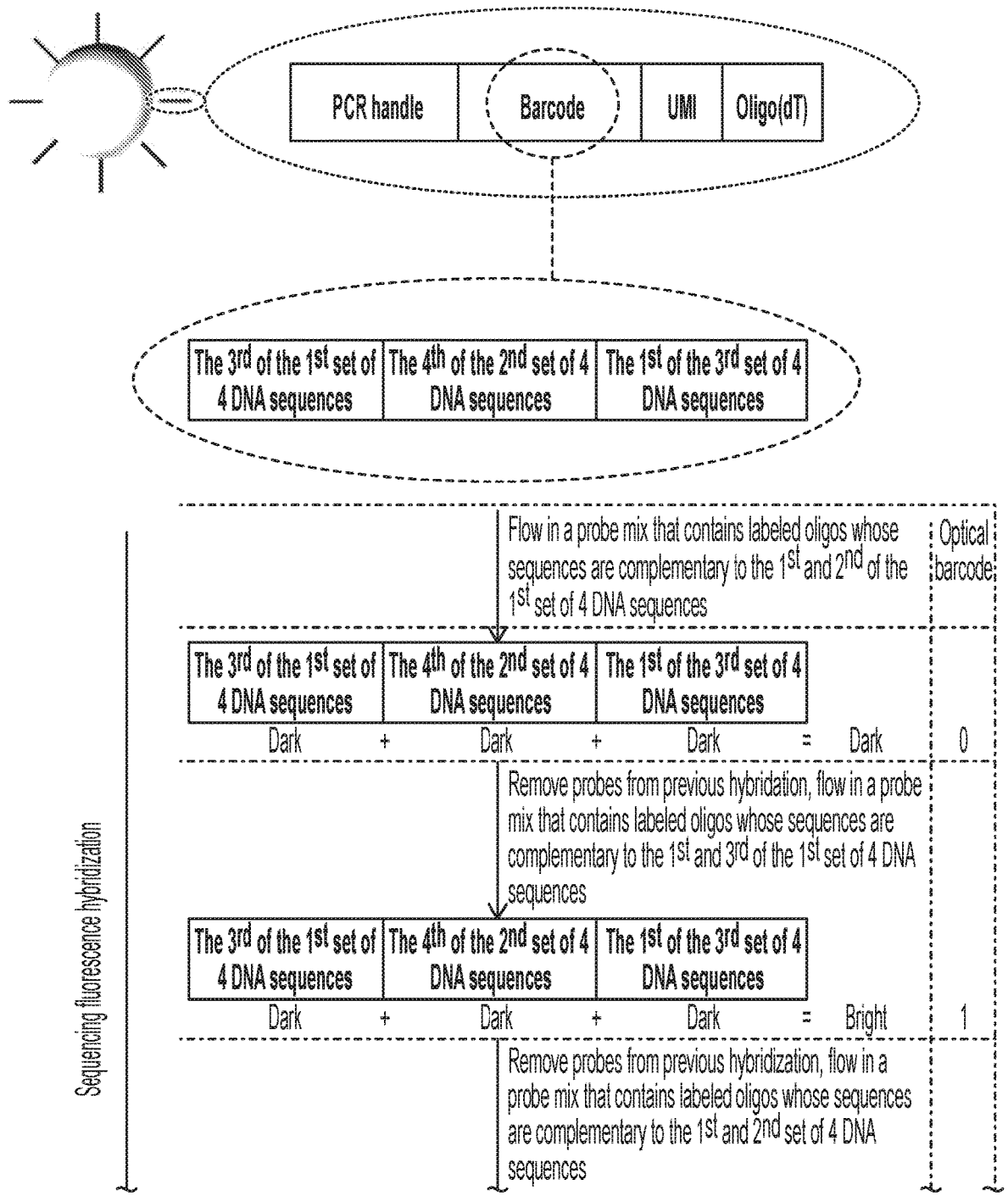
FIG. 23 is a schematic of optical demultiplexing by sequential fluorescence hybridization with combinatorial oligonucleotide pools (M=4, N=3) from merged barcode capture beads.
Figure 23:
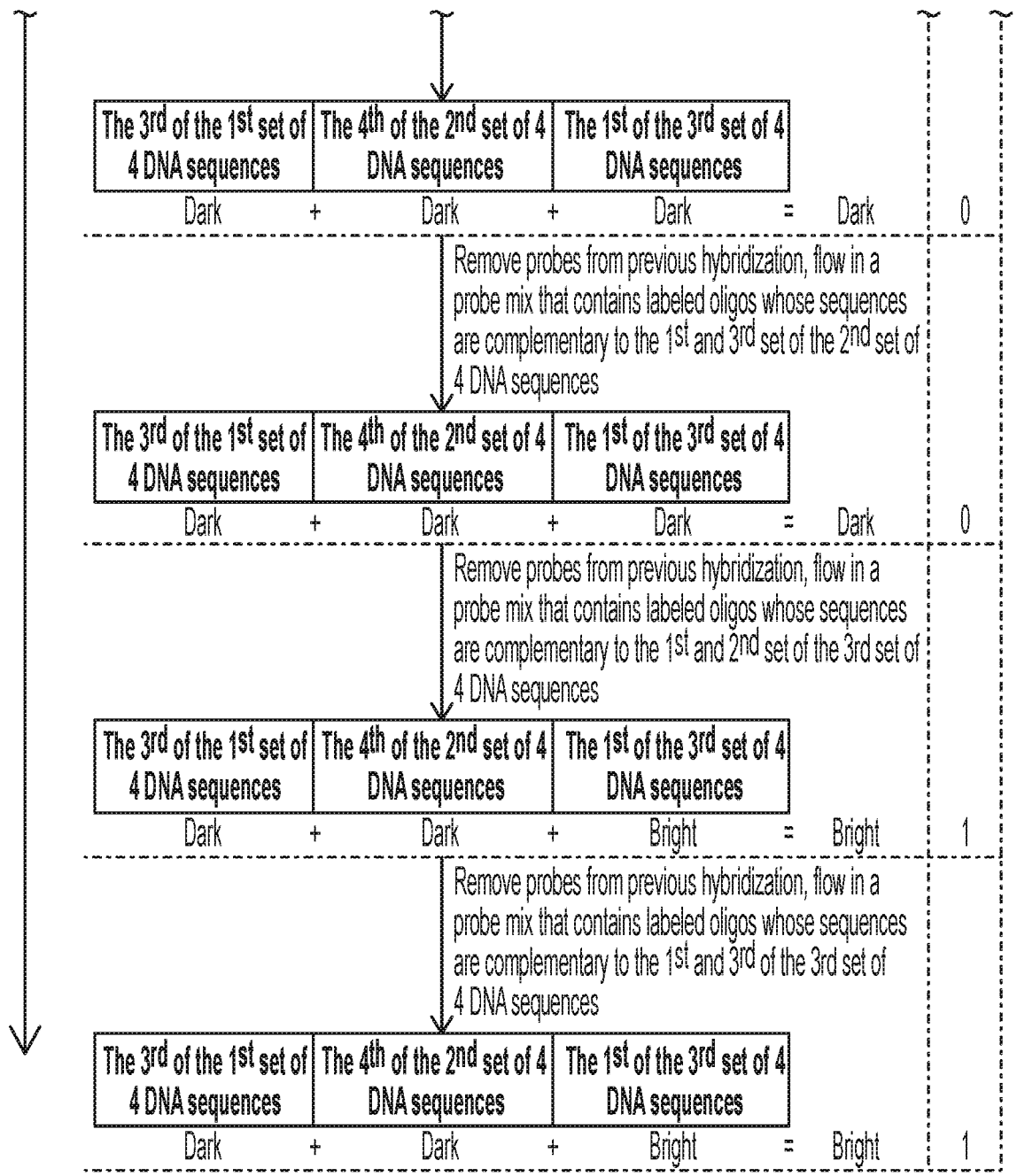

FIG. 23 illustrates an approach for optical demultiplexing of the beads illustrated in FIG. 22. In this scheme, the barcode is comprised of three concatenated sequence blocks (so N=3) and there are four sequences in each block (so M=4). For each of the three blocks, we introduce two mixtures of two probes to identify which of the four sequences are present in the block. For example, for the first block, first a mixture is introduced containing fluorescent probes that are complementary to sequences 1 and 2. Then a mixture is introduced containing fluorescent probes that are complementary to sequences 1 and 3. If sequence 3 is actually present on the bead, then the first mixture will give a negative result and the second will give a positive result. This outcome is unique to a bead harboring sequence 3 in its first block. This procedure is then repeat to identify the sequences in the remaining two blocks.

Optical demultiplexing of beads with the barcode format described in FIG. 22 and the readout method schematized in FIG. 23 is demonstrated. This approach avoids fluorescently labeling the large number of complementary probes directly. Instead, a universal sequence is included attached to each complementary probe that hybridizes to a universal fluorescently labeled oligonucleotide. This allows use of the same fluorescently labeled oligonucleotide to make all of the complementary probes fluorescent, which is highly cost effective. A representative image of fluorescence-based demultiplexing of a subset of the beads appears in FIG. 24.

Figure 24:
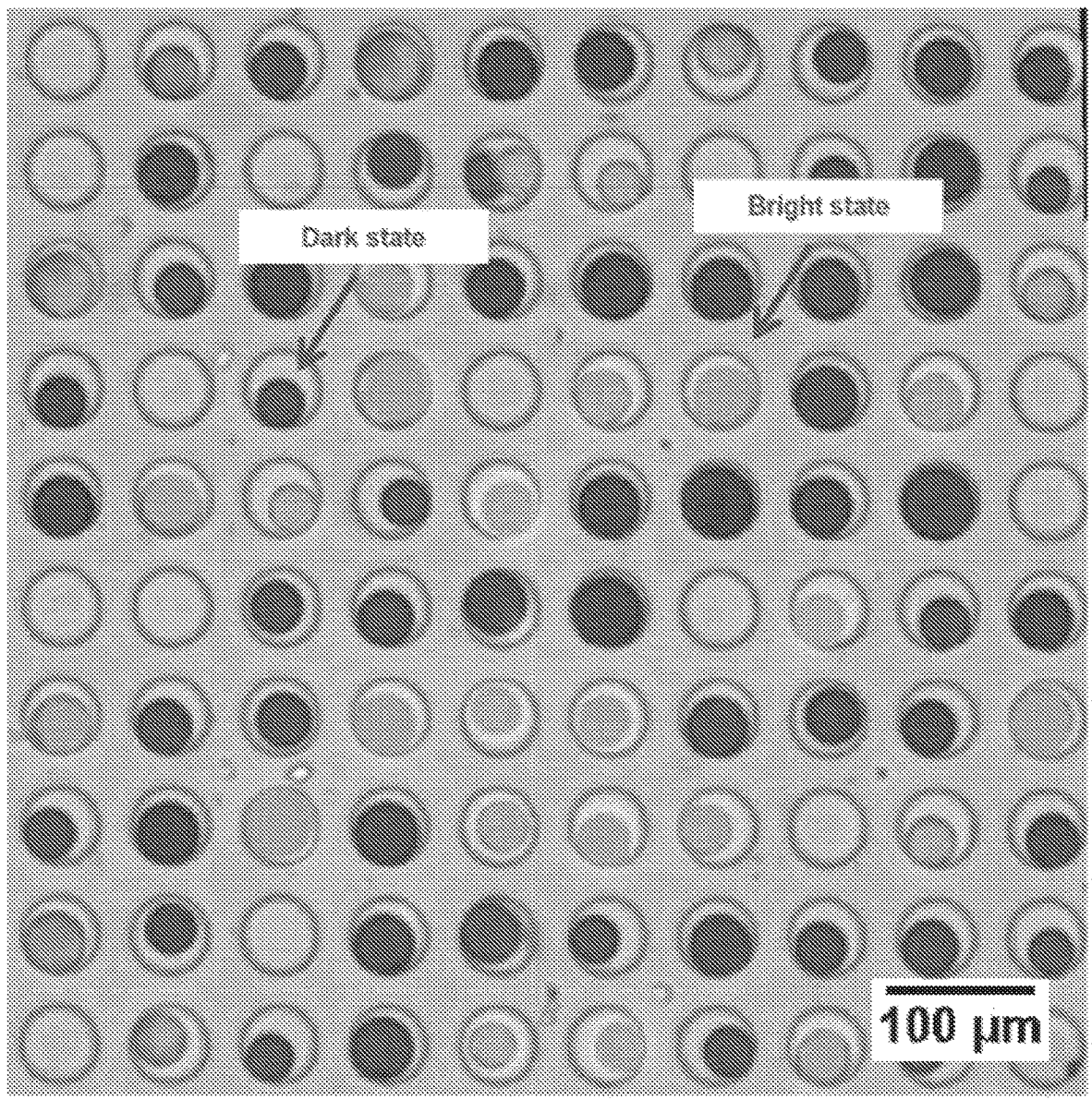
FIG. 24 is a fluorescence/bright field overlay image of microwell array filled with optically barcoded mRNA (merged barcode) capture beads during one cycle of optical demultiplexing, wherein as expected roughly half of the beads are highly fluorescent (bright state).

In the experiment that generated FIG. 24, barcoded beads with M=2 and N=3 were used. Initially followed is the microwell array-based single-cell RNA-Seq workflow described in Yuan and Sims, Scientific Reports 6, 33883, until the on-chip reverse transcription step. After the on-chip reverse transcription step, exonuclease I digestion reaction mix (1× Exo I buffer, 1 U/uL Exo I) is flowed in, and the device is incubated in a 37° C. incubator for 45 minutes. This step removes unused single-stranded capture primers that were accessible to enzymatic digestion. The device was then washed by TE/TW buffer (10 mM Tris pH8.0, 1 mM EDTA, 0.01% Tween-20). A hybridization mix (200 nM primary probe oligo, 20 mM Tris-HCl pH 7.9, 50 mM NaCl, 0.1% Tween-20) was subsequently flowed into the device and incubated for 10 minutes. The primary probe oligo is an unlabeled oligo whose sequence can be divided into two parts. One part of the oligo's sequence is complimentary to the first of the first set of two oligo sequences on the bead.

The other part's sequence is complimentary to a fluorescently labeled oligo which we call read-out probe. The device is then washed with wash buffer (20 mM Tris-HCl pH7.9, 50 mM NaCl, 0.1% Tween-20) to remove any unbound oligos. The read-out probe mix (200 nM read-out probe oligo, 20 mM Tris-HCl pH 7.9, 50 mM NaCl, 0.1% Tween-20) was then flowed into the device and incubated for 10 minutes. Unbound oligos were washed out by wash buffer afterwards. The device is then scanned under a microscope through both bright field and fluorescence channel which generated images like the ones shown in FIG. 24. Beads were then extracted from the device, washed with 150 mM NaOH, pooled together for subsequent tube-based library construction steps as described previously in Yuan and Sims (2016), Scientific Reports 6, 33883.

Merged Barcode mRNA Capture Beads (M=2, N=2)

To test the merged optical barcode scheme (SCOPE-seqV2), a small-scale pool of optically barcoded mRNA capture beads were designed with two concatenated sequence blocks (N=2) with two sequences in each block (M=2). The sequence in each block was eight bases long. This results in a total of four (2²=4) different bead species in the bead pool. The performance of these beads was characterized in 1) a single cell RNA-Seq experiment and 2) a fluorescence hybridization experiment.

Figure 25:
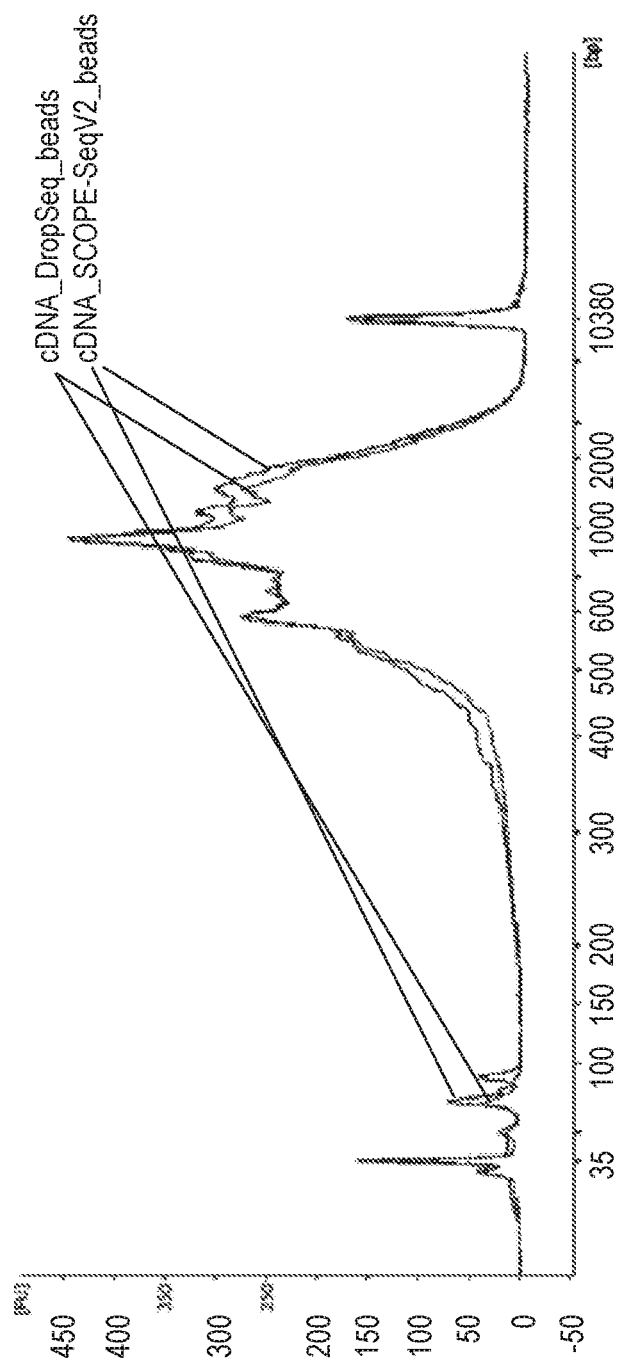
FIG. 25 is a length distribution of cDNA obtained using conventional RNA-seq beads and SCOPE-SeqV2 (merged barcode) beads measured on a high sensitivity bioanalyzer chip, showing almost identical results for the conventional RNA-seq and SCOPE-SeqV2 beads.

In the single cell RNA-Seq experiment, merged optically barcoded mRNA capture beads (referred as SCOPE-SeqV2 beads) and non-optically barcoded mRNA capture beads (referred as conventional RNA-seq beads) were used to perform single cell RNA-Seq in two separate microwell array devices on approximately (<20% difference) the same number of cells sampled from the same batch of cell culture using the protocol described in Yuan et al, Scientific Reports, 2016. Pre-amplified cDNA from both experiments were quantified by fluorometer (Qubit) and capillary gel electrophoresis (Bioanalyzer, Agilent). The amount of cDNA yield and cDNA length distribution were essentially identical for cDNA obtained using both types of beads (see FIG. 25). This observation suggests that capture efficiency for single-cell RNA-seq is uncompromised by this merged optical barcoding embodiment.

Figure 27:
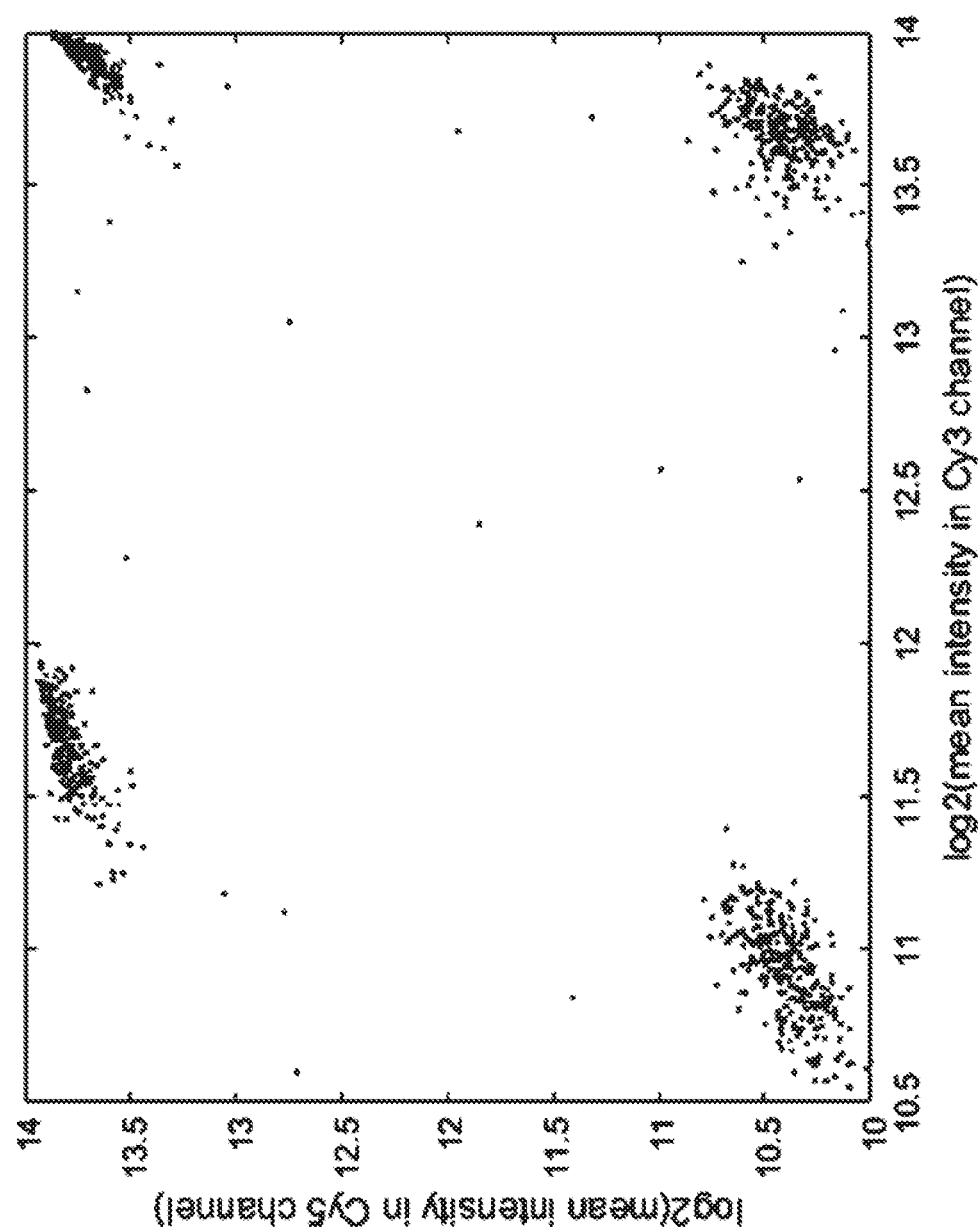
FIG. 27 is a scatter plot of the log 2 transformed mean intensities of individual beads in the Cy3 and Cy5 channels.

In the fluorescence hybridization experiment, exonuclease-treated SCOPE-SeqV2 beads were loaded into a microwell array device. A Cy3 dye-labeled 8-mer oligonucleotide whose sequence is complimentary to one of the two sequences in the first sequence block and Cy5 dye-labeled 8-mer oligonucleotide whose sequence is complimentary to one of the two sequences in the second sequence block were simultaneously hybridized to the beads in the microwell array device. Both oligonucleotides were introduced at a concentration of 100 nM in a hybridization buffer comprised of 2×SSC (Saline Sodium Citrate) with 10% DMSO (Dimethyl sulfoxide) and an incubation time of 10 minutes. Next, excess oligonucleotides were rinsed out of the device by laminar flow of buffer. Beads in microwell array device were then imaged in the Cy3 and Cy5 excitation/emission channels with an epifluorescence microscope, and a bright field transmission image was also acquired. A multi-color composite image of the beads (FIG. 26) clearly shows that there are four optically distinct bead species (pseudo-colored as black, green, orange, and red). A scatter plot of the log 2 transformed average bead intensity in the Cy3 and Cy5 channels (FIG. 27) demonstrates high signal-to-background ratio. Four bead populations can be readily detected.

Design Considerations for Merged Barcode Beads

In one embodiment, the length of the sequence in each merged optical barcode sequence block is long enough for stable oligonucleotide hybridization at room temperature but not too long to minimize DNA secondary structure. The formation of DNA secondary structure significantly compromises the quality of scRNA-Seq data and fluorescence hybridization-based optical demultiplexing. Typically, fluorescence probes with a length between 16 nt and 22 nt are used in fluorescence hybridization-based applications including single molecule fluorescence in situ hybridization. However, when 16 nt oligonucleotides were used in each optical barcode sequence block, scRNA-Seq data and optical demultiplexing were both significantly adversely affected. When 8 nt oligonucleotides were used in each optical barcode sequence block, uncompromised scRNA-Seq data (compared to conventional RNA-seq beads) and fluorescence hybridization signal with high signal-to-background ratio were obtained. Therefore, the length of optical barcode sequence in each block was set to be 8 nt.

To distinguish different optical barcode sequences using fluorescence hybridization, a preliminary list of 8-mer sequences was generated that are at least 3 Levenshtein distance away from each other. Any sequences that contain 3-base homopolymers or whose GC content is either <40% or >60%, or are perfectly self-complementary were filtered out. This constrains the oligonucleotide sequence space to 547 8-mer sequences (out of a possible 4^8=65,536).

A preliminary list of full-length mRNA capture oligonucleotide sequences was then generated by combinatorically arranging these 8-mer sequences in two optical barcode oligonucleotide sequence blocks separated by two random unique molecular identifier (UMI) bases. The composition of the full-length sequence is as follows:

TTTTTTTAAGCAGTGGTATCAACGCAGAGTACNN (8-mer Block 1)NN(8-mer Block 2)NNTTTTTTTTTTTTTTTTTTTTTTTTTTTTTT (SEQ ID NO: 9696)

The maximum length of continuous self-complimentary sequences within each full-length mRNA capture oligonucleotide sequence is calculated. The stability score of such self-complimentary structure is defined as $1.5*L_{GC}+L_{AT}$, wherein $L_{GC}$ and $L_{AT}$ are the number of GC bases and AT bases respectively in the continuous stretch of self-complimentary sequence. The individual 8-mer sequences were then ranked in ascending order by the sum of the stability score of all full-length sequences of which it was a member. The bottom 50% of the 8-mer sequences on this ranked list was filtered out leaving 274 8-mer sequences.

Another round of filtering is performed on this list based on the melting temperature and self-dimer or cross-dimer forming potential. Any 8-mer sequences with a predicted melting temperature below 25° C. or a strong tendency to form self-dimer or cross-dimer were excluded. 11 and 17 8-mer sequences were filtered out due to low melting temperature and strong potential to form self-dimer or cross-dimer respectively leaving 246 8-mer sequences (see attached sequence listing).

The 8-mer sequences also need to be highly distinct from the universal sequence adapters at the base of each bead (TTTTTTTAAGCAGTGGTATCAACGCAGAGTAC (SEQ ID NO: 9697)). The local alignment scores between all remaining 8-mer sequences and the universal sequence were calculated. The remaining 8-mer sequences were then ranked based on this local alignment score in ascending order. The top 96 8-mer sequences were used in the first optical barcode oligonucleotide sequence block. The 97$^{th}$ to 192$^{nd}$ 8-mer sequences were used in the second optical barcode oligonucleotide sequence block. A final list of 9216 full-length mRNA capture oligonucleotide sequences was then generated (see attached sequence listing).

SEQUENCE LISTING

The patent contains a lengthy sequence listing. A copy of the sequence listing is available in electronic form from the USPTO web site (https://seqdata.uspto.gov/?pageRequest=docDetail&DocID=US11788120B2). An electronic copy of the sequence listing will also be available from the USPTO upon request and payment of the fee set forth in 37 CFR 1.19(b)(3).

What is claimed is:

1. A method for demultiplexing capture bead barcodes using sequential fluorescence hybridization, wherein said method comprises:
   (a) introducing into a plurality of microwells at least one cell and one capture bead, wherein the microwells are formed from a first substrate that faces a second substrate, wherein the capture bead comprises a plurality of oligonucleotide sequences attached thereto, and wherein each oligonucleotide sequence comprises:
      i) a PCR handle identical in each oligonucleotide sequence on each capture bead,
      ii) a barcode configured for identification of the attached capture bead and an associated cell, wherein the barcode comprises N blocks, wherein each block is an oligonucleotide sequence of length 8 nt to 30 nt chosen from one of N unique sets of M oligonucleotide sequences, wherein N is at least 2 and M is at least 30, wherein said barcode is identifiable by sequential fluorescence hybridization;
      iii) a unique molecular identifier (UMI) of length 6 to 16 nucleotides (nt); and
      iv) an oligo(dT);
   (b) adding a lysis buffer to the microwells, capturing RNA from said at least one cell onto the capture bead, and reverse transcribing; and
   (c) optically demultiplexing the capture bead barcodes using sequential fluorescence hybridization, wherein the sequential fluorescence hybridization comprises sequentially introducing mixtures of fluorescently labeled oligonucleotide probes into the microwells, wherein:
      i) each of said probes is complementary to one of the oligonucleotide sequences in the unique sets of M oligonucleotide sequences,
      ii) said mixtures each comprise at least two probes which are complementary to oligonucleotides sequences within the same unique set of M oligonucleotide sequences, and
      iii) the fluorescent label for each of said at least two probes complementary to oligonucleotide sequences within the same unique set of M oligonucleotide sequences is a universal fluorescently labeled oligonucleotide hybridized to a universal sequence included in said probes,
   wherein a direct association is provided between phenotypic imaging information acquired from the single cells while located within the microwell and sequence data acquired from the captured and reverse transcribed cellular mRNA.

2. The method of claim 1, wherein said first and/or second substrates are polysiloxane substrates.

3. The method of claim 2, wherein the first and second substrates are polydimethylsiloxane (PDMS) substrates.

4. The method of claim 1, wherein N is 2 and M is 96.

5. The method of claim 1, wherein the UMI is of length 6 nt.

6. The method of claim 1, wherein N is 2 and M is 96 and the oligonucleotide sequences are set forth in SEQ ID NO: 248 through SEQ ID NO: 9463.

7. The method of claim 1, wherein said at least one cell is only one cell in each microwell.

8. The method of claim 7, further comprising, prior to step b), imaging said only one cell in each of said microwells to generate phenotypic imaging information.

9. The method of claim 8, wherein said reverse transcribing generates cDNA, and the method further comprises treating said cDNA to generate a sequencing library.

10. The method of claim 9, further comprising sequencing said sequencing library to generate sequence data.

11. The method of claim 10, wherein said optically demultiplexing the capture bead barcodes generates optical barcode data.

12. The method of claim 11, further comprising linking said sequence data to said phenotypic imaging information using said optical barcode data.

* * * * *